US009506052B2

(12) United States Patent
Samulski

(10) Patent No.: US 9,506,052 B2
(45) Date of Patent: *Nov. 29, 2016

(54) MODIFIED FACTOR VIII AND FACTOR IX GENES

(71) Applicant: ASKLEPIOS BIOPHARMACEUTICAL, INC., Chapel Hill, NC (US)

(72) Inventor: Richard J. Samulski, Chapel Hill, NC (US)

(73) Assignee: Asklepios Biopharmaceutical, Inc., Chapel Hill, NC (US)

( * ) Notice: Subject to any disclaimer, the term of this patent is extended or adjusted under 35 U.S.C. 154(b) by 196 days.

This patent is subject to a terminal disclaimer.

(21) Appl. No.: 14/157,657

(22) Filed: Jan. 17, 2014

(65) Prior Publication Data

US 2014/0193880 A1 Jul. 10, 2014

Related U.S. Application Data

(63) Continuation of application No. 13/494,068, filed on Jun. 12, 2012, now Pat. No. 8,632,765, which is a continuation of application No. 12/305,508, filed as application No. PCT/US2007/071553 on Jun. 19, 2007, now Pat. No. 8,198,421.

(60) Provisional application No. 60/805,171, filed on Jun. 19, 2006, provisional application No. 60/824,338, filed on Sep. 1, 2006, provisional application No. 60/847,337, filed on Sep. 26, 2006.

(51) Int. Cl.
*C12N 15/11* (2006.01)
*C12N 15/63* (2006.01)
*C12N 9/64* (2006.01)
*C07K 14/755* (2006.01)
*A61K 48/00* (2006.01)

(52) U.S. Cl.
CPC ............. *C12N 9/644* (2013.01); *C07K 14/755* (2013.01); *A61K 48/00* (2013.01); *C12N 2799/025* (2013.01)

(58) Field of Classification Search
CPC ...... A61K 48/00; C12N 9/644; C12N 15/00; A01N 63/00; C07H 21/02
See application file for complete search history.

(56) References Cited

U.S. PATENT DOCUMENTS

| 4,501,729 A | 2/1985 | Boucher et al. |
| 5,478,745 A | 12/1995 | Samulski et al. |
| 6,204,059 B1 | 3/2001 | Samulski et al. |
| 6,268,213 B1 | 7/2001 | Samulski et al. |
| 6,410,300 B1 | 6/2002 | Samulski et al. |
| 6,489,162 B1 | 12/2002 | Shenk et al. |
| 6,491,907 B1 | 12/2002 | Rabinowitz et al. |
| 6,548,286 B1 | 4/2003 | Samulski et al. |
| 6,627,617 B1 | 9/2003 | Samulski et al. |
| 6,670,176 B1 | 12/2003 | Samulski et al. |
| 6,703,237 B2 | 3/2004 | Samulski et al. |
| 6,924,365 B1 | 8/2005 | Miller et al. |
| 6,951,753 B2 | 10/2005 | Shenk et al. |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,465,583 B2 | 12/2008 | Samulski et al. |
| 2003/0148506 A1 | 8/2003 | Kotin et al. |
| 2003/0223998 A1 | 12/2003 | Lamber, Jr. et al. |
| 2004/0029106 A1 | 2/2004 | Samulski et al. |
| 2004/0180440 A1 | 9/2004 | Zolotukhin |
| 2004/0197895 A1 | 10/2004 | Kotin et al. |
| 2005/0106558 A1 | 5/2005 | Perabo et al. |
| 2008/0269149 A1 | 10/2008 | Bowles et al. |

FOREIGN PATENT DOCUMENTS

| WO | WO02064799 | 8/2002 |
| WO | WO2005052171 | 6/2005 |

OTHER PUBLICATIONS

Chan, H. et al. "Sustained and complete phenotype correction of Hemophilia B mice following intramuscular injection of AAV1 serotype vectors." Blood, Nov. 16, 2002, vol. 98, No. 11 Part 1, p. 704a, 43$^{rd}$ Annual Meeting of the American Society of Hematology, Orlando, Florida, US.

Chan, H. et al. "Intramuscular Delivery of AAV1 Vectors Resulted in Sustained Expression of Therapeutic Levels of FIX in Hemophilia B Dogs." Blood, Nov. 16, 2002, vol. 100, No. 11, 44$^{th}$ Annual Meeting of the American Society of Hematology, Philadelphia, PA, US.

Connelly et al. 1998. Sustained Phenotypic Correction of Murine Hemophilia a by In Vivo Gene Therapy. Blood, 91:9, pp. 3273-3281.

Hasbrouck et al. (Gene Therapy, 15: 870-875, 2008).

Harding, T.C. et al. "Intravenous administration of an AAV-2 vector for the expression of factor IX in mice and a dog model of hemophilia B." Gene Therapy, vol. 11, No. 2, Jan. 2004, pp. 204-213.

Kajigaya et al. 1991. Self-assembled B19 parvovirus capsids, produced in a baculovirus system, are antigenically and immunogenically similar to native virions. Prog. Nat'l Acad. Sci. USA 88:4646-50.

Kimbauer et al. 1996. Virus-like Particles of Bovine Papillomavirus Type 4 in Propyactic and Therapeutic Immunization. Virology. 219:37-44.

Kudla. G. et al. "High guanine and cytosine content increases mRNA levels in mammalian cells." PLoS Biology, Public Library of Science, US, vol. 4, No. 6, Jun. 1, 2006, pp. E180/933-e180/942.

Manno et al. (Natural Medicine, 12 (3): 342-347, 592; 592; 2006).

(Continued)

*Primary Examiner* — Deborah Crouch
*Assistant Examiner* — Magdalene Sgagias
(74) *Attorney, Agent, or Firm* — Marianne Fuierer; Moore & Van Allen, PLLC

(57) ABSTRACT

The present invention relates to a modified and optimized Factor VIII or Factor IX nucleic acid for inclusion in a chimeric virus vector. Use of such vector can be used for treatment of hemophilia.

4 Claims, 33 Drawing Sheets

(56) References Cited

OTHER PUBLICATIONS

Manno et al. 2006. AAV2 Capid-Specific CD8+ T Cells Limit the Duration of Gene Therapy in Humans and Cross React with AAV-8 Capsid. Blood, 108:11, pp. 138A-139A Part 1.

Nathwani, A. et al. "Self-complementary adeno-associated virus vectors containing a novel liver-specific human factor IX expression cassette enable highly efficient transduction of murine and nonhuman primate liver." Blood, American Society of Hematology, US, vol. 107, No. 7, Apr. 1, 2006, pp. 2653-2661.

Ruffing et al. 1992. Assembly of Virus-like Particles by Recombinant Structural Proteins of Adeno-Associated Virus Type 2 in Insect Cells. Journal of Virology 66: 6922-30.

Samulski et al. 1989. Helper-Free Stocks of Recombinant Adeno-Associated Viruses: Normal Integration Does not Require Gene Expression. Journal of Virology, 63:3822-3828.

Sarker et al. 2004. Total Correction of Hemophilia A Mice with Canine FVIII Using AAV8 Serotype. Blood, 103:4, pp. 1253-1260.

Sharp, P.M. and Li, W.H. 1987. The Codon Adaptation Index—A Measure of Directional Synonymous Codon Usage Bias, and its Potential Applications. Nucleic Acids Research, 15:3.

Warrington et al. (Hum Gene, 119: 571-603, 2006).

Wu, Z. et al. "Optimization of self-complementary AAV vectors for liver-directed expression results in sustained correction of hemophilia B at low vector dose." Molecular Therapy: The Journal of the American Society of Gene Therapy, Feb. 2008, vol. 16, No. 2, pp. 280-289.

Xiao et al. 1997. A Novel 165-Base-Pair Terminal Repeat Sequence is the Sole cis Requirement for the Adeno Associated Virus Life Cycle. Journal of Virology, 71:2, pp. 941-948.

Zhao et al. 2000. BPV1 E2 Protein Enhances Packaging of Full-Length Plasmid DNA in BPV1 Pseudovirions. Virology. 272:382-93.

In Vitro GFP Dose Response Single vs. Double Stranded Genome hFIX In Vitro Every 24 Hours HPMC Cell Lysate
Expression Evaluated with ELISA FIX In Vivo Data R333Q Model 6 Weeks Post Injection

*CTGGCGCGCTCGCTCGCTCACTGAGGCCGCCCGGGCAAAGCCCGGG*
*CGTCGGGCGACCTTTGGTCGCCCGGCCTCAGTGAGCGAGCGAGCGC*
*GCAGAGAGGGAGTGGAATTCGAGC*tcgagcttgggctgcaggtcgagggcactg
ggaggatgttgagtaagatggaaaactactgatgacccttgcagagacagagtattaggacatg
tttgaacaggggccgggcgatcagcaggtagctctagaggatccccgtctgtctgcacatttcgt
agagcgagtgttccgatactctaatctccctaggcaaggttcatatttgtgtaggttacttattctcct
tttgttgactaagtcaataatcagaatcagcaggtttggagtcagcttggcagggatcagcagcct
gggttggaaggagggggtataaaagccccttcaccaggagaagccgtcacacagatccacaa
gctcctgacaggaagctctaggtgactctcttaaggtagccttgcagaagttggtcgtgaggcactgg<u>c</u>
<u>tagccctaaggtaagttggcgccgtttaagggatggttggttggtggggtattaatgtttaattacct</u>
<u>tttttacaggcctgaag</u>atctccaccATGCAGCGCGTGAACATGATCATGGCCGA
GAGCCCTGGCCTGATCACCATCTGCCTGCTGGGCTACCTGCTGAGCG
CCGAGTGCACCGTGTTCCTGGACCACGAGAACGCCAACAAGATCCT
GAACCGGCCCAAGAGATACAACAGCGGCAAGCTGGAGGAGTTCGTG
CAGGGCAACCTGGAGAGGGAGTGCATGGAGGAGAAGTGCAGCTTCG
AGGAGGCCAGGGAAGTGTTCGAGAACACCGAGCGGACCACCGAGTT
CTGGAAGCAGTACGTGGACGGCGACCAGTGCGAGAGCAACCCTTGC
CTGAACGGCGGCAGCTGCAAGGACGACATCAACAGCTACGAGTGCT
GGTGCCCTTTCGGCTTCGAGGGCAAGAACTGCGAGCTGGACGTGAC
CTGCAACATCAAGAACGGCCGCTGCGAGCAGTTCTGCAAGAACAGC
GCCGACAACAAAGTGGTGTGTAGCTGCACCGAGGGCTACAGACTGG
CCGAGAACCAGAAGAGCTGCGAGCCCGCCGTGCCCTTCCCCTGCGG
CAGAGTGAGCGTGTCCCAGACCAGCAAGCTGACCAGAGCCGAGACC
GTGTTCCCCGACGTGGACTACGTGAATAGCACCGAGGCCGAGACCA
TCCTGGACAACATCACCCAGAGCACCCAGTCCTTCAACGACTTCACC
AGAGTTGTGGGCGGCGAGGACGCCAAGCCCGGCCAGTTCCCC

Figure 15 A

TGGCAGGTGGTGCTGAACGGCAAAGTGGATGCCTTCTGCGGCGGCA
GCATCGTGAACGAGAAGTGGATCGTGACAGCCGCCCACTGCGTGGA
GACCGGCGTGAAGATCACCGTGGTGGCCGGCGAACACAATATCGAG
GAGACCGAGCACACCGAGCAGAAGCGGAACGTCATCCGGATTATCC
CCCACCACAACTACAACGCCGCCATCAACAAGTACAACCACGACATC
GCCCTGCTGGAGCTGGACGAGCCTCTGGTGCTGAATAGCTACGTGAC
CCCCATCTGCATCGCCGACAAGGAGTACACCAACATCTTCCTGAAGT
TCGGCAGCGGCTACGTGTCCGGCTGGGGCAGAGTGTTCCACAAGGG
CAGAAGCGCCCTGGTGCTGCAGTACCTGAGAGTGCCCTGGTGGAC
AGAGCCACCTGCCTGAGGAGCACCAAGTTCACCATCTACAACAACAT
GTTCTGCGCCGGCTTCCACGAGGGCGGCAGAGACAGCTGCCAGGGC
GACAGCGGCGGACCCCACGTGACCGAAGTGGAGGGCACCAGCTTCC
TGACCGGCATCATCAGCTGGGGCGAGGAGTGCGCCATGAAGGGCAA
GTACGGCATCTACACCAAAGTGAGCCGGTACGTGAACTGGATCAAG
GAGAAAACCAAGCTGACCTGATGAgcatgcctagagctcgctgatcagcctcgac
tgtgccttctagttgccagccatctgttgtttgcccctccccgtgccttccttgaccctggaaggtg
ccactcccactgtcctttcctaataaaatgaggaaattgcatcgcattgtctgagtaggtgtcattct
attctgggggtggggtggggcaggacagcaagggggaggattgggaagacaatagcagg
catgctggggaa*AGCTTCAGCTAGAGCATGGCTACGTAGATAAGTAGCAT*
*GGCGGGTTAATCATTAACTACAAGGAACCCCTAGTGATGGAGTTGGC*
*CACTCCCTCTCTGCGCGCTCGCTCGCTCACTGAGGCCGGGCGACCAA*
*AGGTCGCCCGACGCCCGGGCTTTGCCCGGGCGGCCTCAGTGAGCGA*
*GCGAGCGCGCAG*

Figure 15 B

Codon Quality Distribution
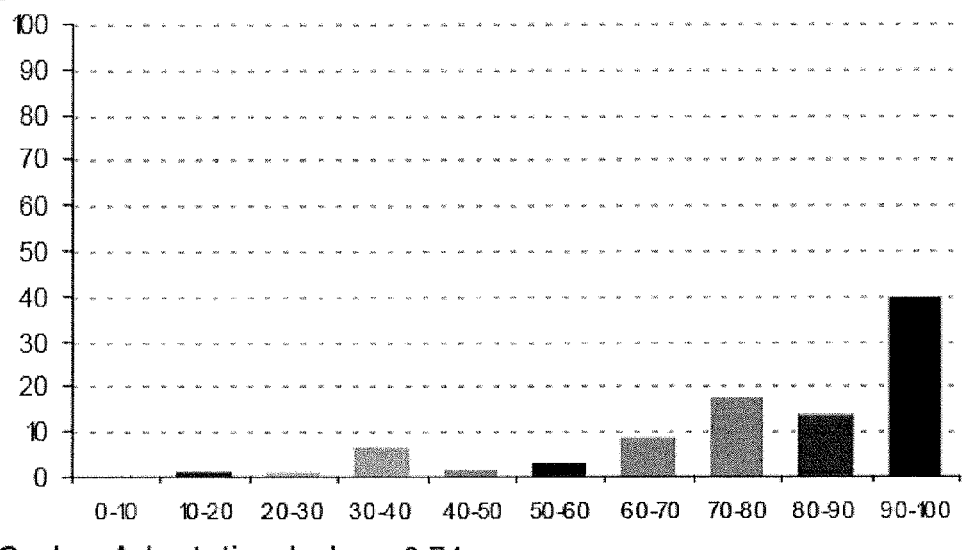
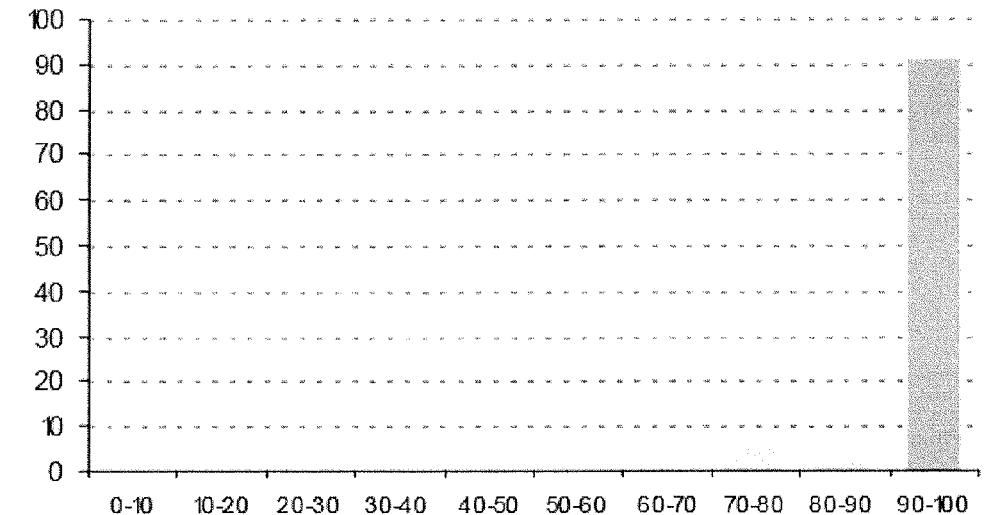
Figure 16

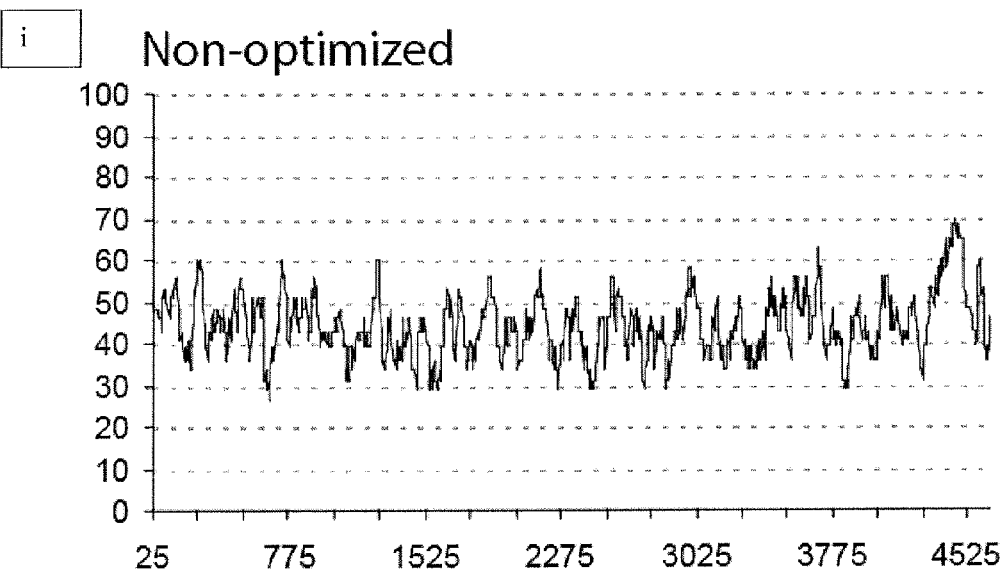
Fig. 3a
Average GC content: 44 %
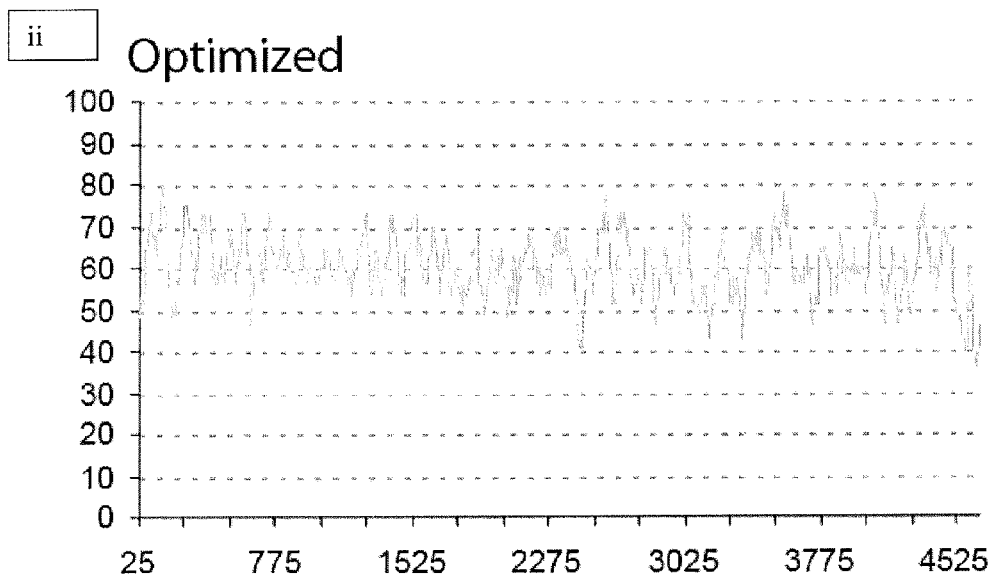
Fig. 3b
Average GC content: 60 %
Figure 18

*ggtaccgccacc*atgcagatcgagctgtccacatgcttttttctgtgcctgctgcggttctgcttcagc
gccacccggcggtactacctgggcgccgtggagctgtcctgggactacatgcagagcgacctggg
cgagctgcccgtggacgcccggttccccccagagtgcccaagagcttccccttcaacaccagcgt
ggtgtacaagaaaaccctgttcgtggagttcaccgtgcacctgttcaacatcgccaagcccaggcc
cccctggatgggcctgctgggccccaccatccaggcgaggtgtacgacaccgtggtgatcaccct
gaagaacatggccagccacccgtgagcctgcacgccgtgggcgtgagctactggaaggcctcc
gagggcgccgagtacgacgaccagaccagccagcgggagaaagaggacgacaaagtctttcc
tggcggcagccacacctacgtgtggcaggtcctgaaagaaaacggccccatggcctccgacccc
ctgtgcctgacctacagctacctgagccacgtggacctggtgaaggacctgaacagcgggctgatt
ggggccctgctggtctgccgggagggcagcctggccaaagagaaaacccagaccctgcacaag
ttcatcctgctgttcgccgtgttcgacgagggcaagagctggcacagcgagaccaagaacagcctg
atgcaggaccgggacgccgcctctgccagagcctggcccaagatgcacaccgtgaacggctacg
tgaacagaagcctgcccggcctgattggctgccaccggaagagcgtgtactggcacgtgatcggc
atgggcaccacacccgaggtgcacagcatctttctggaagggcacacctttctggtgcggaaccac
cggcaggccagcctggaaatcagccctatcaccttcctgaccgcccagacactgctgatggacctg
ggccagttcctgctgttttgccacatcagctctcaccagcacgacggcatggaagcctacgtgaagg
tggactcctgccccgaggaaccccagctgcggatgaagaacaacgaggaagccgaggactacg
acgacgacctgaccgacagcgagatggacgtggtgcggttcgacgacgacaacagccccagctt
catccagatcagaagcgtggccaagaagcaccccaagacctgggtgcactacatcgccgccga
ggaagaggactgggactacgcccccctggtgctggcccccgacgacagaagctacaagagcca
gtacctgaacaatggccccccagcggatcggccggaagtacaagaaagtgcggttcatggcctaca
ccgacgagaccttcaagacccgggaggccatccagcacgagagcggcatcctgggcccctgct
gtacggcgaagtgggcgacacactgctgatcatcttcaagaaccaggccagccggccctacaac
atctacccccacggcatcaccgacgtgcggcccctgtacagcaggcggctgcccaagggcgtga
agcacctgaaggacttcccatcctgcccggcgagatcttcaagtacaagtggaccgtgaccgtgg

Figure 22 A aggacggccccaccaagagcgaccccagatgcctgacccggtactacagcagcttcgtgaacat
ggaacgggacctggcctccgggctgatcggacctctgctgatctgctacaaagaaagcgtggacc
agcggggcaaccagatcatgagcgacaagcggaacgtgatcctgttcagcgtgttcgatgagaac
cggtcctggtatctgaccgagaacatccagcggtttctgcccaaccctgccggggtgcagctggaa
gatcccgagttccaggccagcaacatcatgcactccatcaatggctacgtgttcgacagcctgcagc
tgtccgtgtgtctgcacgaggtggcctactggtacatcctgagcatcggcgcccagaccgacttcctg
agcgtgttcttcagcggctacaccttcaagcacaagatggtgtacgaggacaccctgaccctgttcc
ctttcagcggcgagaccgtgttcatgagcatggaaaaccccggcctgtggatcctgggctgccaca
acagcgacttccggaaccggggcatgaccgccctgctgaaggtgtccagctgcgacaagaacac
cggcgactactacgaggacagctacgaggatatcagcgcctacctgctgtccaagaacaacgcc
atcgagcccagaagcttcagccagaacagccggcaccccagcacccggcagaagcagttcaac
gccaccccccctgtgctgaagcggcaccagagagagatcacccggaccaccctgcagtccgacc
aggaagagatcgattacgacgacaccatcagcgtggagatgaaaaaagaagatttcgacatcta
cgacgaggacgagaaccagagcccccggtccttccagaagaaaacccggcactactttatcgcc
gccgtggagcggctgtgggactacggcatgagcagcagcccccacgtgctgcggaaccgggcc
cagagcggcagcgtgccccagttcaagaaagtggtgttccaggaattcaccgacggcagcttcac
ccagccctgtaccggggcgagctgaacgagcacctggggctgctggggccctacatcagggcc
gaagtggaggacaacatcatggtgaccttccggaatcaggccagcagacccactccttctacagc
agcctgatcagctacgaagaggaccagcggcagggcgctgaaccccggaagaacttcgtgaag
cccaatgagaccaagacctacttctggaaagtgcagcaccacatggccccaccaaggacgagt
tcgactgcaaggcctgggcctacttcagcgacgtggatctggaaaaggacgtgcactctggactga
ttggccctctgctggtgtgccacaccaacaccctgaaccccgcccacggccggcaggtgaccgtgc
aggaattcgccctgttcttcaccatcttcgacgagaccaagtcctggtacttcaccgagaatatggaa
cggaactgcagagcccctgcaacatcagatggaagatcctaccttcaaagagaactaccggttc
cacgccatcaacggctacatcatggacaccctgcctggcctggtgatggcccaggaccagaggat ccggtggtatctgctgtccatgggcagcaacgagaatatccacagcatccacttcagcggccacgt
gttcaccgtgaggaagaaagaagagtacaagatggccctgtacaacctgtaccccggcgtgttcg
agaccgtggagatgctgcccagcaaggccggcatctggcgggtggagtgtctgatcggcgagca
cctgcatgccgggatgagcaccctgtttctggtgtacagcaacaagtgccagaccccctgggcat
ggccagcggccacatccgggacttccagatcaccgcctccggccagtacggccagtgggcccc
aagctggcccggctgcactacagcggcagcatcaacgcctggtccaccaaagagcccttcagctg
gatcaaggtggacctgctggcccctatgatcatccacggcattaagacccagggcgccaggcaga
agttcagcagcctgtacatcagccagttcatcatcatgtacagcctggacggcaagaagtggcaga
cctaccggggcaacagcaccggcaccctgatggtgttcttcggcaacgtggacagcagcggcatc
aagcacaacatcttcaaccccccatcatcgcccggtacatccggctgcaccccacccactacag
catcagatccaccctgcggatggaactgatgggctgcgacctgaactcctgcagcatgcctctggg
catggaaagcaaggccatcagcgacgcccagatcacagccagcagctacttcaccaacatgttc
gccacctggtcccctccaaggccaggctgcacctgcagggccggtccaacgcctggcggcctca
ggtgaacaaccccaaagaatggctgcaggtggactttcagaaaaccatgaaggtgaccggcgtg
accacccagggcgtgaaaagcctgctgaccagcatgtacgtgaaagagtttctgatcagcagcag
ccaggacggccaccagtggaccctgttctttcagaacggcaaggtgaaagtgttccagggcaacc
aggactccttcaccccgtggtgaactccctggaccccccctgctgacccgctacctgcggatcca
cccccagtcttgggtgcaccagatcgccctgaggatggaagtgctgggatgtgaggcccaggatct
gtactgaCTCGAGGGGTGGCCACTGCAGCACCTGCCACTGCCGTCAC
CTCTCCCTCCTCAGCTCCAGGGCAGTGTCCCTCCCTGGCTTGCCTT
CTACCTTTGTGCTAAATCCTAGCAGACACTGCCTTGAAGCCTCCTG
AATTAACTATCATCAGTCCTGCATTTCTTTGGTGGGGGCCAGGAGG
GTGCATCCAATTTAACTTAACTCTTACCTATTTTCTGCAGGGGATCT
CAGTCGACGAGCTC

Figure 22 C atgcagatcgagctgagtacctgcttttcctctgcctgctgcggttctgcttcagcgccacccggc
ggtactacctgggcgccgtggagctgagttgggactacatgcagagcgacctgggcgagctg
cccgtggacgcccggttcccccctcgggtgcccaagagcttccccttcaacaccagcgtggtg
tacaagaaaaccctgttcgtggagttcaccgtgcacctgttcaacatcgccaagcccaggccc
ccctggatgggcctgctgggccccaccatccaggccgaggtgtacgacaccgtggtgatcac
cctgaagaacatggccagccacccgtgagcctgcacgccgtgggcgtgagctactggaag
gccagtgagggcgccgagtacgacgaccagaccagccagcgggagaaagaggacgac
aaggttttccctggcggcagccacacctacgtgtggcaggtcctgaaagaaaacggccccat
ggcctccgacccctgtgcctgacctacagctacctgagccacgtggacctggtcaaggacct
gaacagcggcctgatcggcgcgctgctggtctgccgggagggcagcctggccaaagagaa
aacccagaccctgcacaagttcatcctgctgttcgctgtgttcgacgagggcaagagctggca
cagcgagaccaagaacagcctgatgcaggaccgggacgccgccagcgctcgcgcctggc
ccaagatgcacaccgtgaacggatacgtgaaccggtccctgcccgggctgatcggctgcca
ccggaagagcgtgtactggcacgtgatcggcatgggcaccacgcccgaggtgcacagcatc
ttcctcgagggccacaccttcctcgtgcggaaccaccggcaggccagcctcgagatcagccc
catcaccttcctcaccgcccagacgctgctgatggacctgggccagttcctgctcttctgccaca
tcagctcgcaccagcacgacggcatggaagcctacgtgaaggtggacagttgccccgagga
accccagctgcggatgaagaacaacgaggaagccgaggattacgacgacgacctgaccg
acagcgagatggacgtggtgcggttcgacgacgacaacagccccagcttcatccagatccg
gtccgtggccaagaagcacccaagacctgggtgcactacatcgccgccgaggaagagga
ctgggactacgcccccctggtgctggccccgacgaccggtcctacaagagccagtacctga
acaacgggccccagcggatcggccggaagtacaagaaagtgcggttcatggcctacaccg
acgagaccttcaagacccgggaggccatccagcacgagagcggcatcctgggccccctgct
gtacggcgaggtcggcgacaccctgctgatcatcttcaagaaccaggccagccggccctac
aacatctaccccacggcatcaccgacgtgcggcccctgtacagcaggcggctgcccaagg
gcgtgaagcacctgaaggacttccccatcctgcccggcgagatcttcaagtacaagtggacc

Figure 23 A gtgaccgtggaggacggccccaccaagagcgaccccgctgcctcacccggtactacagc agcttcgtgaacatggagcgggacctggcctccggcctcatcgggcccctgctcatctgctaca aagaaagcgtggaccagcggggcaaccagatcatgagcgacaagcggaacgtgatcctgt tctcggtgttcgacgagaaccggagttggtatctgacggagaacatccagcggttcctccccaa ccctgccggcgtgcagctcgaggaccccgagttccaggccagcaacatcatgcactccatca atggctacgtgttcgacagcctgcagctgtccgtgtgcctccacgaggtggcctactggtacatc ctgagcatcggcgcccagaccgacttcctgagcgtgttcttcagcggctacaccttcaagcaca agatggtgtacgaggacaccctgaccctgttcccgttcagcggcgagaccgtgttcatgagcat ggaaaaccccggcctgtggatcctgggctgccacaacagcgacttccggaaccggggcatg accgccctgctgaaggtgtccagctgcgacaagaacaccggcgactactacgaggacagct acgaggacatcagcgcctacctgctgtccaagaacaacgccatcgagccccggtccttcagc cagaacagccggcaccccagcacccggcagaagcagttcaacgccaccccccctgtgctg aagcggcaccagcgcgagatcacccggaccaccctgcagtccgaccaggaagagatcga ctacgacgacaccatcagcgtggagatgaagaaagaggacttcgacatctacgacgagga cgagaaccagagccccgcagcttccagaagaaaacccggcactacttcatcgccgcggtg gagcggctgtgggactacggcatgagcagcagcccccacgtgctgcggaaccgggcccag agcggcagcgtgccccagttcaagaaagtggtgttccaggaattcaccgacggcagcttcac ccagccctgtaccggggcgagctgaacgagcacctggggctgctggggccctacatccgc gcggaggtggaggacaacatcatggtgaccttccggaaccaggcctcccgcccctactccttc tacagcagcctgatcagctacgaagaggaccagcggcagggcgcggagccccggaaga acttcgtgaagcccaacgagaccaagacctacttctggaaggtgcagcaccacatggcccc caccaaggacgagttcgactgcaaggcctgggcctacttcagcgacgtggacctcgagaag gacgtgcactccgggctcatcggcccgctcctcgtgtgccacaccaacaccctgaaccccgc ccacggccggcaggtgaccgtgcaggaattcgccctgttcttcaccatcttcgacgagaccaa gtcgtggtacttcaccgagaacatggaacgcaactgcagggcccccctgcaacatccagatgg aagatcccaccttcaaagagaactaccggttccacgccatcaacggctacatcatggacacc ctgcccggcctggtgatggcccaggaccagcgcatccggtggtatctgctgtccatgggcagc

Figure 23B aacgagaacatccacagcatccacttcagcggccacgtgttcaccgtccggaagaaagaag
agtacaagatggccctgtacaacctgtaccccggcgtgttcgagaccgtggagatgctgccca
gcaaggccggcatctggcgggtggagtgcctgatcggggagcacctccacgccggcatgtc
caccctgttcctcgtgtacagcaacaagtgccagaccccctgggcatggccagcggccaca
tccgggacttccagatcaccgcctccggccagtacggccagtgggcccccaagctggccg
gctgcactacagcggcagcatcaacgcctggtccaccaaagagcccttcagctggatcaag
gtggacctgctcgccccatgatcatccacgggatcaagacccagggcgccaggcagaagt
tcagcagcctgtacatcagccagttcatcatcatgtacagcctggacggcaagaagtggcag
acctaccggggcaacagcaccggcaccctgatggtgttcttcggcaacgtggacagcagcg
gcatcaagcacaacatcttcaaccccccatcatcgcccggtacatccggctgcaccccacc
cactacagcatccggtccaccctgcggatggaactgatgggctgcgacctgaactcctgcag
catgcccctggggatggaaagcaaggccatcagcgacgcccagatcacggccagcagcta
cttcaccaacatgttcgccacctggtcccctccaaggcccgcctgcacctgcagggccggtc
caacgcctggcggcctcaggtcaacaaccccaaagagtggctgcaggttgacttccagaaa
accatgaaggtgaccggcgtgaccacccagggggtgaagagcctgctgaccagcatgtac
gtgaaagagttcctcatcagcagcagccaggacggccaccagtggacgctgttcttccagaa
cggcaaggtcaaggtgttccagggcaaccaggacagtttcacgcccgtggtgaactccctgg
accccccctgctgacccgctacctgcggatccaccccagagctgggtccaccagatcgcc
ctgcgcatggaagtcctcggctgcgaggcgcaggacctgtactga*CTCGAGGGGTG*
*GCCACTGCAGCACCTGCCACTGCCGTCACCTCTCCCTCCTCAG*
*CTCCAGGGCAGTGTCCCTCCCTGGCTTGCCTTCTACCTTTGTG*
*CTAAATCCTAGCAGACACTGCCTTGAAGCCTCCTGAATTAACT*
*ATCATCAGTCCTGCATTTCTTTGGTGGGGGGCCAGGAGGGTGC*
*ATCCAATTTAACTTAACTCTTACCTATTTTCTGCAGGGGATCTC*
*AGTCGACGAGCTC*

Figure 23C

```
Query    1    ATGCAGCGCGTGAACATGATCATGGCAGAATCACCAGGCCTCATCACCATCTGCCTTTTA    60
              ||||||||||||||||||||||||||||||||||||||||||||||||||||||||||||
Sbjct    1    ATGCAGCGCGTGAACATGATCATGGCAGAATCATGGCCGAGAGCCCTGCCTGATCACCATCTGCCTGCTG    60

Query    61   GGATATCTACTCAGTGCTGAATGTACAGTTTTCTTGATCATGAAAACGCCAACAAAATT    120
              ||||||||||||||||||||||||||||||||||||||||||||||||||||||||||
Sbjct    61   GGCTACCTGCTGAGCGCCGAGTGCACCGTGTTCCTGGACCACGAGAGTTGTTCAAGGAACCAAGATC    120

Query    121  CTGAATCGGGCCAAAGAGGTATAATTCAGTGTAAATTCAGTGGCAACACAGCGCCCAAGGAACCTT    180
              ||||||||||||||||||||||||||||||||||||||||||||||||||||||||||
Sbjct    121  CTGAACCGGGCCCAAGAGATACAACAGCGACGGCAACGCTGGAGCTGCGTGCAGGGCAACCTG    180

Query    181  GAGAGAGAATGTATGGAAGAAAAAGTGTAGTTTTGAAGAAGCACGAGAAGTTTTTGAAAAC    240
              ||||||||||||||||||||||||||||||||||||||||||||||||||||||||||
Sbjct    181  GAGAGGGAGTGCATGGAGGAGAGAAGTGCAGCTTCGAGGAGGCCAAGGAAGTGTTCGAGAAC    240

Query    241  ACGGAAAGAACAACTGAATTTTGGAAGCAGTATGTTGATGGTGACCAGTGTGAGTCCAAT    300
              ||||||||||||||||||||||||||||||||||||||||||||||||||||||||||
Sbjct    241  ACCGAGCGGACCACCGAGTTCTGGAAGCAGTACGTGGACGGCGACCAGTGCGAGAGCAAC    300

Query    301  CCATGTTTAAATGGCGGCAGTTGCAAGGATGACATTAATTCCTATGAATGTTGGTGTCCC    360
              ||||||||||||||||||||||||||||||||||||||||||||||||||||||||||
Sbjct    301  CCTTGCCTGAACGGGGCAGTGCAAGGACGACATCAACAGCTACGAGTGCTGGTGCCCT    360
```

Figure 24 A

```
Query  361  TTTGGATTTGAAGGAAAGAACTGTGAGCTCGATGTAACATTAAGAATGGCAGA  420
            ||||  || |||||  |||| ||||||||||||| ||||| | |||| ||||
Sbjct  361  TTCGGCTTCGAGGGCAAGAACTGCGAGCTGGACCTGCAACATCAAGAACGGCGC  420

Query  421  TGCGAGCAGTTTTTGTAAAATAGTGCTGATAACAAGGTGGTTTGCTCCTGTACTGAGGGA  480
            ||||||||||| | ||  || ||||| ||||||| ||||||||| | ||||| ||||| 
Sbjct  421  TGCGAGCAGTTCTGCAAGAACAGCGCCGACAACAAAGTGGTGTAGCTGCACCGAGGGC  480

Query  481  TATCGACTTGCAGAAAAACCAGAAGTCCTGTGAACCAGCAGTGCCATTTCCATGCGGCCGC  540
            || |||||||| || ||||||||||| ||||| ||| || |||| ||||| ||||| ||
Sbjct  481  TACAGACTGGCCGAGAACCAGAGAACCAGAGAGCTGCGCCCGTGCCCTTCCCCTGCGGCAGA  540

Query  541  GTTTCTGTTTCACAAACTTCTAAGCTCACCCGTGCTGAGACTGTTTTTCCTGATGTGGAC  600
            || |||||| ||||| |||| | |||| ||||||| |||| |||||| ||||||||||
Sbjct  541  GTGAGCGTGTCCCAGACAAGCTGACCAGCAAGCTGAGACCGTGTTCCCCGACGTGGAC  600

Query  601  TATGTAAATTCTACTGAAGCTGAAACCATTTTGGATAACATCACTCAAAGCACCCAATCA  660
            || ||||| || || |||| ||||| |||| ||||||||||| || ||||||| ||| 
Sbjct  601  TACGTGAATAGCACCGAGGCCGAGACCATCCTGGACAACATCACCCAGAGCACCAGTCC  660

Query  661  TTTAATGACTTCACTCGGGTTGTTGGTGGAGAAGATGCCAAACCAGGTCAATTCCCCTTGG  720
            || ||||||||| |||| ||||||||||| ||||||||| |||||||||  ||||| |||
Sbjct  661  TTCAACGACTTCACCAGAGTTGTGGGCGGCGAGGACGCCAAGCCCGGCCAGTTCCCCCTGG  720
```

Figure 24B

| | | |
|---|---|---|
| Query 721 | CAGGTTGTTTTGAATGGTAAAGTTGATGCATTCTGTGGAGGCTCTATCGTTAATGAAAAA | 780 |
| Sbjct 721 | CAGGTGGTGCTGAACGGCAAAGTGCAAAGTGGATGCCTTCGCGGCGGCAGCATCGTGAACGAGAAG | 780 |
| Query 781 | TGGATTGTAACTGCTGCCCACTGTGTTGAAACTGGTGTTAAAATTACAGTTGTCGCAGGT | 840 |
| Sbjct 781 | TGGATCGTGACAGCCGCCCACTGCGTGGAGACCGGCGTGAAGATCACCGTGGTGGCCGGC | 840 |
| Query 841 | GAACATAATATTGAGGAGACAGAACATACAGAGCAAAAGCGAAATGTGATTCGAATTATT | 900 |
| Sbjct 841 | GAACACAATATCGAGGAGACCGAGCACACCGAGCAGAAGCGGAACGTCATCCGGATTATC | 900 |
| Query 901 | CCTCACCACAACTACAATGCAGCTATTAATAAGTACAACCATGACATTGCCCTTCTGAA | 960 |
| Sbjct 901 | CCCCACCACAACTACAACGCCGCCATCAACAAGTACAACCACGACATCGCCCTGCTGGAG | 960 |
| Query 961 | CTGGACGAACCCCTTAGTGCTAAACAGCTACGTTACACCTATTTGCATTGCTGACAAGGAA | 1020 |
| Sbjct 961 | CTGGACGAGCCCCTCTGGTGTGCTGAATAGCTACGTGACCCCCATCTGCCGACAAGGAG | 1020 |
| Query 1021 | TACACGAACATCTTCCTCAAATTTGGATCTGGCTATGTAAGTGGCTGGGAAGAGTCTTC | 1080 |
| Sbjct 1021 | TACACCAACATCTTCCTGAAGTTCGGCAGCGGCTACGTGTCCGGCTGGGGCAGAGTGTTC | 1080 |

Figure 24 C

```
Query  1081  CACAAAGGGAGAGATCAGCTTTAGTTCTTCAGTACCTTAGAGTTCCACTTGTTGACCGAGCC  1140
             ||||||||| |||||||||||| |||| | |||| |||| |||||||||||||| ||||||
Sbjct  1081  CACAAGGGCAGAAGCGCCCTGTGCTGCAGTACCTGAGAGTGCCCCTGGTGGACAGAGCC  1140

Query  1141  ACATGTCTTCGATCTACACAAAGTTCACCATCTATAACAACATGTTCTGTGCTGGCTTCCAT  1200
             ||||||||| |||||||| ||||||||||||||| ||||| |||||||| ||||||||| |
Sbjct  1141  ACCTGCCTGAGGAGCACCAAGTTCACCATCTACAACAACATGTTCTGCGCCGGCTTCCAC  1200

Query  1201  GAAGGAGGTAGAGATTCATGTCAAGGAGATAGTGGGGGACCCCATGTTACTGAAGTGGAA  1260
             || ||  | |||| |||| |||||| ||||||||| |||||| |||||||||||||||||
Sbjct  1201  GAGGGCGGCAGAGACAGCTGCCAGGGCGACAGCGGCGACCCCACGTGACCGAAGTGGAG  1260

Query  1261  GGGACCAGTTTCTTAACTGGAATTATTAGCTGGGGTGAAGAGTGTGCAATGAAAGGCAAA  1320
             ||||||||| || || |||||| |||| | ||||| ||||||||||||||||||||| |
Sbjct  1261  GGCACCAGCTTCCTGACCGGCATCATCAGCTGGGGCGAGGAGTGCGCCATGAAGGGCAAG  1320

Query  1321  TATGGAATATATACCAAGGTATCCCGGTATGTCAACTGGATTAAGGAAAAAACAAAGCT  1379
             || |||||||||||||||| ||| | |  ||  |  ||||| ||||| ||| ||||||
Sbjct  1321  TACGGCATCTACACCAAAGTGAGCCGGTACGTGAACTGAACTGGATCAAGGAGAAAACCAAGCT  1379
```

Figure 24D

MODIFIED FACTOR VIII AND FACTOR IX GENES

CROSS REFERENCE TO RELATED APPLICATIONS

The present application is a continuation application of and claims priority to U.S. patent application Ser. No. 13/494,068, filed on Jun. 12, 2012, now U.S. Pat. No. 8,632,765, which in turn was a continuation application of and claims priority to U.S. patent application Ser. No. 12/305,508 filed on Sep. 23, 2009, now U.S. Pat. No. 8,198,421, which in turn was a 35 U.S.C. §371 application of PCT Application No. PCT/US2007/071553 filed in the U.S. Patent and Trademark Office, PCT Division, on Jun. 19, 2007, which in turn claims priority from U.S. Provisional Patent Application Ser. No. 60/805,171, filed on Jun. 19, 2006, U.S. Provisional Patent Application Ser. No. 60/824,338, filed on Sep. 1, 2006, and U.S. Provisional Patent Application Ser. No. 60/847,337 was filed on Sep. 26, 2006; the contents of which are incorporated herein by reference in their entirety.

BACKGROUND OF THE INVENTION

Field of the Invention

The invention relates to modified Factor VIII (FVIII) and Factor XI (FIX) genes, nucleic acid vectors including the modified genes, optimized viral capsids including the modified genes, methods of using the modified genes in the treatment of FVIII and FIX deficiencies, such as hemophilia A and hemophilia B.

Discussion of Related Art

Hemophilia is a blood disorder in which the blood does not clot properly. Inadequate clotting causes excessive bleeding when the hemophiliac is injured. Hemophilia is a genetic coagulation disorder characterized by inadequate clotting and excessive bleeding. Several types of hereditary hemophilia are differentiated by the clotting factor affected. Hemophilia A is caused by a deficiency in blood coagulation Factor VIII (FVIII). Hemophilia B is caused by a deficiency in blood coagulation Factor IX (FIX).

Hemophilia B is an X-linked disorder and the condition affects ~1 in 30 000 males. In its severe form (about 60% of the Hemophilia B population) Hemophilia B can be fatal. Spontaneous hemorrhage into joints and muscles can lead to permanent disability.

Gene therapy has been proposed as treatment modality for supplementing deficiencies in clotting factors in hemophiliacs. However, as in many areas of gene therapy, theory is much more straightforward than successful, effective application. Many difficulties have been encountered in prior attempts to engineer FVIII or FIX constructs that are suitable for treatment of humans.

For example, Manno et al. reported AAV2 mediated delivery of FIX to the liver of human subjects in a Phase I study resulted in expression of biologically active FIX levels (Manno et al., Blood, (2006), pp.). Connelly et al. reported that treatment of FVIII-deficient mice with human FVIII-encoding adenoviral vectors resulted in expression of biologically active human FVIII (Connelly et al., Blood, Vol. 91, No. 9 (1998), pp. 3273-3281). Sarker et al. reported that use of AAV8 serotype in combination with FVIII corrected plasma FVIII activity in mouse models (Sarkar et al., Blood, Vol. 103, No. 4 (2004), pp. 1253-1260).

However, as in many areas of gene therapy, theory is much more straightforward than successful, effective implementation. Difficulties in implementation of gene therapy techniques include problems encountered in the use of viruses as gene vectors. While viruses are effective as gene vectors because they can be used to transduce cells leading to protein expression in vivo, the proteins coating the virus particle may activate the body's immune system.

Thus, there is therefore a need for systems which efficiently express the target protein in sufficient quantity to reduce the required dose of viral vector to tolerable levels.

SUMMARY OF THE INVENTION

The present invention provides for modified Factor VIII (FVIII) and Factor XI (FIX) genes, nucleic acid vectors including the modified genes, optimized viral capsids including the modified genes, and methods of using the modified genes in the treatment of FVIII and FIX deficiencies, such as hemophilia A and hemophilia B.

In one aspect, the present invention provides for optimized FVIII or FIX genes for treating hemophilia in a human subject wherein the optimized genes have been modified to increase CG sequences and reduce cis motifs. Preferably the optimized genes comprise sequences SEQ ID NO: 7, 12 or 15.

In another aspect, the present invention provides for a chimeric virus vector comprising optimized FVIII or FIX genes for treating hemophilia in a human subject wherein the optimized genes have been modified to increase CG sequences and reduce cis motifs. Preferably, the chimeric virus vector includes SEQ ID NO. 7 or its complement flanked by AAV TRs, such as SEQ ID NO. 2 and SEQ ID NO. 9, wherein the sequence of SEQ ID NO. 2 is at a 5' terminus and the SEQ ID NO. 9 at a 3' terminus thereof. The chimeric virus vector may comprise the nucleotide sequence of SEQ ID NO. 1.

In yet another aspect, the present invention provides for a method of treating hemophilia in a subject, the method comprising:
a. providing at least one recombinant virus vector comprising a nucleotide sequences for comprising a modified FVIII or FIX gene; and
b. administering the recombinant virus vector to the subject under conditions such that said FVIII or FIX nucleotide sequences are expressed at a level which produces a therapeutically effective amount of FVIII or FIX in the subject.

In a still further aspect, the present invention provides for a method of transducing a muscle cell or liver cell with a modified FVIII or FIX gene, the method comprising contacting the liver cell with a recombinant Biological Nano Particle (BNP) virus vector comprising an optimized FIX gene comprising the sequence of SEQ ID NO. 7 or an optimized FVIII gene comprising the sequence of SEQ ID NO: 12 or 15.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe.

Thus, another aspect of the present invention provides for therapies to treat hemophilia, including: gene therapy based on administration of nucleotide sequence encoding for optimized FVIII or FIX genes.

In an alternative aspect, the present invention provides an expression vector comprising a polynucleotide that encodes an optimized FVIII or FIX gene or fragment thereof. In one embodiment the expression vector is an AVV virus vector including the sequence of AAV2 Capsid 2.5 (SEQ ID NO. 17)

In yet another aspect, the present invention provides a recombinant host cell transfected with a polynucleotide that encodes an optimized FVIII or FIX peptide of the present invention.

In a still further aspect, the present invention contemplates a process of preparing an optimized FVIII or FIX peptide or fragment thereof comprising:
  a. transfecting a cell with polynucleotide that encodes the FVIII or FIX peptide or fragment thereof to produce a transformed host cell; and
  b. maintaining the transformed host cell under biological conditions sufficient for expression of the peptide.

In another aspect, the present invention relates to the use of an optimized FVIII or FIX peptide or fragment thereof of the present invention in the use of a medicament for the treatment of hemophilia.

The present invention also provides for a pharmaceutical compositions comprising optimized FVIII or FIX genes for treating hemophilia in a human subject wherein the optimized genes have been modified to increase CG sequences and reduce cis motifs and in combination with a pharmaceutically acceptable carrier. The optimized genes may comprise sequences SEQ ID NOs: 7, 12 or 15.

Other features and advantages of the invention will be apparent from the following detailed description, drawings and claims.

BRIEF DESCRIPTION OF THE FIGURES

FIGS. 15 A and B shows the sequence of the vector (SEQ ID NO 1) of FIG. 14 and showing Bold Italic upper case: Left mutant ITR (SEQ ID NO: 2); Bold lower case: TTR promoter (SEQ ID NO: 3); Regular lower case: stuffer sequence (SEQ ID NO: 4); Bold underlined lower case: MVM intron (SEQ ID NO: 5); Regular lower case: stuffer sequence (SEQ ID NO: 6); Bold Italic Underlined upper case: optimized hFIX cDNA (SEQ ID NO: 7); Bold lower case: Bovine hormone polyA ((SEQ ID NO: 8) and Bold Italic upper case: Right ITR (SEQ ID NO: 9)

FIG. 16 i and ii shows the percentage of sequence codons falling into a certain quality class relative to SEQ ID NO: 19 (non-optimized) and SEQ ID NO: 12 (optimized).

FIG. 18 i an ii shows an increase in GC content from 44% (SEQ ID NO: 19) non-optimized to 60% optimized (SEQ ID NO: 12).

FIGS. 22 A, B and C show nucleotide sequence for modified FVIII gene SEQ ID NO: 10 including SEQ ID NO: 11, SEQ ID NO: 12 (modified FVIII cDNA) and SEQ ID NO: 13.

FIGS. 23 A, B and C shows nucleotide sequence for modified FVIII gene SEQ ID NO: 14 including SEQ ID NO: 15 (modified FVIII cDNA) and SEQ ID NO: 16.

FIGS. 24 A, B, C and D shows the comparison in CG content between the wild type FIX sequence (SEQ ID NO: 18) (Query line in Blast) and the optimized sequence (SEQ ID NO: 7) (Subject line in Blast) of the present invention.

DETAILED DESCRIPTION OF THE INVENTION

Definitions

Figure 1:
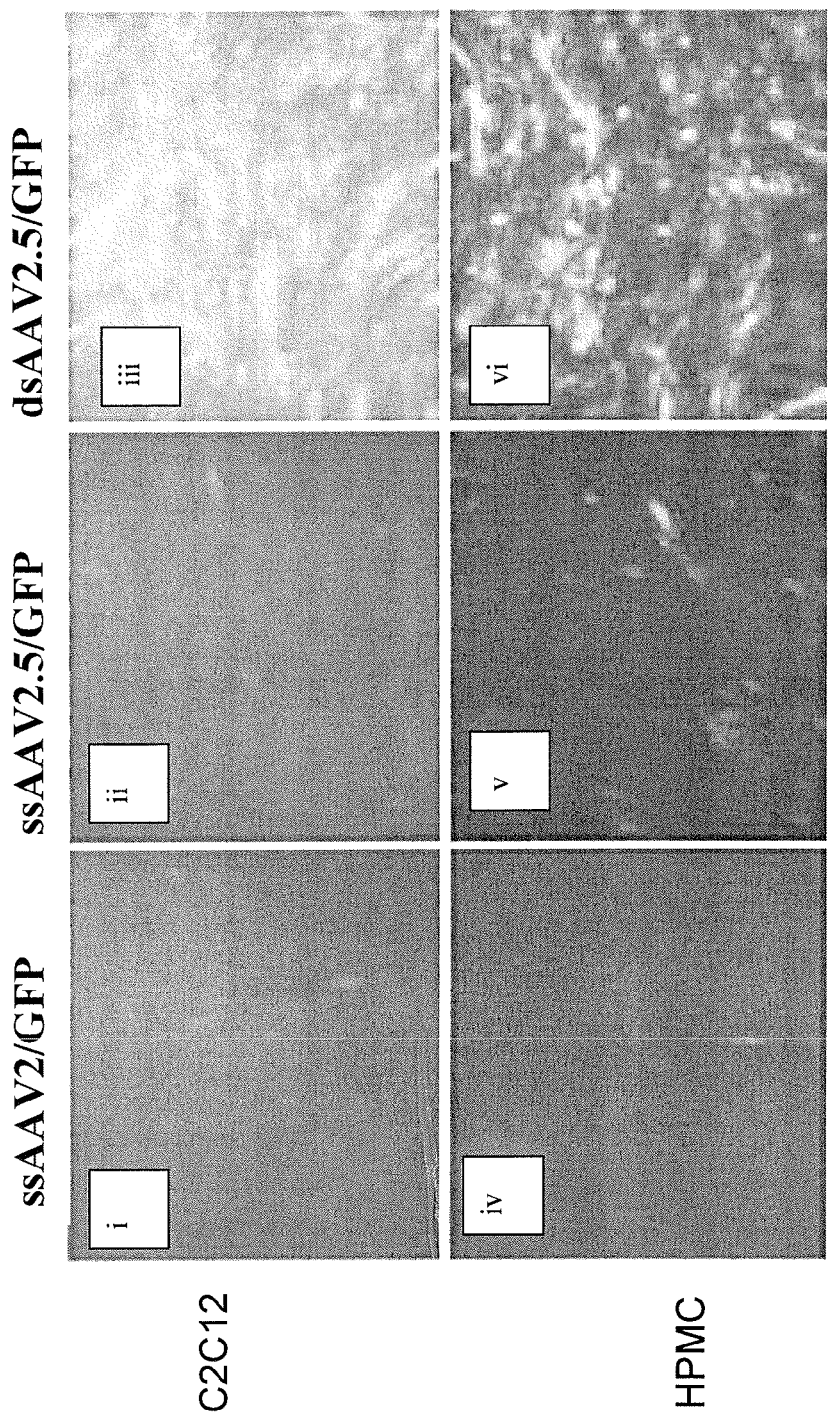
FIG. 1 i, ii, iii, iv, v and vi shows in vitro GFP transduction $1 \times 10^9$ vg (viral genomes) HPMC 530,000 cells.

Unless otherwise defined, all technical and scientific terms used herein have the meaning commonly understood by one of ordinary skill in the art to which this invention belongs. The terminology used herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. The following terms have the meanings given:

"AAV Cap" means AAV Cap proteins, VP1, VP2 and VP3 and analogs thereof.

"AAV Rep" means AAV Rep proteins and analogs thereof.

"AAV TR" means a palindromic sequence, comprising mostly complementary, symmetrically arranged sequences, and includes analogs of native AAV TRs and analogs thereof.

"Biologically-effective" with respect to an amount of a viral vector is an amount that is sufficient to result in infection (or transduction) and expression of the transgene in a target cell.

"Cis-motifs" includes conserved sequences such as found at or close to the termini of the genomic sequence and recognized for initiation of replication; cryptic promoters or sequences at internal positions likely used for transcription initiation or termination.

"Chimeric" means, with respect to a viral capsid or particle, that the capsid or particle includes sequences from different parvoviruses, preferably different AAV serotypes, as described in Rabinowitz et al., U.S. Pat. No. 6,491,907, entitled "Recombinant parvovirus vectors and method of making," granted on Dec. 10, 2002, the disclosure of which is incorporated in its entirety herein by reference. A particularly preferred chimeric viral capsid is the AAV2.5 capsid, which has the sequence of the AAV2 capsid with the following mutations: 263 Q→A; 265 insertion T; 705 N→A; 708 V→A; and 716 T→N. wherein the nucleotide sequence expressing such capsid is defined as SEQ ID NO: 17. Additional preferred chimeric viral capsids are described in copending PCT Application No. PCT/US07/01668, the disclosure of which is incorporated in its entirety herein by reference.

"Flanked," with respect to a sequence that is flanked by other elements, indicates the presence of one or more the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence (e.g., a transgene) that is "flanked" by two other elements (e.g., TRs), indicates that one element is located 5' to the sequence and the other is located 3' to the sequence; however, there may be intervening sequences therebetween.

"Polynucleotide" means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

"Transduction" of a cell by a virus means that there is transfer of DNA or RNA from the virus particle to the cell.

"Transfection" of a cell means that genetic material is introduced into a cell for the purpose of genetically modifying the cell. Transfection can be accomplished by a variety of means known in the art, such as transduction or electroporation.

"Polypeptide" encompasses both peptides and proteins, unless indicated otherwise.

"Transgene" is used in a broad sense to mean any heterologous nucleotide sequence incorporated in a viral vector for expression in a target cell and associated expression control sequences, such as promoters. It is appreciated by those of skill in the art that expression control sequences will be selected based on ability to promote expression of the transgene in the target cell. An example of a transgene is a nucleic acid encoding a therapeutic polypeptide.

"Vector," means a recombinant plasmid or virus that comprises a polynucleotide to be delivered into a host cell, either in vitro or in vivo.

"Recombinant" means a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

"Substantial homology" or "substantial similarity," means, when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the sequence.

"Recombinant viral vector" means a recombinant polynucleotide vector comprising one or more heterologous sequences (i.e., polynucleotide sequence not of viral origin). In the case of recombinant parvovirus vectors, the recombinant polynucleotide is flanked by at least one, preferably two, inverted terminal repeat sequences (ITRs).

"Serotype" with respect to vector or virus capsid is defined by a distinct immunological profile based on the capsid protein sequences and capsid structure.

"Peptide", "polypeptide" and "protein" are used interchangeably to denote a sequence polymer of at least two amino acids covalently linked by an amide bond.

"Homologous" used in reference to peptides, refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" as used herein means that a sequence is at least 50% identical, and preferably at least 75% and more preferably 95% homology to the reference peptide. Additional peptide sequence modification are included, such as minor variations, deletions, substitutions or derivitizations of the amino acid sequence of the sequences disclosed herein, so long as the peptide has substantially the same activity or function as the unmodified peptides. Derivatives of an amino acid may include but not limited to trifluoroleucine, hexafluoroleucine, 5,5,5-trifluoroisoleucine, 4,4,4-trifluorovaline, p-fluorophenylaline, o-fluorotyrosine, m-fluorotyrosine, 2,3-difluorotyrosine, 4-fluorohistidine, 2-fluorohistidine, 2,4-difluorohistidine, fluoroproline, difluoroproline, 4-hydroxyproline, selenomethionine, telluromethionine, selenocysteine, selenatryptophans, 4-aminotryptophan, 5-aminotryptophan, 5-hydroxytryptophan, 7-azatryptophan, 4-fluorotryptophan, 5-fluorotryptophan, 6-fluorotryptophan, homoallylglycine, homopropargylglycine, 2-butynylglycine, cis-crotylglycine, allylglycine, dehydroleucine, dehydroproline, 2-amino-3-methyl-4-pentenoic acid, azidohomoalanine, asidoalanine, azidonorleucine, p-ethynylphenylalanine, p-azidophenylalanine, p-bromophenylalanine, p-acetylphenylalanine and benzofuranylalanine. Notably, a modified peptide will retain activity or function associated with the unmodified peptide, the modified peptide will generally have an amino acid sequence "substantially homologous" with the amino acid sequence of the unmodified sequence.

The invention provides modified nucleic acids encoding FVIII or FIX. The invention also provides nucleic acid constructs which include as part of their sequence the modified nucleic acid encoding FVIII or FIX. For example, the invention includes plasmids and/or other vectors that include the modified FVIII or FIX sequence along with other elements, such as regulatory elements. Further, the invention provides packaged gene delivery vehicle, such as a viral capsid, including the modified FVIII or FIX sequence. The invention also includes methods of expressing FVIII or FIX by delivering the modified sequence into a cell along with elements required to promote expression in the cell. The invention also provides gene therapy methods in which the modified FVIII or FIX sequence is administered to a subject, e.g., as a component of a vector and/or packaged as a component of a viral gene delivery vehicle. Treatment may, for example, be effected to enhance clotting in a subject and/or to treat a FVIII or FIX deficiency in the subject. Each of these aspects of the invention is discussed further in the ensuing sections.

Modified Nucleic Acid for Expression of FVIII or FIX

The invention provides a modified sequence encoding FVIII or FIX. The modified sequence includes the native FVIII or FIX sequence including one or more optimizing modifications. Examples of optimizing modifications include elimination of one or more cis-acting motifs and introduction of one or more Kozak sequences. In one embodiment, one or more cis-acting motifs are eliminated and one or more Kozak sequences are introduced.

Examples of cis acting motifs that may be eliminated include internal TATA-boxes; chi-sites; ribosomal entry sites; AT-rich and/or GC-rich sequence stretches; ARE, INS, and/or CRS sequence elements; repeat sequences and/or RNA secondary structures; (cryptic) splice donor and/or acceptor sites, branch points; and SalI. Preferably, GC content is enhanced relative to wild-type Factor FVIII or FIX and one or more cis-acting motifs are removed. The GC content is preferably at least 30 to 90% greater than the wild type gene. Additionally, the codon adaptation index is preferably >75, >80, >85, >90, or >95.

The modified FVIII or FIX sequence may also include flanking restriction sites to facilitate subcloning into expression vector.

The invention also includes fragments of the sequence of SEQ ID NO 7 which encode a functionally active fragment FIX. Further, the invention includes modified versions of SEQ ID NO: 7, which encode an analogue of FIX having FIX clotting activity. Additionally, the present application includes modified sequences for FVIII including SEQ ID NOs: 12 and 15.

The invention includes a nucleic acid vector including the modified FVIII or FIX sequence and various regulatory elements. The precise nature of regulatory elements useful for gene expression will vary from organism to organism. In general, they include a promoter which directs the initiation of RNA transcription in the cell of interest. The promoter may be constitutive or regulated. Constitutive promoters are those which cause an operably linked gene to be expressed essentially at all times. Regulated promoters are those which can be activated or deactivated. Regulated promoters include inducible promoters, which are usually "off" but which may be induced to turn "on," and "repressible" promoters, which are usually "on" but may be turned "off." Many different regulators are known, including temperature, hormones, cytokines, heavy metals and regulatory proteins. The distinctions are not absolute; a constitutive promoter may often be regulated to some degree. In some cases an endogenous pathway may be utilized to provide regulation of the transgene expression, e.g., using a promoter that is naturally downregulated when the pathological condition improves.

Examples of suitable promoters include adenoviral promoters, such as the adenoviral major late promoter; heterologous promoters, such as the cytomegalovirus (CMV) promoter; the respiratory syncytial virus promoter; the Rous Sarcoma Virus (RSV) promoter; the albumin promoter; inducible promoters, such as the Mouse Mammary Tumor Virus (MMTV) promoter; the metallothionein promoter; heat shock promoters; the α-1-antitrypsin promoter; the hepatitis B surface antigen promoter; the transferrin promoter; the apolipoprotein A-1 promoter; human FVIII promoters; and human FIX promoters. The promoter may be a tissue-specific promoter, such as the mouse albumin promoter, which is active in liver cells as well as the transthyretin promoter (TTR).

Packaged Modified FVIII or FIX Sequence

The modified FVIII or FIX sequence may also be provided as a component of a packaged viral vector. In general, packaged viral vectors include a viral vector packaged in a capsid. Viral vectors and viral capsids are discussed in the ensuing sections.

Viral Vector

The viral vector component of the packaged viral vectors produced according to the methods of the invention includes at least one modified FVIII or FIX sequence and associated expression control sequences for controlling expression of the modified FVIII or FIX sequence. The viral vector may include cis-acting functions sufficient to enable persistence as episomal forms or by mechanisms including integration of the modified FVIII or FIX sequence into the genome of a target cell.

In a preferred embodiment, the viral vector includes a portion of a parvovirus genome, such as an AAV genome with rep and cap deleted and replaced by the modified hFVIII or hFIX sequence and its associated expression control sequences. The modified FVIII or FIX sequence is typically inserted adjacent to one or two (i.e., flanked by) AAV TRs or TR elements adequate for viral replication; Xiao et al., J Virol 71; 2: 941-948 (1997), in place of the viral rep and cap ORFs. Other regulatory sequences suitable for use in facilitating tissue-specific expression of the modified hFVIII or hFIX sequence in the target cell may also be included.

The viral vector may be any suitable nucleic acid construct, such as a DNA or RNA construct and may be single stranded, double stranded, or duplexed.

Viral Capsid

The viral capsid component of the packaged viral vectors may be a parvovirus capsid. AAV Cap and chimeric capsids are preferred. Examples of suitable parvovirus viral capsid components are capsid components from the family Parvoviridae, such as an autonomous parvovirus or a Dependovirus. For example, the viral capsid may be an AAV capsid (e.g., AAV1, AAV2, AAV3, AAV4, AAV5, AAV6, AAV7, AAV8 AAV 9, AAV10, AAV11 or AAV12 capsid; one skilled in the art would know there are likely other variants not yet identified that perform the same or similar function), or may include components from two or more AAV capsids. A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

One or more of the AAV Cap proteins may be a chimeric protein, including amino acid sequences AAV Caps from two or more viruses, preferably two or more AAVs, as described in Rabinowitz et al., U.S. Pat. No. 6,491,907, entitled "Recombinant parvovirus vectors and method of making," granted on Dec. 10, 2002, the entire disclosure of which is incorporated herein by reference. For example, the chimeric virus capsid can include an AAV1 Cap protein or subunit and at least one AAV2 Cap or subunit. The chimeric capsid can, for example, include an AAV capsid with one or more B19 Cap subunits, e.g., an AAV Cap protein or subunit can be replaced by a B19 Cap protein or subunit. For example, in a preferred embodiment, the Vp3 subunit of the AAV capsid can be replaced by the Vp2 subunit of B19.

Production of Packaged Viral Vector

The invention includes packaging cells which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Viral Vector Functions

The packaging cells of the invention include viral vector functions, along with packaging and vector functions. The viral vector functions typically include a portion of a parvovirus genome, such as an AAV genome, with rep and cap deleted and replaced by the modified FVIII or FIX sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide. The viral vector may be any suitable nucleic acid construct, such as a DNA or RNA construct and may be single stranded, double stranded, or duplexed.

The viral vector functions may suitably be provided as duplexed vector templates, as described in U.S. Patent Publication No. 2004/0029106 to Samulski et al. (the entire disclosure of which is incorporated herein by reference for its teaching regarding duplexed vectors). Duplexed vectors are dimeric self-complementary (sc) polynucleotides (typically, DNA). For example, the DNA of the duplexed vectors can be selected so as to form a double-stranded hairpin structure due to intrastrand base pairing. Both strands of the duplexed DNA vectors may be packaged within a viral capsid. The duplexed vector provides a function comparable to double-stranded DNA virus vectors and can alleviate the need of the target cell to synthesize complementary DNA to the single-stranded genome normally encapsidated by the virus.

The TR(s) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1-AAV12 and other novel capsids as yet unidentified or from non human primate sources. Capsid components may include components from two or more AAV capsids.

In a more preferred embodiment, one or more of the VP capsid proteins is a chimeric protein, comprising amino acid sequences from two or more viruses, preferably two or more AAVs, as described in Rabinowitz et al., U.S. Pat. No. 6,491,907, entitled "Recombinant parvovirus vectors and method of making," granted on Dec. 10, 2002, the entire disclosure of which is incorporated in its entirety herein by reference.

For example, the chimeric virus capsid can include a capsid region from an adeno-associated virus (AAV) and at least one capsid region from a B19 virus. The chimeric capsid can, for example, include an AAV capsid with one or more B19 capsid subunits, e.g., an AAV capsid subunit can be replaced by a B19 capsid subunit. For example, in a preferred embodiment, the VP1, VP2 or VP3 subunit of the AAV capsid can be replaced by the VP1, VP2 or VP3 subunit of B19. As another example, the chimeric capsid may include an AAV type 2 capsid in which the type 2 VP1 subunit has been replaced by the VP1 subunit from an AAV type 1, 3, 4, 5, or 6 capsid, preferably a type 3, 4, or 5 capsid. Alternatively, the chimeric parvovirus has an AAV type 2 capsid in which the type 2 VP2 subunit has been replaced by the VP2 subunit from an AAV type 1, 3, 4, 5, or 6 capsid, preferably a type 3, 4, or 5 capsid. Likewise, chimeric parvoviruses in which the VP3 subunit from an AAV type 1, 3, 4, 5 or 6 (more preferably, type 3, 4 or 5) is substituted for the VP3 subunit of an AAV type 2 capsid are preferred. As a further alternative, chimeric parvoviruses in which two of the AAV type 2 subunits are replaced by the subunits from an AAV of a different serotype (e.g., AAV type 1, 3, 4, 5 or 6) are preferred. In exemplary chimeric parvoviruses according to this embodiment, the VP1 and VP2, or VP1 and VP3, or VP2 and VP3 subunits of an AAV type 2 capsid are replaced by the corresponding subunits of an AAV of a different serotype (e.g., AAV type 1, 3, 4, 5 or 6). Likewise, in other preferred embodiments, the chimeric parvovirus has an AAV type 1, 3, 4, 5 or 6 capsid (preferably the type 2, 3 or 5 capsid) in which one or two subunits have been replaced with those from an AAV of a different serotype, as described above for AAV type 2.

The packaged viral vector generally includes the modified FVIII or FIX sequence and expression control sequences flanked by TR elements sufficient to result in packaging of the vector DNA and subsequent expression of the modified FVIII or FIX sequence in the transduced cell. The viral vector functions may, for example, be supplied to the cell as a component of a plasmid or an amplicon. The viral vector functions may exist extrachromosomally within the cell line and/or may be integrated into the cells' chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

Packaging Functions

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon. The packaging functions may exist extrachromosomally within the packaging cell, but are preferably integrated into the cell's chromosomal DNA. Examples include genes encoding AAV Rep and Cap proteins.

Helper Functions

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1b, E2a, E4, and VA RNA. The packaging functions may be supplied by infection of the packaging cell with the required virus. The packaging functions may be supplied together or separately to the packaging cell using a genetic construct such as a plasmid or an amplicon. The packaging functions may exist extrachromosomally within the packaging cell, but are preferably integrated into the cell's chromosomal DNA.

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Packaging Cell

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRC5, A549, 293 cells, B-50 or any other HeLa cells, HepG2, Saos-2, HuH7, and HT1080 cell lines.

Preferred cell lines for use as packaging cells are insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, NJ (1995); O'Reilly et al., Baculovirus Expression Vectors: A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.* 219:37-44 (1996); Zhao et al., *Vir.* 272:382-93 (2000); and Samulski et al., U.S. Pat. No. 6,204,059.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA.

Treatment Methods

The modified FVIII or FIX gene may be used for gene therapy of FVIII or FIX associated disorders, such as hemophilia A or B. An individual may be in need of gene therapy because, as a result of one or more mutations in the regulatory region and/or the coding sequence of the FVIII or FIX gene, FVIII or FIX is expressed inappropriately, e.g., has an incorrect amino acid sequence, or is expressed in the wrong tissues or at the wrong times, is underexpressed or overexpressed. The modified FVIII or FIX gene may be used as gene therapy to enhance clotting in a subject in need of enhanced clotting.

The target cells of the vectors of the instant invention are cells capable of expressing polypeptides with FVIII or FIX activity, such as those of the hepatic system of a mammal, endothelial cells and other cells with the proper cellular machinery to process the precursor to yield protein with FVIII or FIX activity. In one embodiment, the cells are normal cells cultured in vitro. The target cells may, for example, be human cells, or cells of other mammals, especially nonhuman primates and mammals of the orders Rodenta (mice, rats, rabbit and hamsters), Carnivora (cats and dogs) and Arteriodactyla (cows, pigs, sheep, goats and horses). Any cell type may be targeted. In some cases any cell type except muscle cells may be targeted.

In particular embodiments, the present invention provides a pharmaceutical composition comprising a vector of the present invention including a modified gene of FVIII or FIX in a pharmaceutically-acceptable carrier and/or other medicinal agents, pharmaceutical agents, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

Exemplary pharmaceutically acceptable carriers include sterile, pyrogen-free water and sterile, pyrogen-free, phosphate buffered saline. Physiologically-acceptable carriers include pharmaceutically-acceptable carriers. Pharmaceutically acceptable carriers are those which are that is not biologically or otherwise undesirable, i.e., the material may be administered to a subject without causing undesirable biological effects which outweigh the advantageous biological effects of the material.

A pharmaceutical composition may be used, for example, in transfection of a cell ex vivo or in administering a viral vector or cell directly to a subject.

Recombinant virus vectors comprising the modified gene of FVIII or FIX are preferably administered to the cell in a biologically-effective amount. If the virus vector is administered to a cell in vivo (e.g., the virus is administered to a subject as described below), a biologically-effective amount of the virus vector is an amount that is sufficient to result in transduction and expression of the transgene in a target cell.

The cells transduced with a viral vector are preferably administered to the subject in a "therapeutically-effective amount" in combination with a pharmaceutical carrier. Those skilled in the art will appreciate that the therapeutic effects need not be complete or curative, as long as some benefit is provided to the subject.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^8$ cells, will be administered per dose. Preferably, the cells will be administered in a therapeutically-effective amount.

A further aspect of the invention is a method of treating subjects in vivo with the vector containing modified genes. Administration of the vector to a human subject or an animal in need thereof can be by any means known in the art for administering virus vectors.

Exemplary modes of administration include rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In other preferred embodiments, the inventive vector comprising the modified FVIII or FIX gene is administered intramuscularly, more preferably by intramuscular injection or by local administration. The vectors disclosed herein may be administered to the lungs of a subject by any suitable means, but are preferably administered by administering an aerosol suspension of respirable particles comprised of the inventive parvovirus vectors, which the subject inhales. The respirable particles may be liquid or solid. Aerosols of liquid particles comprising the inventive parvovirus vectors may be produced by any suitable means, such as with a pressure-driven aerosol nebulizer or an ultrasonic nebulizer, as is known to those of skill in the art. See, e.g., U.S. Pat. No. 4,501,729.

Dosages of the inventive virus vector with the modified FVIII or FIX gene will depend upon the mode of administration, the disease or condition to be treated, the individual subject's condition, the particular viral vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units.

The modified FVIII or FIX genes may be administered as components of a DNA molecule having regulatory elements appropriate for expression in the target cells. The modified FVIII or FIX genes may be administered as components of viral plasmids, such as rAAV vectors. Viral particles may be administered as viral particles alone, whether as an in vivo direct delivery to the portal vasculature or as an ex vivo treatment comprising administering the vector viral particles in vitro to cells from the animal receiving treatment followed by introduction of the transduced cells back into the donor.

EXAMPLES

The results of this rodent feasibility study confirm the superiority of both double stranded vectors and liver mediated FIX gene therapy at doses 10 to 100 fold below those established to be safe in human clinical trial using AAV2.

AAV2 and BNP2.5 Infect Primary Human Skeletal Muscle

FIG. 1 shows in vitro GFP transduction $1 \times 10^9$ vg HPMC 530,000 cells using the different vectors including the AAV2 and chimeric virus vector BNP2.5 having the sequence set forth in SEQ ID NO. 17. Primary human skeletal muscle cell were tested by immunofluorescence for vWF/Factor IX, smooth muscle alpha-actin, and sarcomeric myosin to ensure purity (i.e. neg., neg., & positive respectively). Only cells that were negative for bacteria, fungi, *mycoplasm*, HIV DNA, and Hepatitis B & C DNA were considered for vector transduction. These cells were established in trans-well tissue culture conditions after second passage isolation to promote well-differentiated striated muscle. 60 to 80% confluent monolayers were infected using dose escalation from MOI of 1 to 100/cell (total $1 \times 10^4$) and GFP reporter transgene (FIG. 1).

Figure 2:
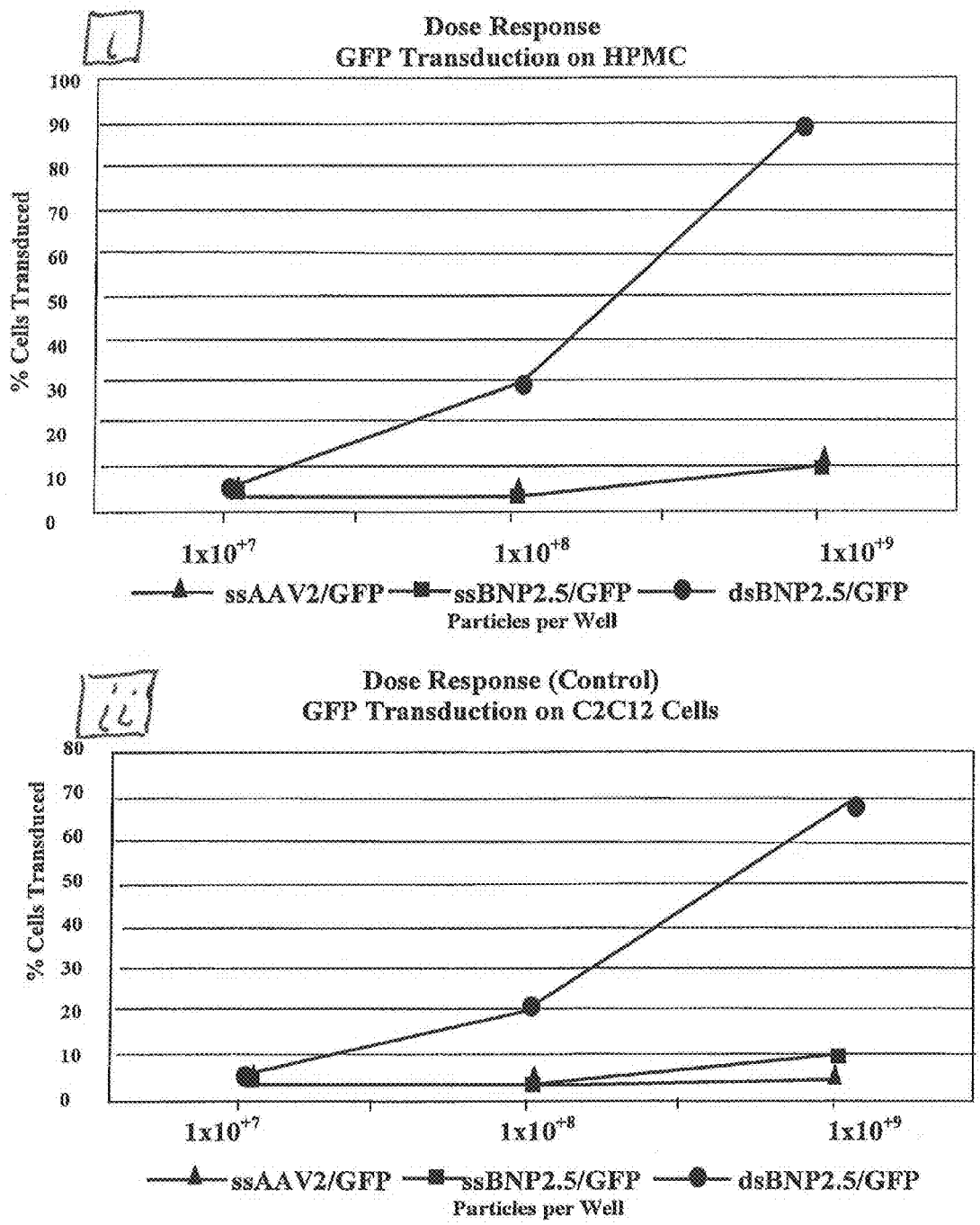
FIG. 2 i and ii shows in vitro GFP does response of single and double stranded genome.

FIG. 2 shows in vitro GFP dose response single vs. double stranded genome. Cells were monitored over time and percent positive tabulated compared to control. These GFP results are compared to primary mouse skeletal cells transduced under identical conditions as a positive control. Positive transduction indicated here (FIG. 2) shows that human skeletal muscle cells are permissive to vector infection.

Vector Expressed Transgene Secretes from Primary Human Skeletal Muscle

Key to these studies is the ability to determine if human FIX transgene can be secreted from primary human skeletal muscle. Two methods have been employed to determine if human FIX transgene is successfully secreted from target cells after vector administration. ELISA was used to determine the total amount of FIX antigen, and activated partial thromboplastin time (APTT) to determine functional activity. In transformed tissue culture cells, peak FIX expression was determined to occur 24 hours after vector transduction. Cell media was removed and analyzed for FIX every 24 hours until transgene expression plateau.

Figure 3:
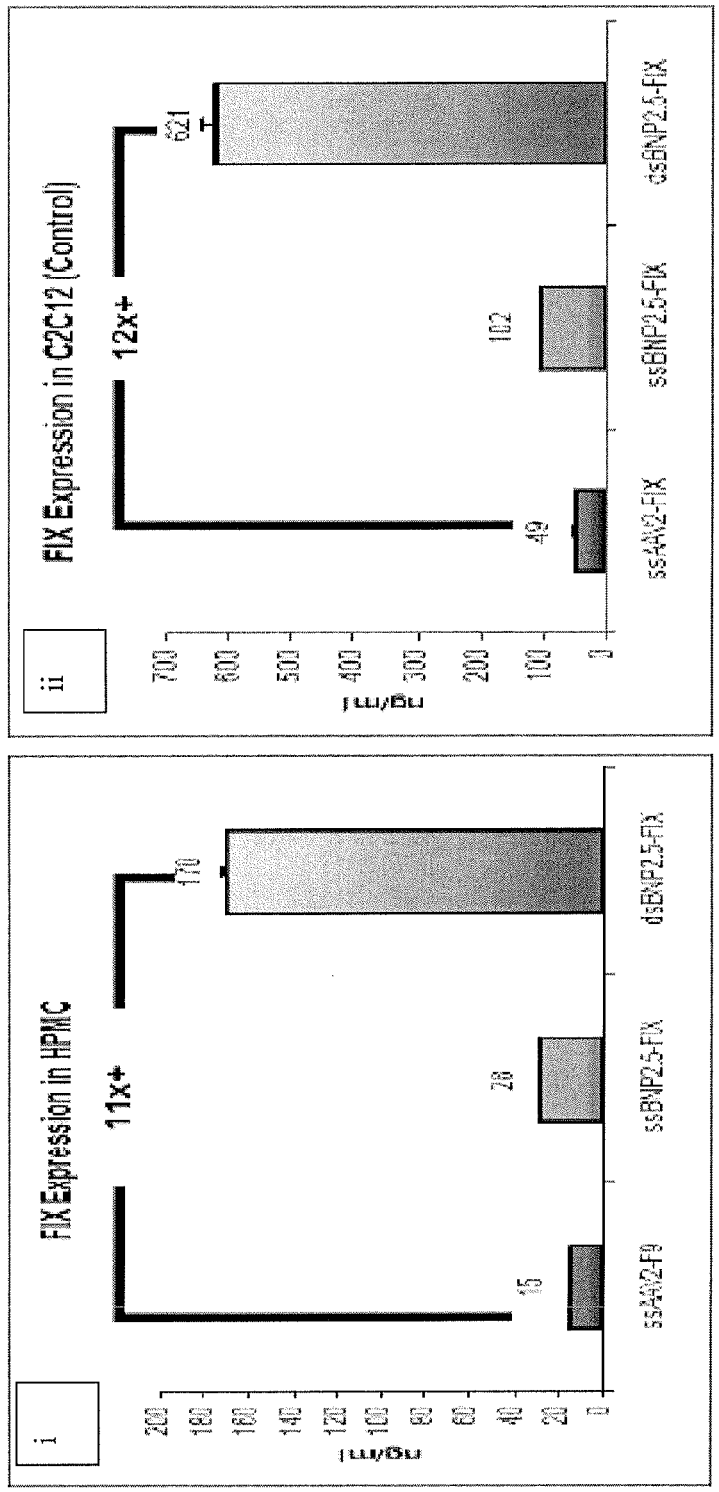
FIG. 3 i and ii shows the level of expression from primary and human primary skeletal muscle cell line.
Figure 4:
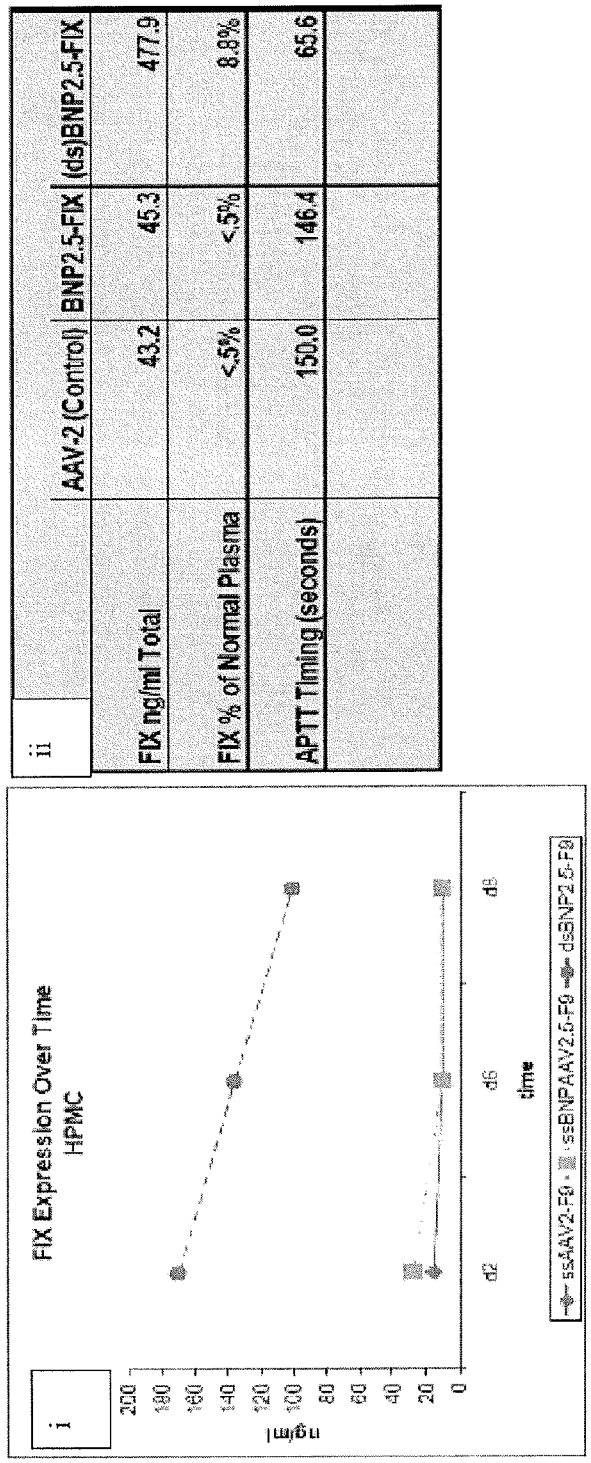
FIG. 4 i and ii shows APTT HPMC in vitro lysate from $1 \times 10^9$ vg/titer infection 24 hours post infection.

The levels of expression from primary mouse and human primary skeletal muscle cell line supernatant were compared (FIG. 3) and the functional activity of the transgene was measured. (FIG. 4). These positive results support a conclusion that human skeletal muscle can secrete vector derived FIX transgene.

FIG. 4 shows APTT HPMC in vitro lysate from $1 \times 10^9$ vg/titer infection 24 hours post infection. BNP2.5 expresses 2 fold higher levels of secreted FIX from primary human skeletal muscle.

Figure 5:
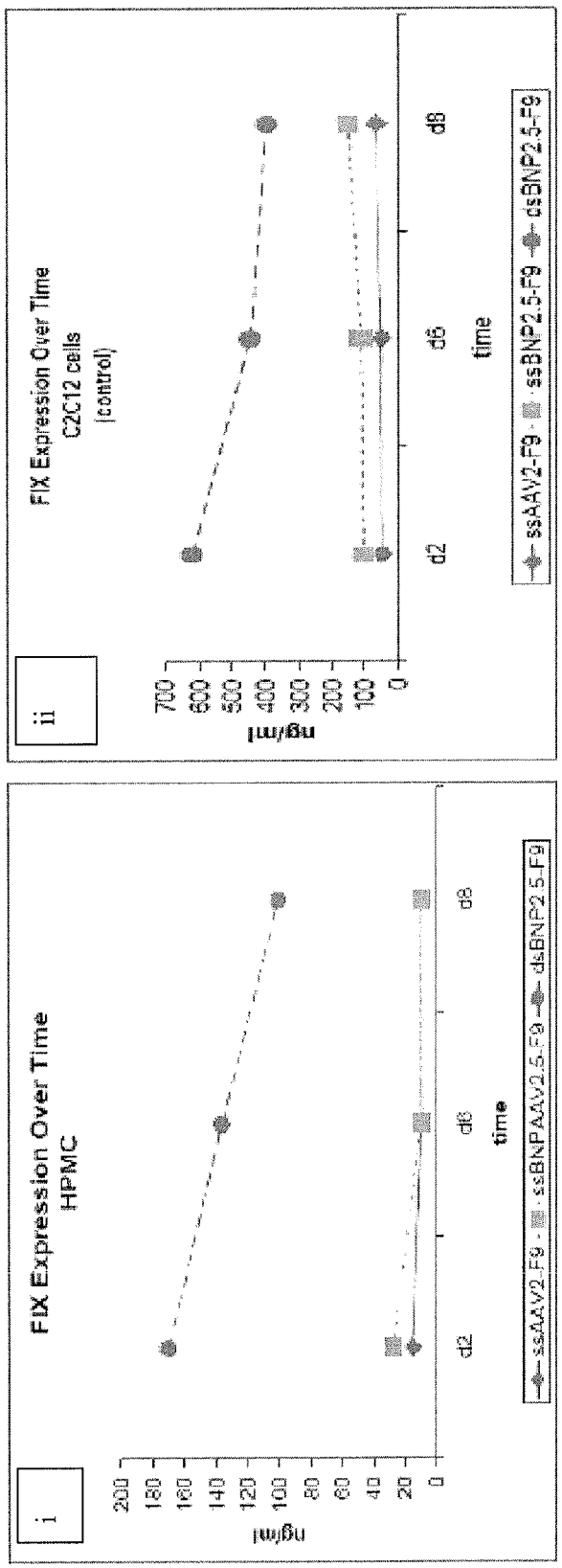
FIG. 5 i and ii shows hFIX in vitro HPMC cell lysate expression.

FIG. 5 shows hFIX in vitro HPMC cell lysate expression. BNP2.5 was evaluated with ELISA every 24 hours tested for increased expression of human FIX transgene from human skeletal muscle after vector transduction (FIG. 5) as described above. These positive results show that human skeletal muscle can secrete vector derived FIX transgene and that BNP2.5 is more efficient than AAV2 in both human and mouse primary cells.

AAV2 vs. BNPdsFIX in Hemophilic Mouse Model R333Q for Level and Duration of Transgene Expression Recent development of hemophilia B knockout mouse models (FIXKO mouse) has reproduced the bleeding phenotype of human hemophilia B, but because these models produce no FIX, they fail to reproduce the dominant human phenotype. In addition, treatment of these models with vectors expressing FIX transgene typically results in development of antibodies making long-term efficacy studies impossible. Recent development of human FIX mouse model R333Q-hFIX at the University of North Carolina at Chapel Hill has resulted in a model that mimics mutation observed in humans (mis-sense mutation). These animals express mRNA transcripts and circulating human FIX detectable throughout development, but with FIX activity less than 1%. R333Q mutation was chosen because data has been reported on several patients with severe hemophilia B who exhibit this mutation. Moreover, these CRM+ patients have nearly normal levels of FIX antigen and their clotting activity is usually less than 1%. The R333Q-hFIX mice are not morphologically different from wild-type mice. They survive well if no injury occurs and have litters of 4-8 pups with a sex ratio of approximately 1:1. These animals display identical bleeding phenotype to that observed in humans, making them ideal models for studying gene therapy approaches for hemophilia B deficiency. In addition human FIX R333Q gene was expressed as the alanine form of the Ala 148 Thr dimorphism. Because A-1 antibody binds well to the FIX with the threonine at residue 148 and weakly to the alanine isoform, vectors expressing the threonine isoform can readily be detected.

Animals 8-10 weeks of age have been used for this study (FIG. 6), in which three vector doses have been tested. R333Q mice (n=5/cohort) and normal parent animals C57BL6 have been injected IM with AAV2 and BNP2.5ds expressing hFIX (FIG. 6). A cohort of BNP2.5(ss)-FIX-CMV has been added to the design to evaluate vector capsid tropism significance. Levels of FIX protein expression and transgene activity were measured over time as described by Jin et. al., Blood 2004. Measurements of time points every two weeks after vector administration were carried out past six weeks. APTT assay has been utilized to determine activity of vector delivered transgene and compared to control. Lack of antibody formation as indicated by Bethesda inhibition assay has been carried out on a sub-set of animals.

Figure 6A:
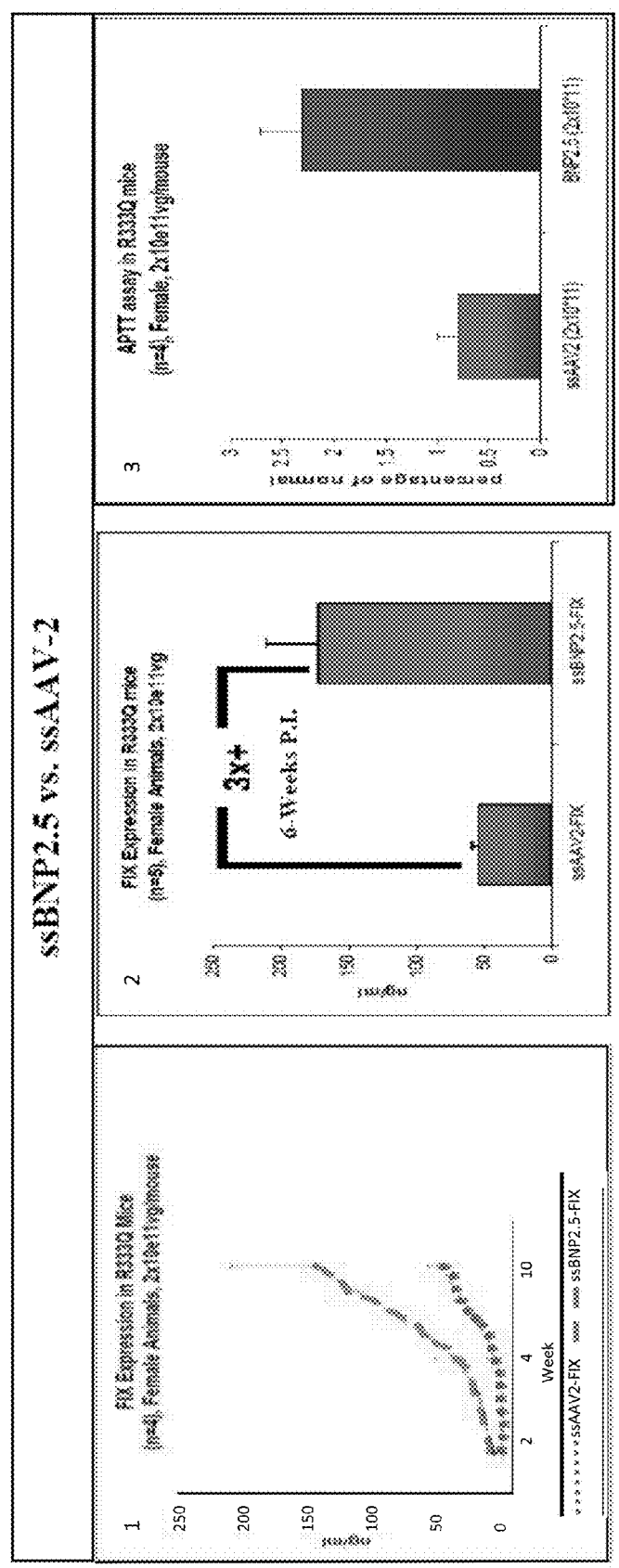
FIG. 6 shows FIX in vivo data from R333Q model 6 weeks post injection for ssBNP2.5 vs. ssAAV2 (6A (1, 2, and 3)) and dsBNP2.5 vs. ssAAV2 (6B (4, 5, and 6)).
Figure 6B:
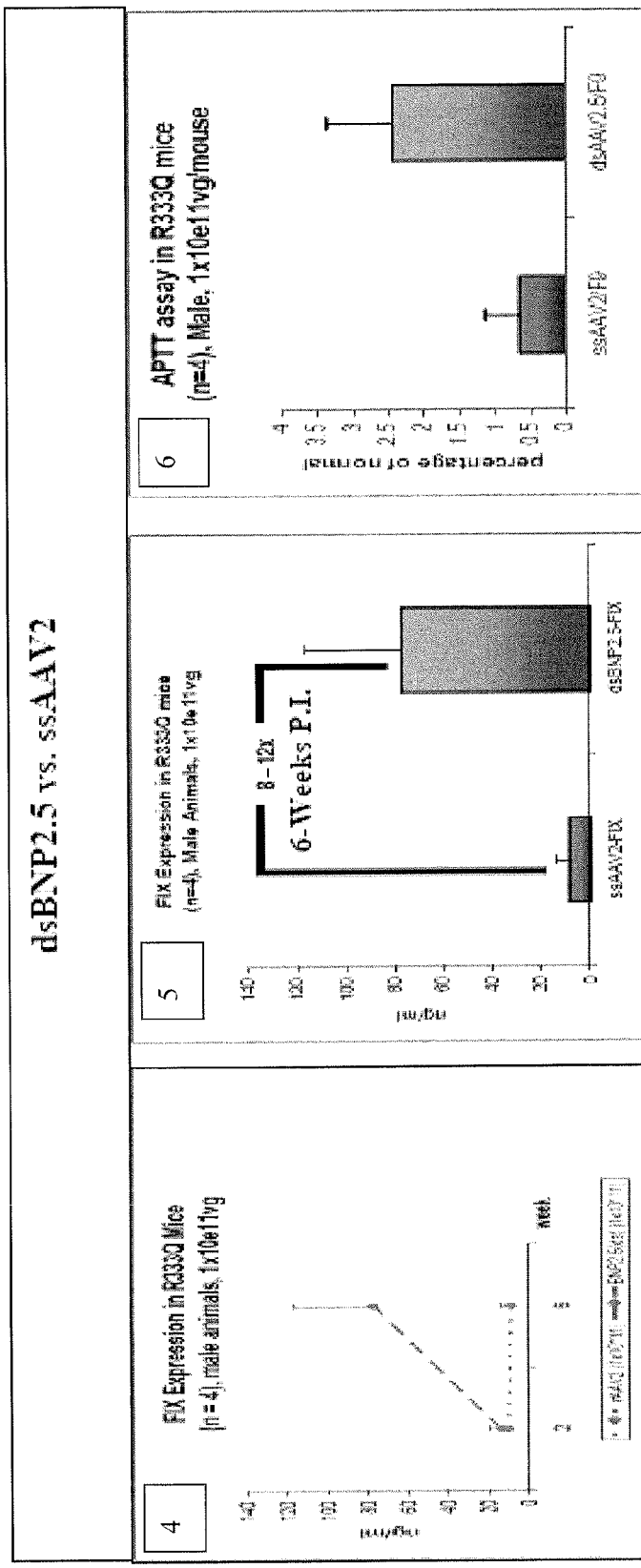

FIG. 6 shows FIX expression in vivo data from R333Q model 6 weeks post injection for ssBNP2.5 vs. ssAAV2 (FIG. 6A (1, 2, and 3)) and dsBNP2.5 vs. ssAAV2 (FIG. 6B (1, 2, and 3)).

Determining BNP FIX Performance after Liver Transduction

Figure 7:
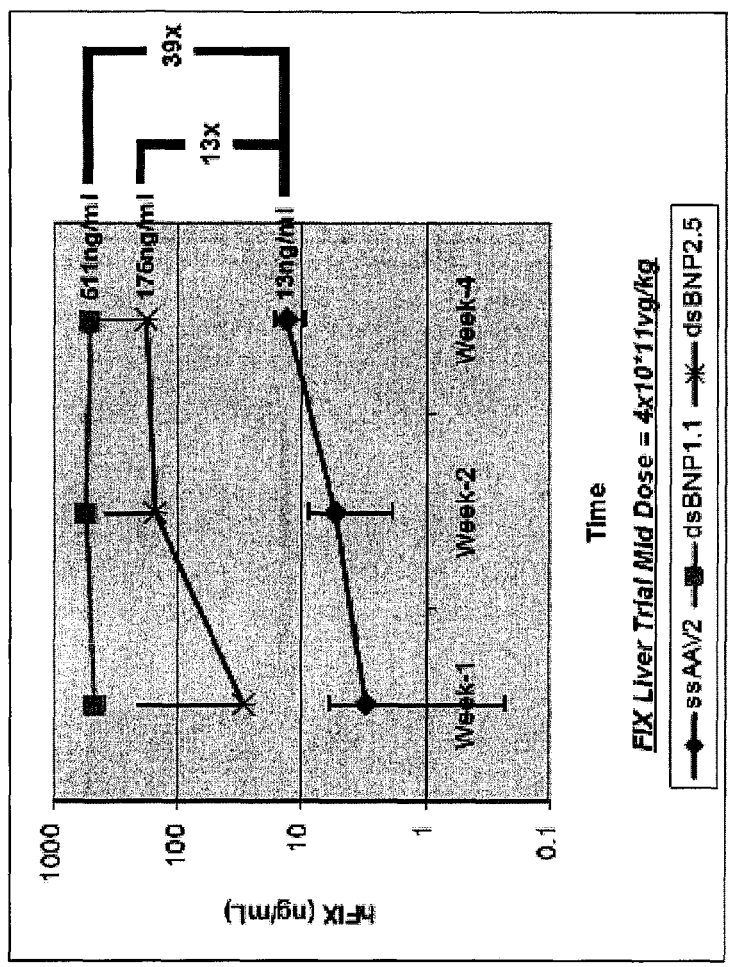
FIG. 7 shows the results of Portal vein administration in C57Blk6 using ssAAV2, dsBNP-1.1 and ds BNP 2.5 carrying the FIX transgene.

Although the original primary focus of this feasibility study was to determine BNP transduction in skeletal muscle for FIX expression, similar Phase I clinical studies showing AAV2 transduction in liver have yielded provocative results. AAV2 vector is safe at doses ranging from $8 \times 10^{10}$ to $4 \times 10^{11}$/kg but without therapeutic levels of transgene expression. Therapeutic levels of FIX can be obtained at $2 \times 10^{12}$/kg, but FIX transgene expression is transient (4 wk). While no formal understanding was obtained for the transient levels of FIX protein in transduce liver, speculation implicates that high vector dose may provoke immune response to transduce liver cells, supporting a conclusion that the invention provides a safe dose of FIX gene transfer ($10^{10}$ or $10^{11}$ dose) that is also efficacious (10-15% levels of FIX) by using AAV vectors using double stranded vector templates (FIG. 7). Mouse studies were carried out using BNP in vivo w/C57Bl6 mice. These experiments employed 3 cohorts with 4 animals/cohort; testing (ss)AAV2, (ds)BNP-1.1 and (ds)BNP-2.5 carrying FIX transgene, administered to the liver via portal vein administration and monitored for FIX levels to beyond four weeks. The data derived from these experiments points to a conclusion that (i) (ds)BNP is significantly more efficient compared to traditional ssAAV2 vector, (ii) hepatic efficiency in vector transduction and FIX expression is significantly improved over muscle (both primary human myoblasts in culture and R333Q in vivo results), (iii) and these novel reagents are ideally suited for allowing for an even lower dose than muscle mediated gene transfer of FIX to reach similar protein expression levels.

Additional Liver Data (Optimized Transgene)

Figure 8:
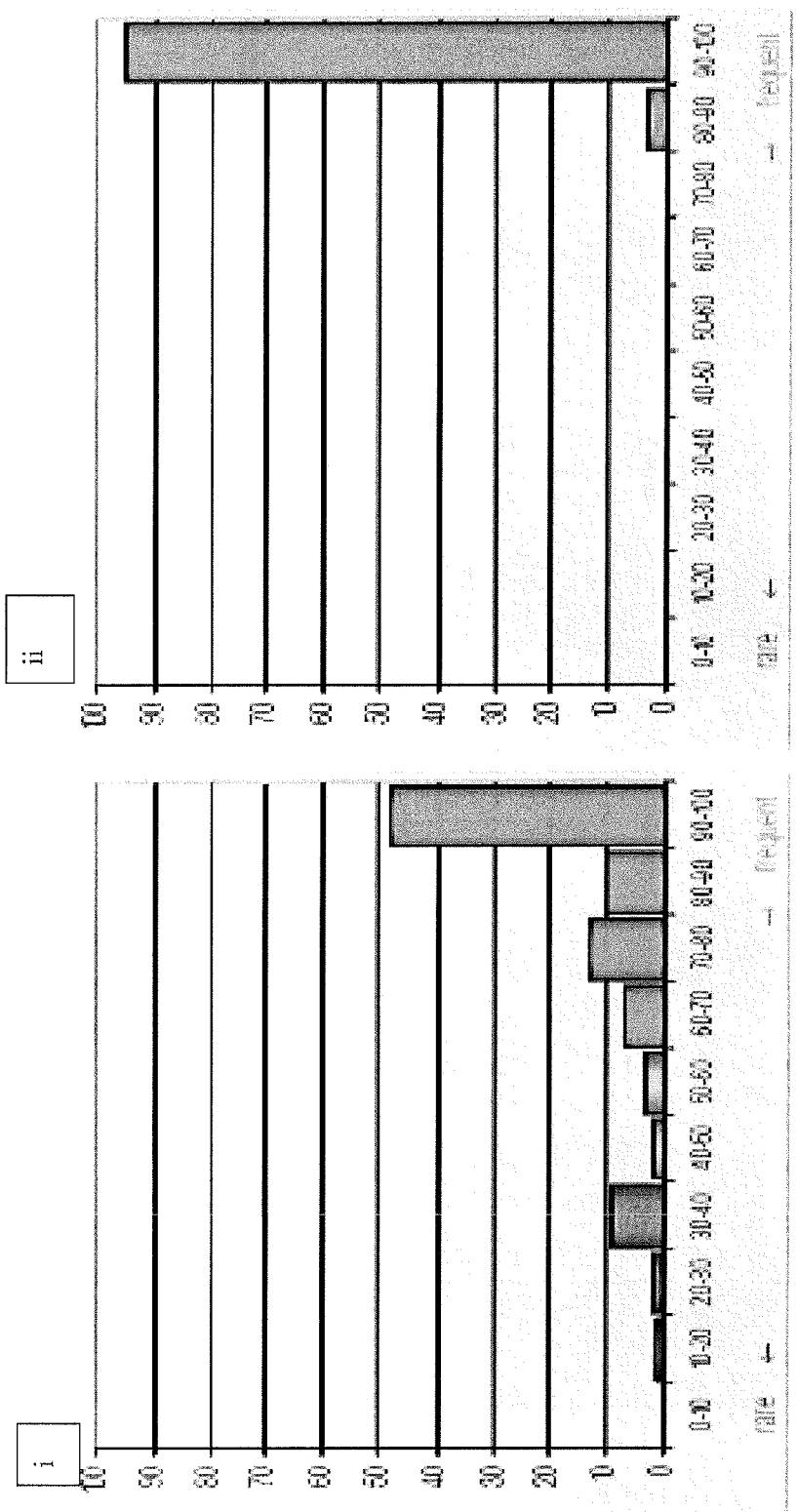
FIG. 8 i and ii shows the codon sequence of an optimized hFIX.

The FIX feasibility liver data in C57Bl6 mice suggests that safe and efficacious doses of double stranded gene transfer administered into the liver may be therapeutic at vector levels previously shown in patients as safe but not expressing sufficient hFIX. To elaborate further upon this point we have completed an additional study, in which we developed and used a transgene codon optimized hFIX. When computer program for optimum codon usage was applied to the "wild type" hFIX gene, we observed a large number of rare codons in the coding sequence (FIG. 8). In addition, hFIX gene contains low GC content (FIG. 9), a feature known to facilitate mRNA turnover. Moreover, several negatively cis-acting motifs were found, which may hamper expression in mammals. As such, a hFIX gene was synthesized in which the codon usage has been revised to more nearly approximate optimum codon bias of mammals (FIG. 8).

Figure 9:
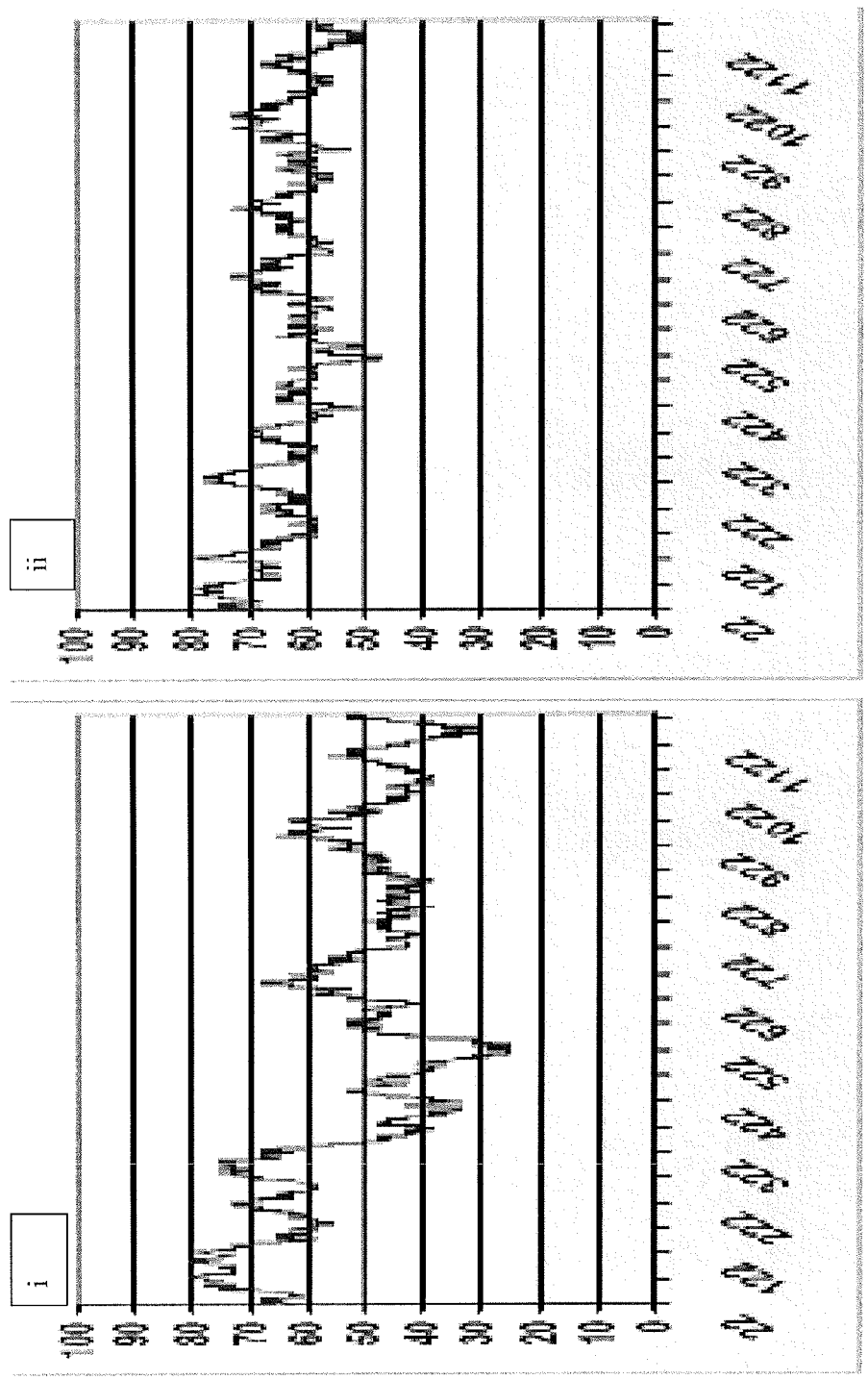
FIG. 9 i and ii shows the in vitro expression of wild-type vs optimized hFIX coding sequence.

Based on computer analysis, we removed negative cis-acting elements (such as splice sites, unwanted poly(A) signals, etc), which may negatively influence protein expression. In addition, the GC-content was increased to prolong mRNA half-life (FIG. 8). Codon usage was adapted to the bias of *Homo sapiens* resulting in a high Codon Adaptation Index (CAI) value. Based on these modifications, we predicted that the optimized gene would allow higher and more stable expression rates in mammalian cells. Using AAV2 carrying optimized vs. wild type hFIX coding sequence, we carried out side-by-side expression analysis in vitro (FIG. 9). Based on these studies it is clear that the optimized FIX gene expresses significantly more protein product/cell when compared to wild type coding sequence when delivered at the same dose.

Figure 10:
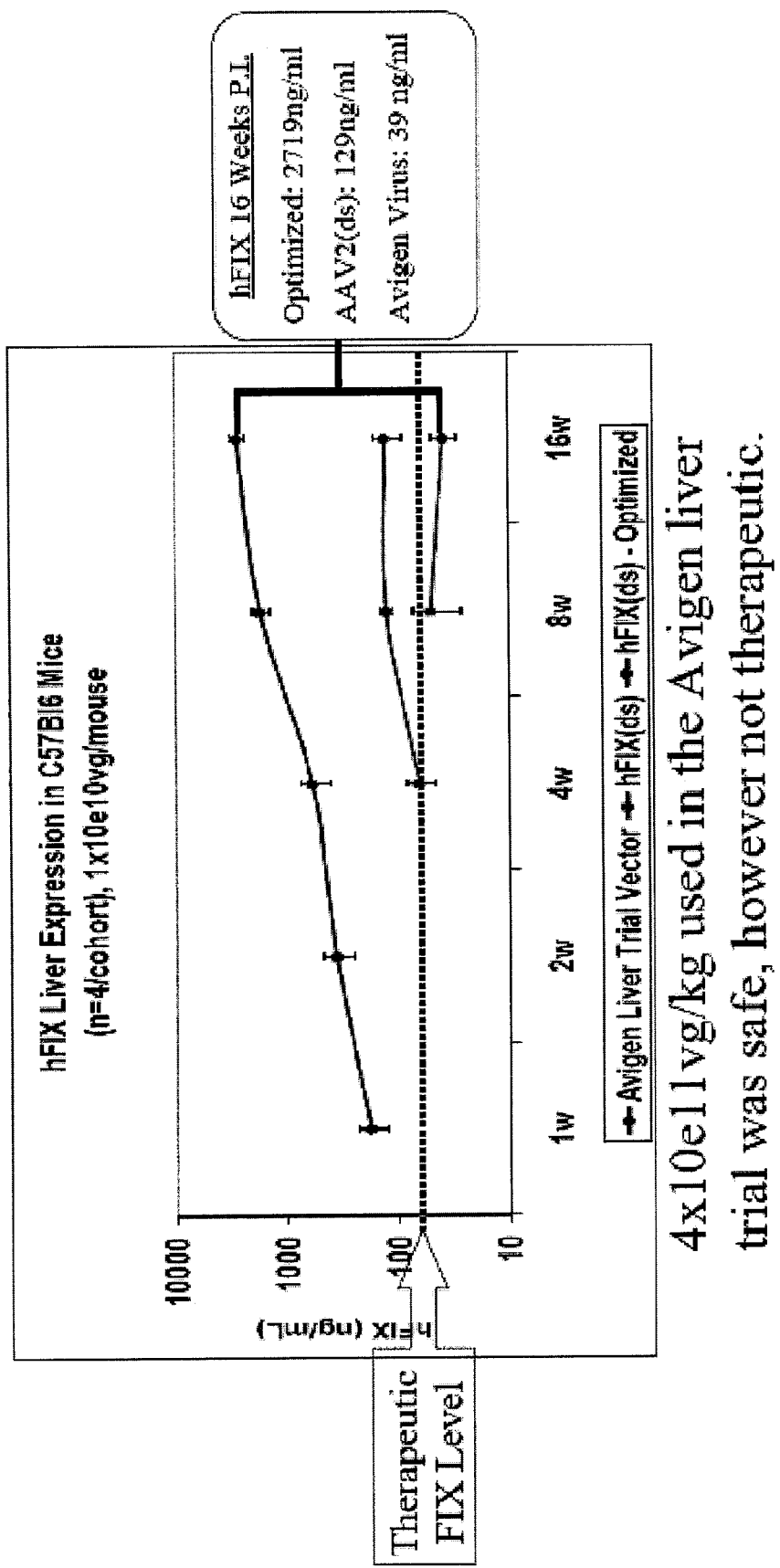
FIG. 10 shows expression of hFIX and comparison of Avigen virus ($4 \times 10^{11}$ vg/kg) vs AAV2 dshFIX and optimized hFIX.
Figure 11:
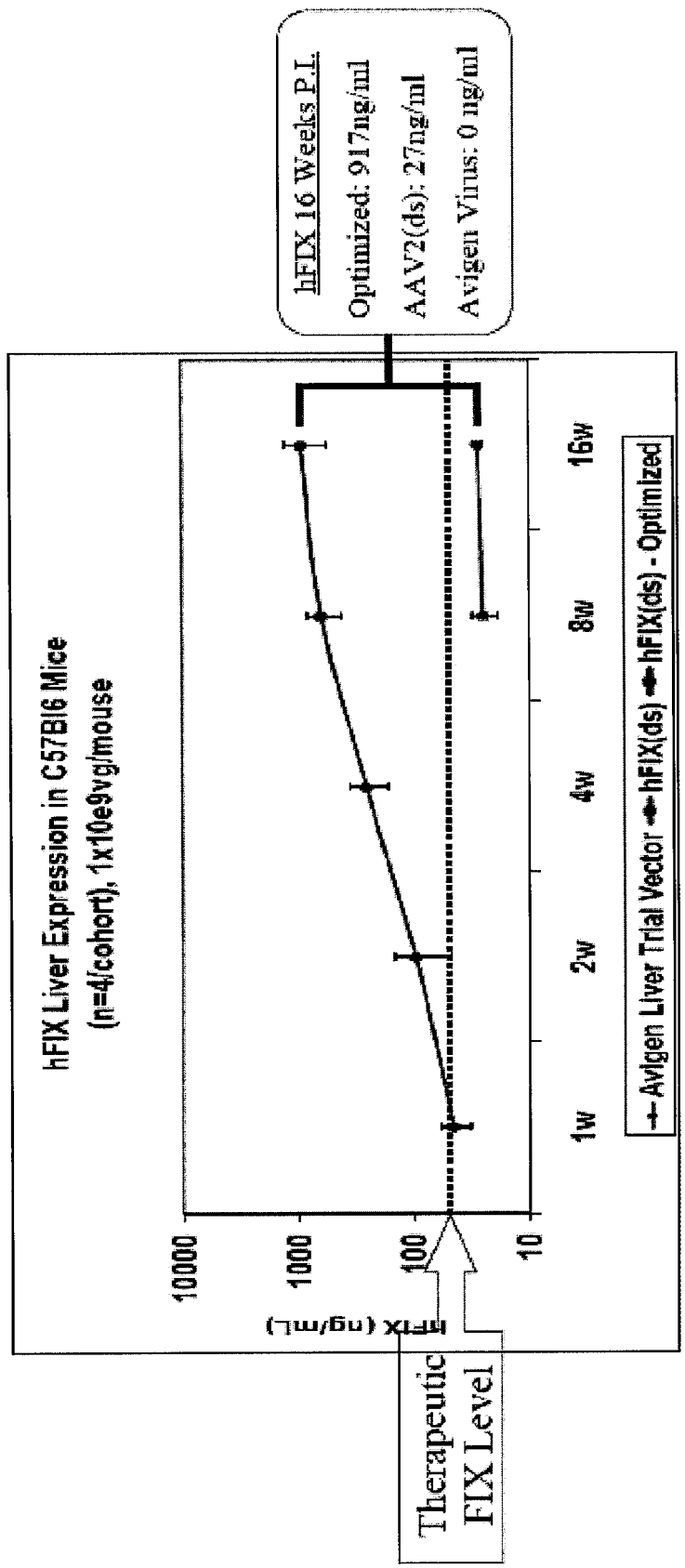
FIG. 11 shows expression of hFIX comparing Avigen virus ($8 \times 10^{10}$ vg/kg) vs AAV2 dshFIX and optimized hFIX.

Upon codon optimization a side by side comparison of in vivo vector expression of the liver mediated AAV2 clinical trial vector vs. double stranded and double stranded+codon optimized transgene cassette in C57BL6 mice. The dose chosen was shown in the clinical trial earlier to be sub-therapeutic but safe ($4 \times 10^{11}$ vg/kg). The animals at 8-10 weeks old received a single portal vein injection (n=4/serotype/dose). When using the clinical trial vector the results mirrored the clinical trial, with the AAV2 vector being sub therapeutic in vivo in all animals. At the same vector dose, AAV2 with a double stranded cassette after 4 weeks post injection expressed therapeutic levels of hFIX and sustained these levels out past 16 weeks, and AAV2 with a double stranded optimized transgene cassette, expressed therapeutic levels from week one through 16 weeks at up to 70 times the hFIX ng/ml compared to the clinical trial vector (FIG. 10, 11).

Immune Response to BNP2.5 in Animals Pre-Exposed to AAV

Since BNP2.5 carries a majority capsid backbone of AAV2 and minority amino acids from AAV1, it was studied to determine whether the immune profile of this chimeric vector is identical to parental donor AAV2, shared between AAV1 & AAV2, or distinct. If the chimeric vector displays a different immune profile than parent vectors, this may suggest that vector administration in patients pre-exposed to AAV 1 or AAV2 is not rate-limiting to BNP vector transduction. If the data suggest that the BNP has an immune profile identical to parent vector, then there is a possibility that pre-exposure to wild type AAV would have an impact on BNP identical to studies established in the literature.

Figure 12:
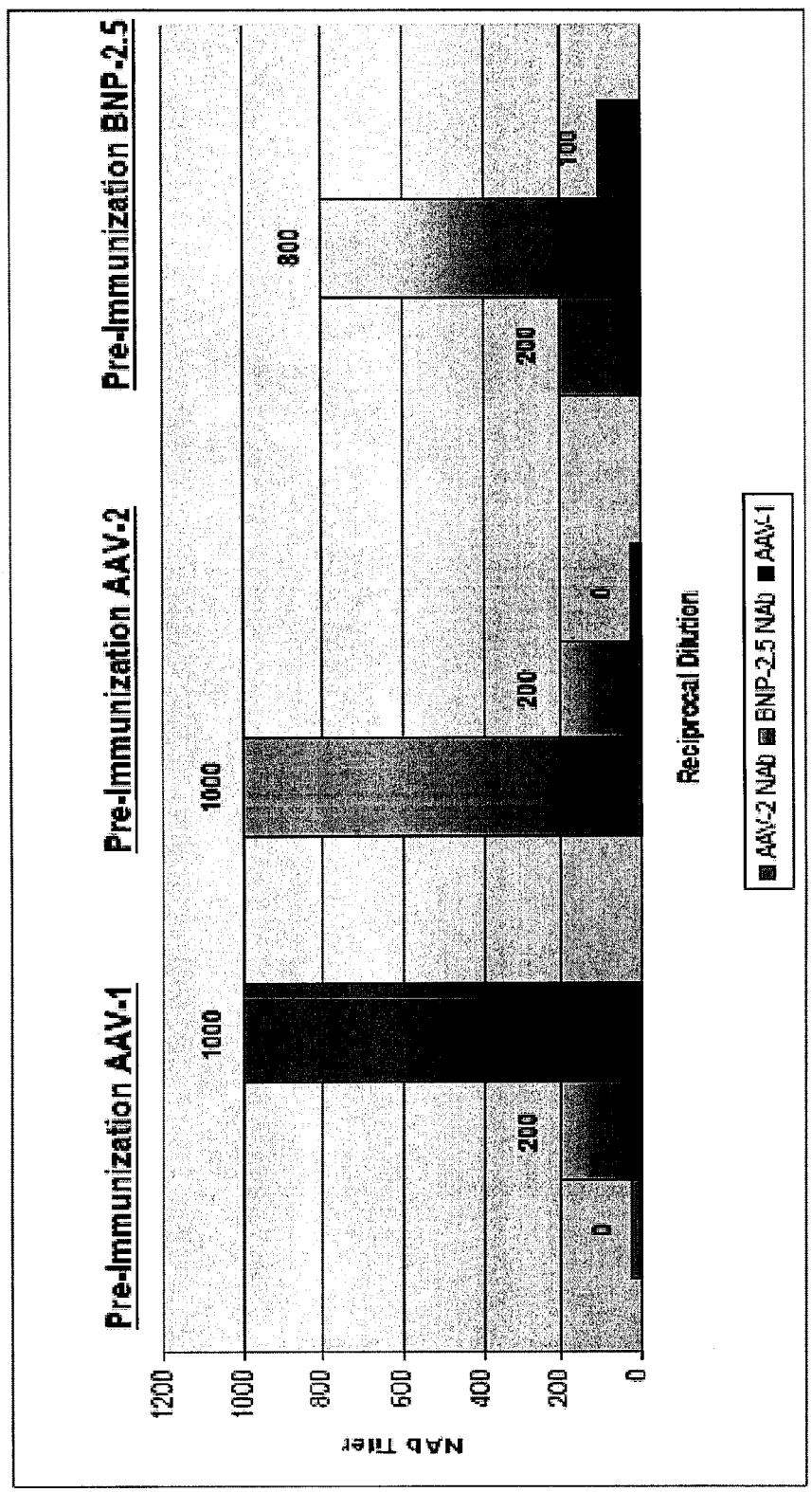
FIG. 12 shows the level of in vitro neutralizing antibody titer using AAV1, AAV2 and BNP-2.5.

These experiments were carried out in vitro and in vivo. In the in vitro experiments, C57Bl6 animals were pre-exposed to AAV1, AAV2, or BNP2.5 vector. Four weeks post IM injection, sera was collected, and 293 cells at a density of $1 \times 10^5$ cells/well in 1 ml DMEM containing 10% FBS were seeded in a 24-well plate. The cells were cultured for 2-3 hrs at 37° C. and allowed to adhere to the well. The medium was removed before $1 \times 10^6$ particles of adenovirus dl309 were added in a final volume of 200 ul/well. The cells were further incubated at 37° C. for 1 hr and then washed twice. AAV-GFP vectors ($1 \times 10^8$ particles) were incubated with human sera at serial dilutions with PBS for 2 hrs at 4° C. in a total volume of 25 µl (12.5 ul serial dilution sera samples plus 12.5 µl of AAV/GFP vectors which contain $1 \times 10^8$ particles). The mixture was added to cells in a final volume of 200 µl and incubated overnight at 37° C. GFP expressing cells were counted under a fluorescent microscope. The percent inhibition was calculated without serum sample as a reference. The neutralizing antibody titer was calculated (FIG. 12) using the highest dilution where the percentage of GFP expressed cells is 50% less than control without sera.

Figure 13:
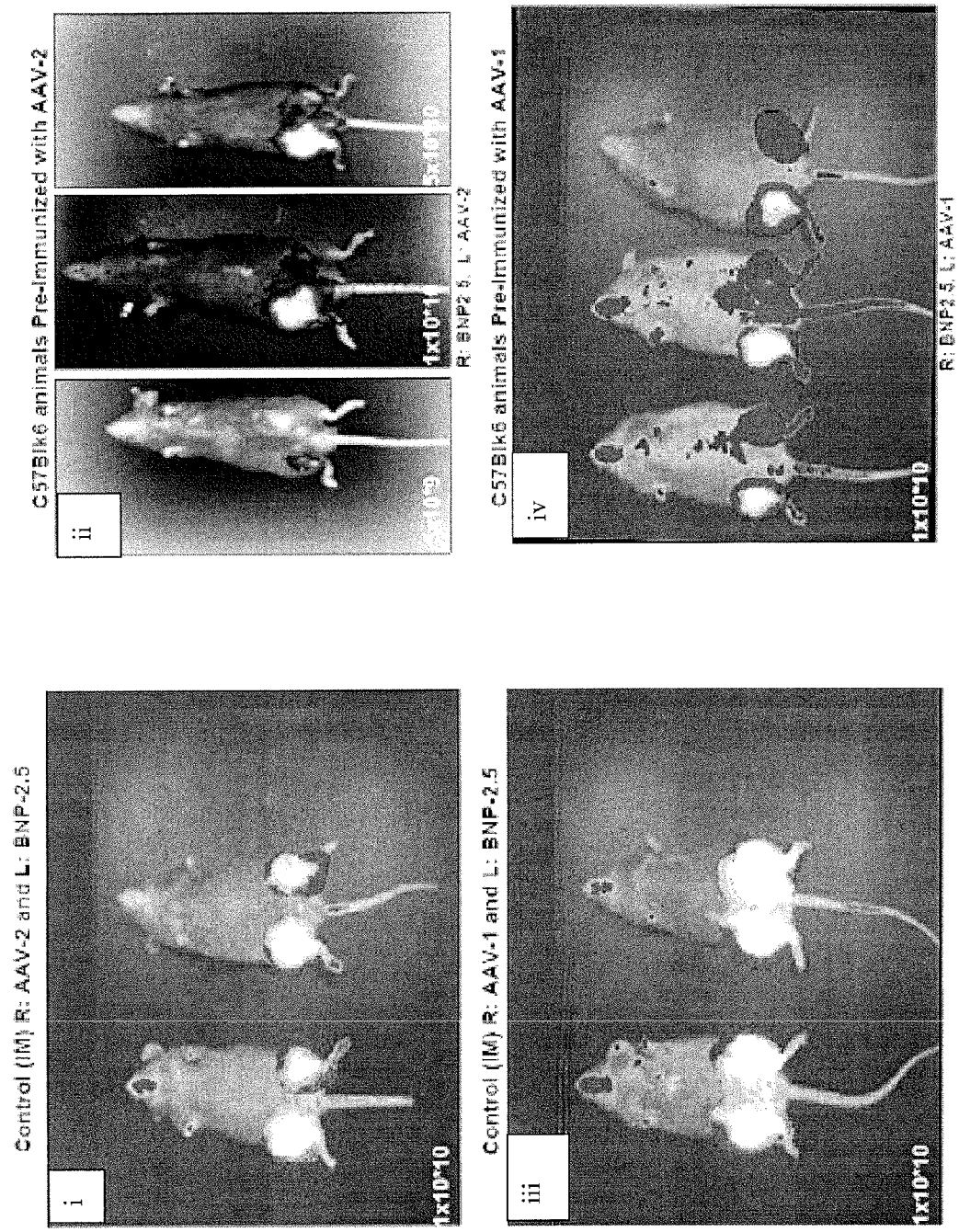
FIG. 13 i, ii, iii and iv shows the level of in vivo neutralizing antibody titer using AAV1, AAV2 and BNP-2.5.
Figure 14:
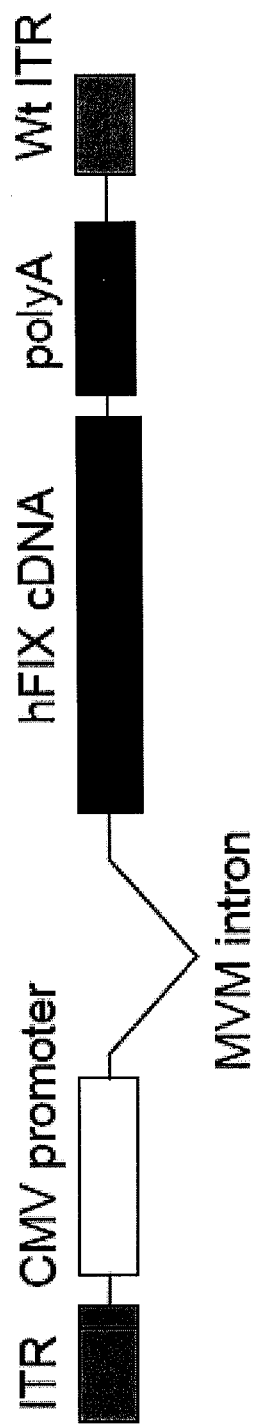
FIG. 14 shows a preferred vector of the present invention.

The in vivo experiments were implemented using the same C57Bl6 mice which have been primed with AAV1, AAV2, and BNP2.5. After four weeks, the mice were challenged with BNP vector IM carrying Luc reporter and carrying the vector as shown in FIG. 14 with the sequence set forth in FIG. 15, and analyzed using real time imaging (FIG. 13). Control experiments of BNP with identical dose in naive animals were used.

Results

After six weeks post administration of an optimized vector dose of $1 \times 10^{11}$ vg/kg, the expression levels indicate a relative translation of FIX expression from tissue culture to in vivo. The rAAV2 provided the baseline and measured the lowest FIX expression. BNP2.5 (ss) and BNP2.5 (ds) both showed improvement over rAAV2, with single stranded measuring a 3-6 fold improvement in FIX and double stranded BNP2.5 deriving an 8-12 fold improvement in circulating FIX (FIG. 6). The work described here shows that the BNP double stranded "BNP(ds)" vector containing a FIX gene can transduce murine and canine striated muscle and hepatic cells resulting in FIX gene expression and protein secretion into the peripheral blood.

Modified codon FVIII (hFVIII) sequences and flanking sequences were developed (SEQ ID NOs: 12 and 15, FIGS. 22 and 23, respectively) using a computer program to synthesize an hFVIII gene in which the codon usage has been revised to more nearly approximate optimum codon bias of mammals, including optimization of GC content and cis-acting motifs.

Based on computer analysis, negative cis-acting elements (such as splice sites, unwanted poly(A) signals, etc) were removed that may negatively influence protein expression. In addition, the GC-content was increased to prolong mRNA half-life. Codon usage was adapted to the bias of *Homo sapiens* resulting in a high Codon Adaptation Index (CAI) value. Based on these modifications, the modified gene would likely allow higher and more stable expression rates in mammalian cells, specifically human cells or human derived cells.

Figure 17:
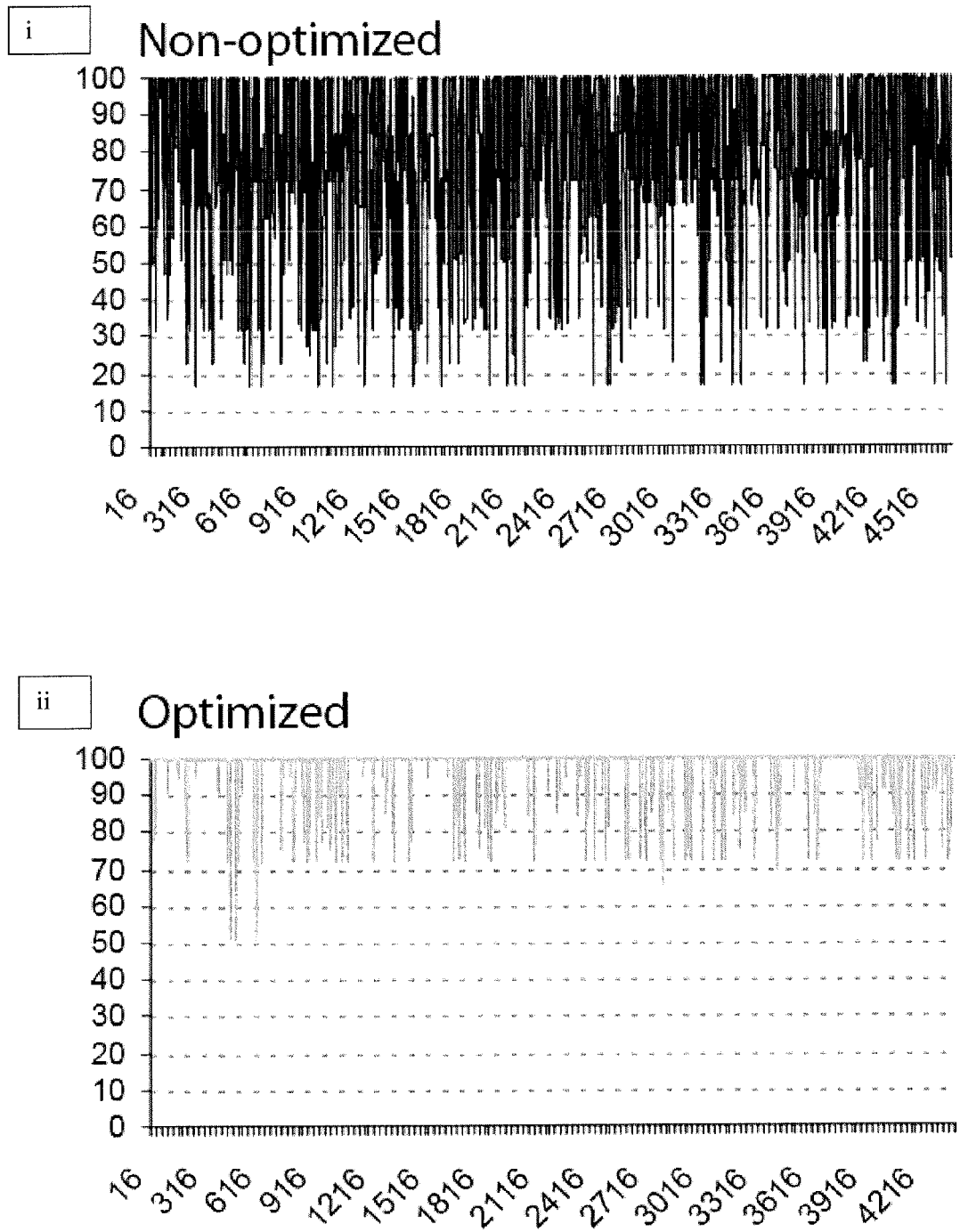
FIG. 17 i and ii shows the enhanced codon quality of SEQ ID NO: 12 relative to the non-optimized (SEQ ID NO: 19).

With respect to SEQ ID NO: 10, the histograms of FIG. 16 show the percentage of sequence codons, which fall into a certain quality class. The quality value of the most often used codon for a given amino acid in the desired expression system is set to 100, the remaining codons are scaled accordingly (See also Sharp, P. M., Li, W. H., Nucleic Acids Res. 15 (3), 1987). FIG. 17 shows a dramatically enhanced codon quality. FIG. 18 shows an increase in GC content from 44% (Wild type gene SEQ ID NO: 19) to 66% for optimized (SEQ ID NO. 12).

Modified motifs include the following:

| Prokaryotic inhibitory motifs | 16 | 0 |
| polyA site | 3 | 0 |
| consensus (cryptic) splice donor site | 2(9) | 0 |
| RNA instability motif (ARE) | 11 | 0 |

Figure 19:
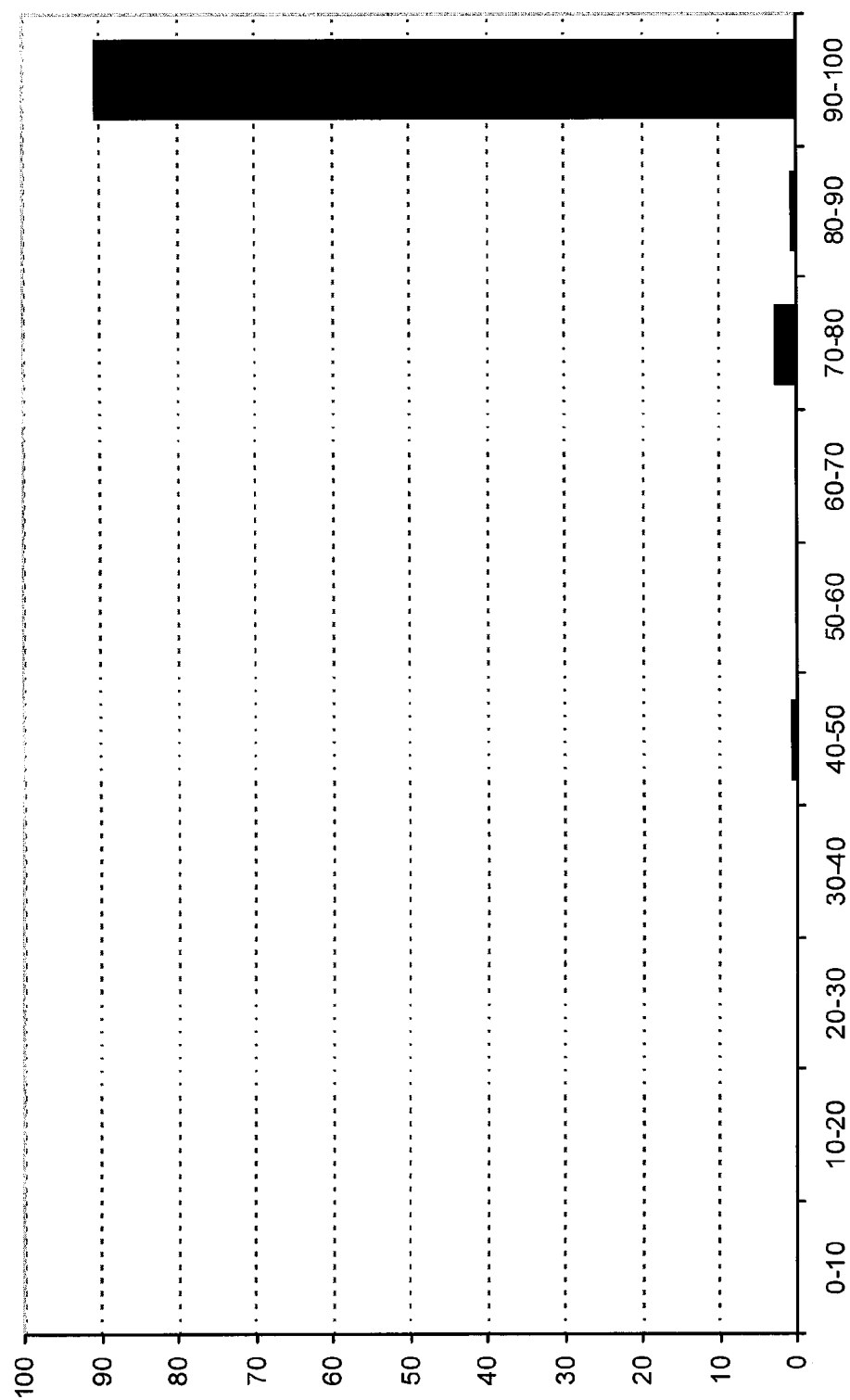
FIG. 19 shows codon quality relative to SEQ ID NO: 15.
Figure 20:
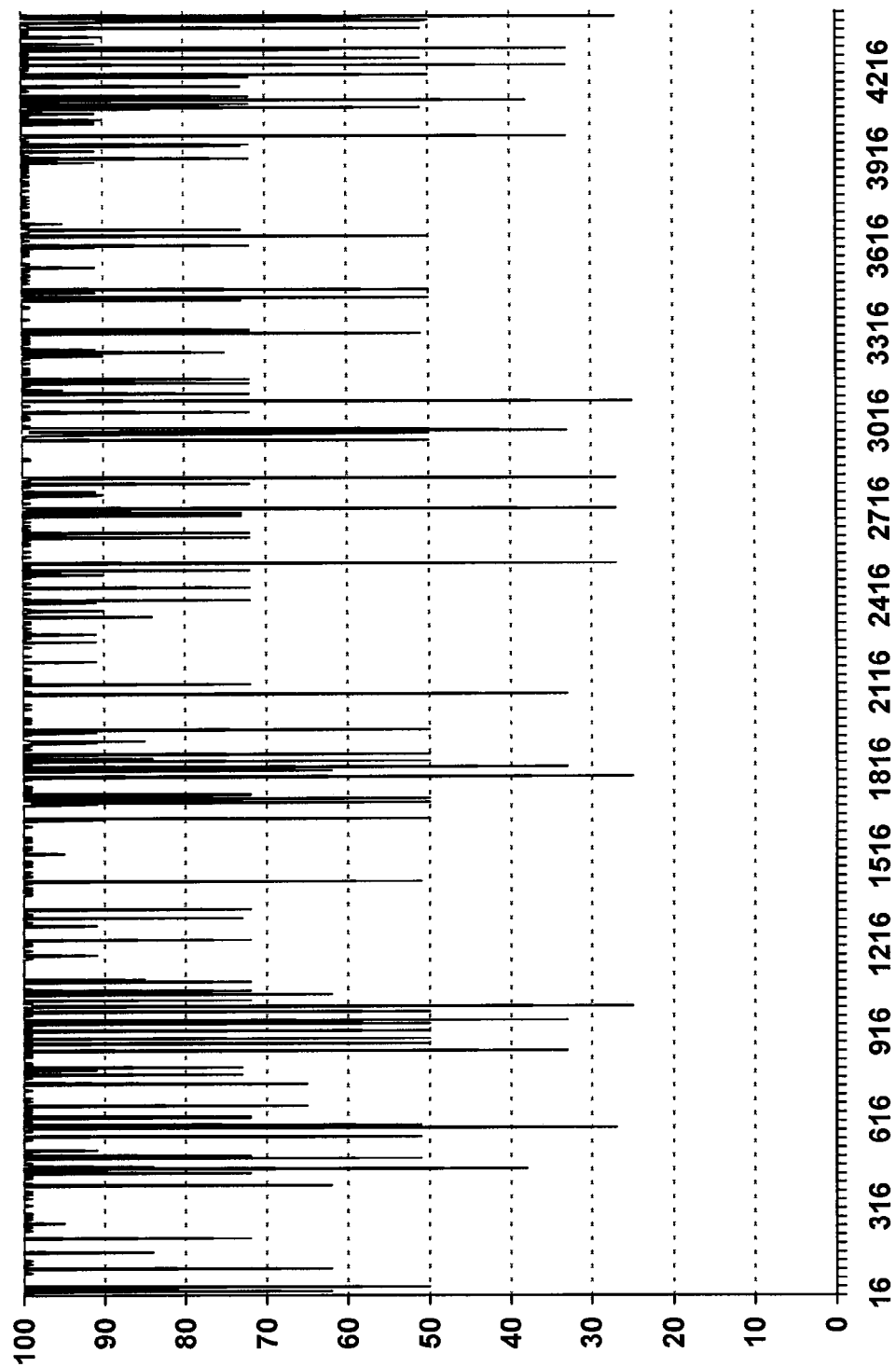
FIG. 20 shows a codon quality plot for SEQ ID NO: 19.
Figure 21:
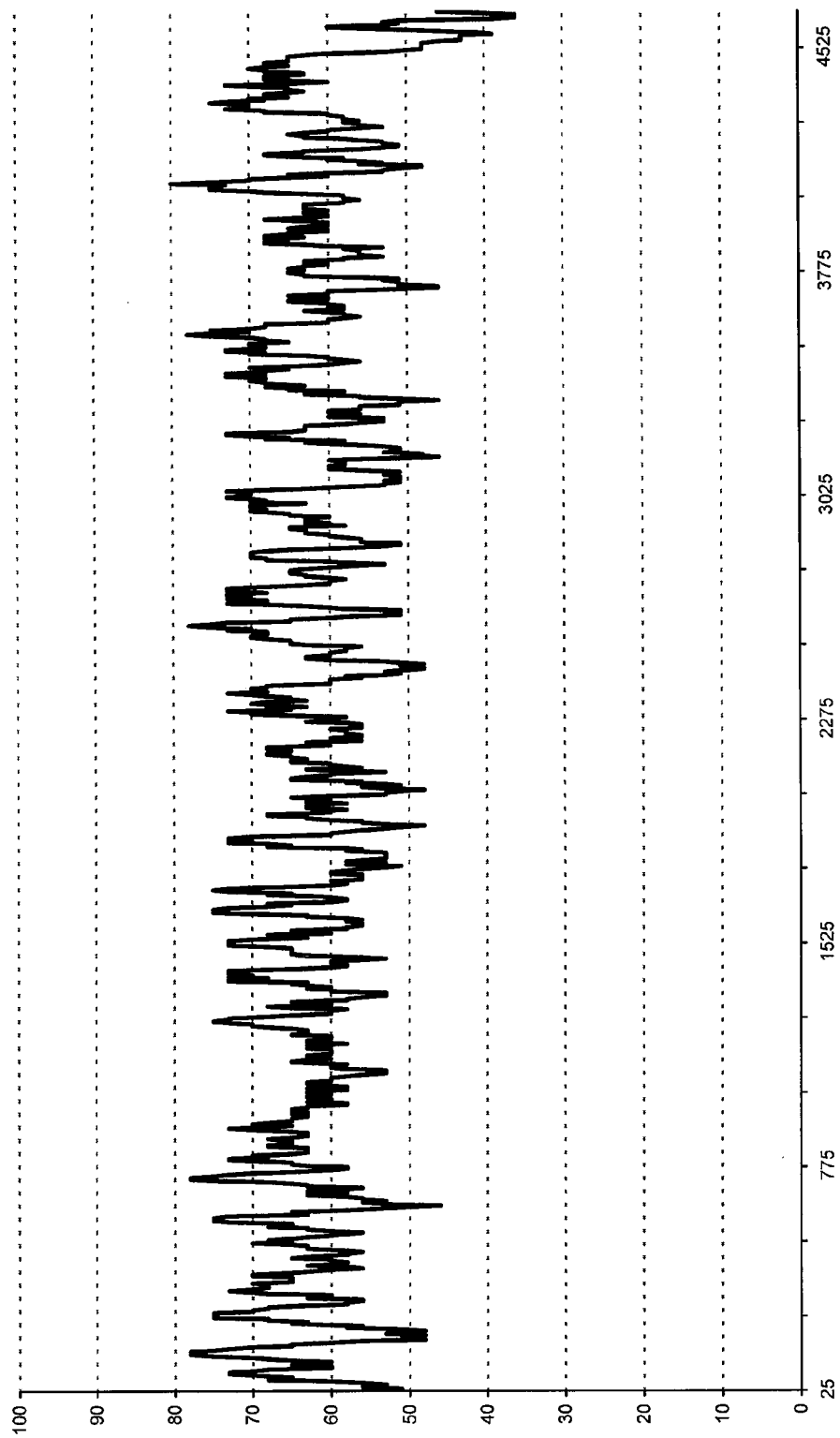
FIG. 21 shows the GC content plot for modified SEQ ID NO: 15 which is 62%.

With respect to SEQ ID NO: 14, FIG. 19 shows the percentage of sequence codons, which fall into a certain quality class. The Codon Adaptation Index is 0,96. FIG. 20 shows a codon quality plot. FIG. 21 shows a GC content plot; GC content is 62%.

The wildtype gene uses rare codons with a high frequency and the GC content is quite low which facilitates quick mRNA turnover. The optimization was successful: no negative cis-acting sites (such as splice sites, poly(A) signals, etc) which may negatively influence expression are present. GC-content was increased to prolong mRNA half-life and to improve the efficiency of vector packaging. Codon usage was adapted to the bias of *Homo sapiens* resulting in a high CAI* value (0.98). The optimized gene should therefore allow high and stable expression rates in *Homo sapiens* or other mammalian cells.

To confirm such increase expression rate, a side by side comparison of the vector expression of the liver mediated AAV2 clinical trial vector vs. double stranded and double stranded+codon modified transgene cassette (including SEQ ID NO: 12 or 15) is conducted in C57BL6 mice. The dose chosen will be one that has been shown to be sub-therapeutic but safe ($4 \times 10^{11}$ vg/kg). The animals at 8-10 weeks old will receive a single portal vein injection (n=4/serotype/dose).

These experiments are carried out in vitro and in vivo. In the in vitro experiments, C57Bl6 animals are pre-exposed to AAV1, AAV2, BNP2.5 vector, or any other suitable parvovirus vector. Four weeks post IM injection, sera is collected, and 293 cells at a density of $1\times10^5$ cells/well in 1 ml DMEM containing 10% FBS are seeded in a 24-well plate. The cells are cultured for 2-3 hrs at 37° C. and allowed to adhere to the well. The medium is removed before $1\times10^6$ particles of adenovirus dl309 are added in a final volume of 200 ul/well. The cells are further incubated at 37° C. for 1 hr and then washed twice. AAV-GFP vectors ($1\times10^8$ particles) are incubated with human sera at serial dilutions with PBS for 2 hrs at 4° C. in a total volume of 25 μl (12.5 μl serial dilution sera samples plus 12.5 μl of AAV/GFP vectors which contain 1×108 particles). The mixture is added to cells in a final volume of 200 μl and incubated overnight at 37° C. GFP expressing cells are counted under a fluorescent microscope. The percent inhibition will be calculated without serum sample as a reference. The neutralizing antibody titer is calculated using the highest dilution where the percentage of GFP expressed cells is 50% less than control without sera.

The in vivo experiments is implemented using the same C57Bl6 mice which have been primed with AAV1, AAV2, BNP2.5, or any other parvovirus suitable vector. After four weeks, the mice are challenged with BNP vector IM carrying Luc reporter and analyzed using real time imaging. Control experiments of BNP with identical dose in naive animals are used.

All publications, patent applications, patents, and other references mentioned herein are incorporated by reference in their entirety.

That which is claimed is:

1. A composition comprising an isolated optimized gene modified to increase CG sequences at least 40% relative to a wild type gene and reduce cis motifs relative to a wild type gene, wherein the optimized gene is selected from the group consisting of FVIII and FIX, wherein when the optimized gene is FVIII, the gene has the nucleotide sequence of SEQ ID NO: 12 or 15 or a nucleotide sequence having 95% identity thereto, and wherein when the optimized gene is FIX the gene has the nucleotide sequence of SEQ ID NO 7 or a nucleotide sequence having 95% identity thereof.

2. The composition of claim 1, wherein the optimized FVIII or FIX gene is included in a virus vector.

3. The composition of claim 2, wherein the virus vector is a chimeric virus vector comprising capsid components selected from AAV1, AAV2, AAV3, AAV4, AAV5, AAV6, AAV7 AAV8, AAV9, AAV10, AAV11 and AAV12 capsids.

4. The composition according to claim 1 produced by the process comprising:
   a) transfecting a host cell with an optimized FVIII or FIX gene, wherein when the optimized gene is FVIII, the gene has the nucleotide sequence of SEQ ID NO: 12 or 15or a nucleotide sequence having 95% identity thereto, and wherein when the optimized gene is FIX the gene has the nucleotide sequence of SEQ ID NO 7 or a nucleotide sequence having 95% identity thereof; and
   b) maintaining the transfected host cell under biological conditions sufficient for expression of the FVIII or FIX gene.

* * * * *

SEQUENCE LISTING

```
<160> NUMBER OF SEQ ID NOS: 19

<210> SEQ ID NO 1
<211> LENGTH: 2453
<212> TYPE: DNA
<213> ORGANISM: Artificial Sequence
<220> FEATURE:
<223> OTHER INFORMATION: Synthetic construct

<400> SEQUENCE: 1
ctggcgcgct cgctcgctca ctgaggccgc ccgggcaaag cccgggcgtc gggcgacctt     60
tggtcgcccg gcctcagtga gcgagcgagc gcgcagagag ggagtggaat tcgagctcga    120
gcttgggctg caggtcgagg gcactgggag gatgttgagt aagatggaaa actactgatg    180
acccttgcag agacagagta ttaggacatg tttgaacagg ggccgggcga tcagcaggta    240
gctctagagg atccccgtct gtctgcacat ttcgtagagc gagtgttccg atactctaat    300
ctccctaggc aaggttcata tttgtgtagg ttacttattc tccttttgtt gactaagtca    360
ataatcagaa tcagcaggtt tggagtcagc ttggcaggga tcagcagcct gggttggaag    420 gaggggggtat aaaagcccct tcaccaggag aagccgtcac acagatccac aagctcctga    480
caggaagctc taggtgactc tcttaaggta gccttgcaga agttggtcgt gaggcactgg    540
ctagccctaa ggtaagttgg cgccgtttaa gggatggttg gttggtgggg tattaatgtt    600
taattacctt ttttacaggc ctgaagatct ccaccatgca gcgcgtgaac atgatcatgg    660
ccgagagccc tggcctgatc accatctgcc tgctgggcta cctgctgagc gccgagtgca    720
ccgtgttcct ggaccacgag aacgccaaca agatcctgaa ccggcccaag agatacaaca    780
gcggcaagct ggaggagttc gtgcagggca acctggagag ggagtgcatg gaggagaagt    840
gcagcttcga ggaggccagg gaagtgttcg agaacaccga gcggaccacc gagttctgga    900
agcagtacgt ggacggcgac cagtgcgaga gcaacccttg cctgaacggc ggcagctgca    960
aggacgacat caacagctac gagtgctggt gccctttcgg cttcgagggc aagaactgcg   1020
agctggacgt gacctgcaac atcaagaacg gccgctgcga gcagttctgc aagaacagcg   1080
ccgacaacaa agtggtgtgt agctgcaccg agggctacag actggccgag aaccagaaga   1140
gctgcgagcc cgccgtgccc ttcccctgcg gcagagtgag cgtgtcccag accagcaagc   1200
tgaccagagc cgagaccgtg ttccccgacg tggactacgt gaatagcacc gaggccgaga   1260
ccatcctgga caacatcacc cagagcaccc agtccttcaa cgacttcacc agagttgtgg   1320
gcggcgagga cgccaagccc ggccagttcc cctggcaggt ggtgctgaac ggcaaagtgg   1380
```

```
atgccttctg cggcggcagc atcgtgaacg agaagtggat cgtgacagcc gcccactgcg    1440
tggagaccgg cgtgaagatc accgtggtgg ccggcgaaca caatatcgag gagaccgagc    1500
acaccgagca gaagcggaac gtcatccgga ttatccccca ccacaactac aacgccgcca    1560
tcaacaagta caaccacgac atcgccctgc tggagctgga cgagcctctg gtgctgaata    1620
gctacgtgac ccccatctgc atcgccgaca aggagtacac caacatcttc ctgaagttcg    1680
gcagcggcta cgtgtccggc tggggcagag tgttccacaa gggcagaagc gccctggtgc    1740
tgcagtacct gagagtgccc ctggtggaca gagccacctg cctgaggagc accaagttca    1800
ccatctacaa caacatgttc tgcgccggct ccacgaggg cggcagagac agctgccagg    1860
gcgacagcgg cggaccccac gtgaccgaag tggagggcac cagcttcctg accggcatca    1920
tcagctgggg cgaggagtgc gccatgaagg gcaagtacgg catctacacc aaagtgagcc    1980
ggtacgtgaa ctggatcaag gagaaaacca agctgaccct gatgagcatg ctagagctcg    2040
ctgatcagcc tcgactgtgc cttctagttg ccagccatct gttgtttgcc cctccccgt     2100 gccttccttg accctggaag gtgccactcc cactgtcctt tcctaataaa atgaggaaat    2160
tgcatcgcat tgtctgagta ggtgtcattc tattctgggg ggtggggtgg ggcaggacag    2220
caagggggag gattgggaag acaatagcag gcatgctggg gaaagcttca gctagagcat    2280
ggctacgtag ataagtagca tggcgggtta atcattaact acaaggaacc cctagtgatg    2340
gagttggcca ctccctctct gcgcgctcgc tcgctcactg aggccgggcg accaaaggtc    2400
gcccgacgcc cgggctttgc ccgggcggcc tcagtgagcg agcgagcgcg cag           2453
```

<210> SEQ ID NO 2
<211> LENGTH: 116
<212> TYPE: DNA
<213> ORGANISM: Artificial Sequence
<220> FEATURE:
<223> OTHER INFORMATION: Synthetic construct

<400> SEQUENCE: 2

```
ctggcgcgct cgctcgctca ctgaggccgc ccgggcaaag cccgggcgtc gggcgacctt    60
tggtcgcccg gcctcagtga gcgagcgagc gcgcagagag ggagtggaat tcgagc        116
```

<210> SEQ ID NO 3
<211> LENGTH: 373
<212> TYPE: DNA
<213> ORGANISM: Artificial Sequence
<220> FEATURE:
<223> OTHER INFORMATION: Synthetic construct

<400> SEQUENCE: 3

```
tcgagcttgg gctgcaggtc gagggcactg ggaggatgtt gagtaagatg gaaaactact    60
gatgaccctt gcagagacag agtattagga catgtttgaa caggggccgg gcgatcagca    120
ggtagctcta gaggatcccc gtctgtctgc acatttcgta gagcgagtgt tccgatactc    180
taatctccct aggcaaggtt catatttgtg taggttactt attctccttt tgttgactaa    240
gtcaataatc agaatcagca ggtttggagt cagcttggca gggatcagca gcctgggttg    300
gaaggagggg gtataaaagc cccttcacca ggagaagccg tcacacagat ccacaagctc    360
ctgacaggaa gct                                                       373
```

<210> SEQ ID NO 4
<211> LENGTH: 51
<212> TYPE: DNA
<213> ORGANISM: Artificial Sequence

```
<220> FEATURE:
<223> OTHER INFORMATION: Synthetic Construct

<400> SEQUENCE: 4
ctaggtgact ctcttaaggt agccttgcag aagttggtcg tgaggcactg g            51

<210> SEQ ID NO 5
<211> LENGTH: 86
<212> TYPE: DNA
<213> ORGANISM: Artificial Sequence
<220> FEATURE:
<223> OTHER INFORMATION: Synthetic construct

<400> SEQUENCE: 5
ctagccctaa ggtaagttgg cgccgtttaa gggatggttg gttggtgggg tattaatgtt   60
taattacctt ttttacaggc ctgaag                                       86

<210> SEQ ID NO 6
<211> LENGTH: 9
<212> TYPE: DNA
<213> ORGANISM: Artificial Sequence
<220> FEATURE:
<223> OTHER INFORMATION: Synthetic Construct

<400> SEQUENCE: 6 atctccacc                                                           9

<210> SEQ ID NO 7
<211> LENGTH: 2024
<212> TYPE: DNA
<213> ORGANISM: Artificial Sequence
<220> FEATURE:
<223> OTHER INFORMATION: Synthetic Construct

<400> SEQUENCE: 7
ctggcgcgct cgctcgctca ctgaggccgc ccgggcaaag cccgggcgtc gggcgacctt   60
tggtcgcccg gcctcagtga gcgagcgagc gcgcagagag ggagtggaat tcgagctcga  120
gcttgggctg caggtcgagg gcactgggag gatgttgagt aagatggaaa actactgatg  180
acccttgcag agacagagta ttaggacatg tttgaacagg ggccgggcga tcagcaggta  240
gctctagagg atccccgtct gtctgcacat ttcgtagagc gagtgttccg atactctaat  300
ctccctaggc aaggttcata tttgtgtagg ttacttattc tccttttgtt gactaagtca  360
ataatcagaa tcagcaggtt tggagtcagc ttggcaggga tcagcagcct gggttggaag  420 gaggggggtat aaaagcccct tcaccaggag aagccgtcac acagatccac aagctcctga  480
caggaagctc taggtgactc tcttaaggta gccttgcaga agttggtcgt gaggcactgg  540
ctagccctaa ggtaagttgg cgccgtttaa gggatggttg gttggtgggg tattaatgtt  600
taattacctt ttttacaggc ctgaagatct ccaccatgca gcgcgtgaac atgatcatgg  660
ccgagagccc tggcctgatc accatctgcc tgctgggcta cctgctgagc gccgagtgca  720
ccgtgttcct ggaccacgag aacgccaaca agatcctgaa ccggcccaag agatacaaca  780
gcggcaagct ggaggagttc gtgcagggca acctggagag ggagtgcatg gaggagaagt  840
gcagcttcga ggaggccagg gaagtgttcg agaacaccga gcggaccacc gagttctgga  900
agcagtacgt ggacggcgac cagtgcgaga gcaacccttg cctgaacggc ggcagctgca  960
aggacgacat caacagctac gagtgctggt gccctttcgg cttcgagggc aagaactgcg 1020
agctggacgt gacctgcaac atcaagaacg gccgctgcga gcagttctgc aagaacagcg 1080
```

```
ccgacaacaa agtggtgtgt agctgcaccg agggctacag actggccgag aaccagaaga    1140
gctgcgagcc cgccgtgccc ttccctgcg gcagagtgag cgtgtcccag accagcaagc     1200
tgaccagagc cgagaccgtg ttccccgacg tggactacgt gaatagcacc gaggccgaga    1260
ccatcctgga caacatcacc cagagcaccc agtccttcaa cgacttcacc agagttgtgg    1320
gcggcgagga cgccaagccc ggccagttcc cctggcaggt ggtgctgaac ggcaaagtgg    1380
atgccttctg cggcggcagc atcgtgaacg agaagtggat cgtgacagcc gcccactgcg    1440
tggagaccgg cgtgaagatc accgtggtgg ccggcgaaca caatatcgag gagaccgagc    1500
acaccgagca gaagcggaac gtcatccgga ttatccccca ccacaactac aacgccgcca    1560
tcaacaagta caaccacgac atcgccctgc tggagctgga cgagcctctg gtgctgaata    1620
gctacgtgac ccccatctgc atcgccgaca aggagtacac caacatcttc ctgaagttcg    1680
gcagcggcta cgtgtccggc tggggcagag tgttccacaa gggcagaagc gccctggtgc    1740
tgcagtacct gagagtgccc ctggtggaca gagccacctg cctgaggagc accaagttca    1800
ccatctacaa caacatgttc tgcgccggct ccacgaggg cggcagagac agctgccagg     1860
gcgacagcgg cggaccccac gtgaccgaag tggagggcac cagcttcctg accggcatca    1920
tcagctgggg cgaggagtgc gccatgaagg gcaagtacgg catctacacc aaagtgagcc    1980
ggtacgtgaa ctggatcaag gagaaaacca agctgacctg atga                    2024

<210> SEQ ID NO 8
<211> LENGTH: 239
<212> TYPE: DNA
<213> ORGANISM: Artificial Sequence
<220> FEATURE:
<223> OTHER INFORMATION: Synthetic Construct

<400> SEQUENCE: 8
gcatgcctag agctcgctga tcagcctcga ctgtgccttc tagttgccag ccatctgttg      60 tttgccccctc ccccgtgcct tccttgaccc tggaaggtgc cactcccact gtcctttcct    120
aataaaatga ggaaattgca tcgcattgtc tgagtaggtg tcattctatt ctggggggtg     180
gggtggggca ggacagcaag ggggaggatt gggaagacaa tagcaggcat gctggggaa      239

<210> SEQ ID NO 9
<211> LENGTH: 190
<212> TYPE: DNA
<213> ORGANISM: Artificial Sequence
<220> FEATURE:
<223> OTHER INFORMATION: Synthetic Construct

<400> SEQUENCE: 9
agcttcagct agagcatggc tacgtagata agtagcatgg cgggttaatc attaactaca      60
aggaacccct agtgatggag ttggccactc cctctctgcg cgctcgctcg ctcactgagg     120
ccgggcgacc aaaggtcgcc cgacgcccgg gctttgcccg gcggcctca gtgagcgagc      180 gagcgcgcag                                                             190

<210> SEQ ID NO 10
<211> LENGTH: 4428
<212> TYPE: DNA
<213> ORGANISM: Artificial Sequence
<220> FEATURE:
<223> OTHER INFORMATION: Synthetic Construct

<400> SEQUENCE: 10
ggtaccgcca ccatgcagat cgagctgtcc acatgctttt ttctgtgcct gctgcggttc      60
```

```
tgcttcagcg ccacccggcg gtactacctg ggcgccgtgg agctgtcctg ggactacatg      120
cagagcgacc tgggcgagct gcccgtggac gcccggttcc cccccagagt gcccaagagc      180
ttccccttca acaccagcgt ggtgtacaag aaaaccctgt tcgtggagtt caccgtgcac      240
ctgttcaaca tcgccaagcc caggcccccc tggatgggcc tgctgggccc caccatccag      300
gccgaggtgt acgacaccgt ggtgatcacc ctgaagaaca tggccagcca cccgtgagc       360 ctgcacgccg tgggcgtgag ctactggaag gcctccgagg cgccgagta cgacgaccag       420 accagccagc gggagaaaga ggacgacaaa gtctttcctg cggcagcca cacctacgtg       480 tggcaggtcc tgaaagaaaa cggccccatg gcctccgacc cctgtgcct gacctacagc       540 tacctgagcc acgtggacct ggtgaaggac ctgaacagcg ggctgattgg ggccctgctg      600
gtctgccggg agggcagcct ggccaaagag aaaacccaga ccctgcacaa gttcatcctg      660
ctgttcgccg tgttcgacga gggcaagagc tggcacagcg agaccaagaa cagcctgatg      720
caggaccggg acgccgcctc tgccagagcc tgggcccaaga tgcacaccgt gaacggctac      780
gtgaacagaa gcctgcccgg cctgattggc tgccaccgga gagcgtgta ctggcacgtg       840 atcggcatgg gcaccacacc cgaggtgcac agcatctttc tggaagggca cccttttctg      900
gtgcggaacc accggcaggc cagcctggaa atcagcccta tcaccttcct gaccgcccag      960
acactgctga tggacctggg ccagttcctg ctgtttgcc acatcagctc tcaccagcac      1020
gacggcatgg aagcctacgt gaaggtggac tcctgccccg aggaacccca gctgcggatg     1080
aagaacaacg aggaagccga ggactacgac gacgacctga ccgacagcga gatggacgtg     1140
gtgcggttcg acgacgacaa cagccccagc ttcatccaga tcagaagcgt ggccaagaag     1200 cacccccaaga cctgggtgca ctacatcgcc gccgaggaag aggactggga ctacgccccc     1260
ctggtgctgg cccccgacga cagaagctac aagagccagt acctgaacaa tggcccccag     1320 cggatcgggcc ggaagtacaa gaaagtgcgg ttcatggcct acaccgacga gaccttcaag    1380
acccgggagg ccatccagca cgagagcggc atcctgggcc cctgctgta cggcgaagtg      1440 ggcgacacac tgctgatcat cttcaagaac caggccagcc ggcctacaa catctacccc      1500 cacggcatca ccgacgtgcg gccctgtac agcaggcggc tgcccaaggg cgtgaagcac      1560
ctgaaggact tccccatcct gcccggcgag atcttcaagt acaagtggac cgtgaccgtg     1620
gaggacggcc ccaccaagag cgaccccaga tgcctgaccc ggtactacag cagcttcgtg     1680
aacatggaac gggacctggc ctccgggctg atcggacctc tgctgatctg ctacaaagaa     1740
agcgtggacc agcggggcaa ccagatcatg agcgacaagc ggaacgtgat cctgttcagc     1800
gtgttcgatg agaaccggtc ctggtatctg accgagaaca tccagcggtt tctgcccaac     1860
cctgccgggg tgcagctgga agatcccgag ttcaggcca gcaacatcat gcactccatc      1920
aatggctacg tgttcgacag cctgcagctg tccgtgtgtc tgcacgaggt ggcctactgg     1980
tacatcctga gcatcggcgc ccagaccgac ttcctgagcg tgttcttcag cggctacacc    2040
ttcaagcaca agatggtgta cgaggacacc ctgaccctgt tccctttcag cggcgagacc    2100
gtgttcatga gcatggaaaa ccccggcctg tggatcctgg gctgccacaa cagcgacttc     2160
cggaaccggg gcatgaccgc cctgctgaag gtgtccagct gcgacaagaa caccggcgac     2220
tactacgagg acagctacga ggatatcagc gcctacctgc tgtccaagaa caacgccatc     2280
gagcccagaa gcttcagcca gaacagccgg caccccagca ccggcagaa gcagttcaac      2340 gccaccccc ctgtgctgaa gcggcaccag agagagatca cccggaccac cctgcagtcc     2400
```

-continued

```
gaccaggaag agatcgatta cgacgacacc atcagcgtgg agatgaaaaa agaagatttc    2460
gacatctacg acgaggacga gaaccagagc ccccggtcct tccagaagaa aacccggcac    2520
tactttatcg ccgccgtgga gcggctgtgg gactacggca tgagcagcag ccccacgtg    2580 ctgcggaacc gggcccagag cggcagcgtg ccccagttca agaaagtggt gttccaggaa    2640
ttcaccgacg gcagcttcac ccagcccctg taccggggcg agctgaacga gcacctgggg    2700
ctgctggggc cctacatcag ggccgaagtg gaggacaaca tcatggtgac cttccggaat    2760
caggccagca gaccctactc cttctacagc agcctgatca gctacgaaga ggaccagcgg    2820
cagggcgctg aaccccggaa gaacttcgtg aagcccaatg agaccaagac ctacttctgg    2880
aaagtgcagc accacatggc ccccaccaag gacgagttcg actgcaaggc ctgggcctac    2940
ttcagcgacg tggatctgga aaaggacgtg cactctggac tgattggccc tctgctggtg    3000
tgccacacca acaccctgaa ccccgcccac ggccggcagg tgaccgtgca ggaattcgcc    3060
ctgttcttca ccatcttcga cgagaccaag tcctggtact tcaccgagaa tatggaacgg    3120
aactgcagag ccccctgcaa catccagatg gaagatccta ccttcaaaga gaactaccgg    3180
ttccacgcca tcaacggcta catcatggac accctgcctg gcctggtgat ggcccaggac    3240
cagaggatcc ggtggtatct gctgtccatg ggcagcaacg agaatatcca cagcatccac    3300
ttcagcggcc acgtgttcac cgtgaggaag aaagaagagt acaagatggc cctgtacaac    3360
ctgtaccccg gcgtgttcga gaccgtggag atgctgccca gcaaggccgg catctggcgg    3420
gtggagtgtc tgatcggcga gcacctgcat gccgggatga gcaccctgtt tctggtgtac    3480
agcaacaagt gccagacccc cctgggcatg ccagcggcc acatccggga cttccagatc    3540
accgcctccg gccagtacgg ccagtgggcc cccaagctgg cccggctgca ctacagcggc    3600
agcatcaacg cctggtccac caaagagccc ttcagctgga tcaaggtgga cctgctggcc    3660
cctatgatca tccacggcat taagacccag ggcgccaggc agaagttcag cagcctgtac    3720
atcagccagt tcatcatcat gtacagcctg gacggcaaga gtggcagac ctaccggggc    3780 aacagcaccg gcaccctgat ggtgttcttc ggcaacgtgg acagcagcgg catcaagcac    3840
aacatcttca ccccccccat catcgcccgg tacatccggc tgcaccccac ccactacagc    3900
atcagatcca ccctgcggat ggaactgatg ggctgcgacc tgaactcctg cagcatgcct    3960
ctgggcatgg aaagcaaggc catcagcgac gcccagatca cagccagcag ctacttcacc    4020
aacatgttcg ccacctggtc ccctccaag gccaggctgc acctgcaggg ccggtccaac    4080
gcctggcggc ctcaggtgaa caaccccaaa gaatggctgc aggtggactt tcagaaaacc    4140
atgaaggtga ccggcgtgac cacccagggc gtgaaaagcc tgctgaccag catgtacgtg    4200
aaagagtttc tgatcagcag cagccaggac ggccaccagt ggaccctgtt ctttcagaac    4260
ggcaaggtga agtgttcca gggcaaccag gactccttca cccccgtggt gaactccctg    4320 gaccccccc tgctgacccg ctacctgcgg atccacccc agtcttgggt gcaccagatc    4380
gccctgagga tggaagtgct gggatgtgag gcccaggatc tgtactga              4428
```

<210> SEQ ID NO 11
<211> LENGTH: 12
<212> TYPE: DNA
<213> ORGANISM: Artificial Sequence
<220> FEATURE:
<223> OTHER INFORMATION: Synthetic Construct

<400> SEQUENCE: 11

```
ggtaccgcca cc                                                          12
```

<210> SEQ ID NO 12
<211> LENGTH: 4428
<212> TYPE: DNA
<213> ORGANISM: Artificial Sequence
<220> FEATURE:
<223> OTHER INFORMATION: Synthetic construct

<400> SEQUENCE: 12

| | | | | | |
|---|---|---|---|---|---|
| ggtaccgcca | ccatgcagat | cgagctgtcc | acatgctttt | ttctgtgcct | gctgcggttc | 60 |
| tgcttcagcg | ccacccggcg | gtactacctg | ggcgccgtgg | agctgtcctg | ggactacatg | 120 |
| cagagcgacc | tgggcgagct | gcccgtggac | gcccggttcc | cccccagagt | gcccaagagc | 180 |
| ttccccttca | acaccagcgt | ggtgtacaag | aaaaccctgt | tcgtggagtt | caccgtgcac | 240 |
| ctgttcaaca | tcgccaagcc | caggcccccc | tggatgggcc | tgctgggccc | caccatccag | 300 |
| gccgaggtgt | acgacaccgt | ggtgatcacc | ctgaagaaca | tggccagcca | ccccgtgagc | 360 |
| ctgcacgccg | tgggcgtgag | ctactggaag | gcctccgagg | gcgccgagta | cgacgaccag | 420 |
| accagccagc | gggagaaaga | ggacgacaaa | gtctttcctg | gcggcagcca | cacctacgtg | 480 |
| tggcaggtcc | tgaaagaaaa | cggcccccatg | gcctccgacc | ccctgtgcct | gacctacagc | 540 |
| tacctgagcc | acgtggacct | ggtgaaggac | ctgaacagcg | ggctgattgg | ggccctgctg | 600 |
| gtctgccggg | agggcagcct | ggccaaagag | aaaacccaga | ccctgcacaa | gttcatcctg | 660 |
| ctgttcgccg | tgttcgacga | gggcaagagc | tggcacagcg | agaccaagaa | cagcctgatg | 720 |
| caggaccggg | acgccgcctc | tgccagagcc | tggcccaaga | tgcacaccgt | gaacggctac | 780 |
| gtgaacagaa | gcctgcccgg | cctgattggc | tgccaccgga | agagcgtgta | ctggcacgtg | 840 |
| atcggcatgg | gcaccacacc | cgaggtgcac | agcatctttc | tggaagggca | cacctttctg | 900 |
| gtgcggaacc | accggcaggc | cagcctggaa | atcagcccta | tcaccttcct | gaccgcccag | 960 |
| acactgctga | tggacctggg | ccagttcctg | ctgttttgcc | acatcagctc | tcaccagcac | 1020 |
| gacggcatgg | aagcctacgt | gaaggtggac | tcctgccccg | aggaacccca | gctgcggatg | 1080 |
| aagaacaacg | aggaagccga | ggactacgac | gacgacctga | ccgacagcga | gatggacgtg | 1140 |
| gtgcggttcg | acgacgacaa | cagccccagc | ttcatccaga | tcagaagcgt | ggccaagaag | 1200 |
| caccccaaga | cctgggtgca | ctacatcgcc | gccgaggaag | aggactggga | ctacgccccc | 1260 |
| ctggtgctgg | cccccgacga | cagaagctac | aagagccagt | acctgaacaa | tggccccag | 1320 |
| cggatcggcc | ggaagtacaa | gaaagtgcgg | ttcatggcct | acaccgacga | gaccttcaag | 1380 |
| acccgggagg | ccatccagca | cgagagcggc | atcctgggcc | cctgctgta | cggcgaagtg | 1440 |
| ggcgacacac | tgctgatcat | cttcaagaac | caggccagcc | ggccctacaa | catctacccc | 1500 |
| cacggcatca | ccgacgtgcg | gcccctgtac | agcaggcggc | tgcccaaggg | cgtgaagcac | 1560 |
| ctgaaggact | tccccatcct | gcccggcgag | atcttcaagt | acaagtggac | cgtgaccgtg | 1620 |
| gaggacggcc | ccaccaagag | cgaccccaga | tgcctgaccc | ggtactacag | cagcttcgtg | 1680 |
| aacatggaac | gggacctggc | ctccgggctg | atcggacctc | tgctgatctg | ctacaaagaa | 1740 |
| agcgtggacc | agcggggcaa | ccagatcatg | agcgacaagc | ggaacgtgat | cctgttcagc | 1800 |
| gtgttcgatg | agaaccggtc | ctggtatctg | accgagaaca | tccagcggtt | tctgcccaac | 1860 |
| cctgccgggg | tgcagctgga | agatcccgag | ttccaggcca | gcaacatcat | gcactccatc | 1920 |
| aatggctacg | tgttcgacag | cctgcagctg | tccgtgtgtc | tgcacgaggt | ggcctactgg | 1980 |
| tacatcctga | gcatcggcgc | ccagaccgac | ttcctgagcg | tgttcttcag | cggctacacc | 2040 |

```
ttcaagcaca agatggtgta cgaggacacc ctgaccctgt tccctttcag cggcgagacc    2100
gtgttcatga gcatggaaaa ccccggcctg tggatcctgg gctgccacaa cagcgacttc    2160
cggaaccggg gcatgaccgc cctgctgaag gtgtccagct gcgacaagaa caccggcgac    2220
tactacgagg acagctacga ggatatcagc gcctacctgc tgtccaagaa caacgccatc    2280
gagcccagaa gcttcagcca gaacagccgg caccccagca cccggcagaa gcagttcaac    2340
gccaccccc ctgtgctgaa gcggcaccag agagagatca cccggaccac cctgcagtcc    2400
gaccaggaag agatcgatta cgacgacacc atcagcgtgg agatgaaaaa agaagatttc    2460
gacatctacg acgaggacga gaaccagagc ccccggtcct tccagaagaa aacccggcac    2520
tactttatcg ccgccgtgga gcggctgtgg gactacggca tgagcagcag ccccacgtg    2580
ctgcggaacc gggcccagag cggcagcgtg ccccagttca agaaagtggt gttccaggaa    2640
ttcaccgacg gcagcttcac ccagcccctg taccggggcg agctgaacga gcacctgggg    2700
ctgctggggc cctacatcag ggccgaagtg gaggacaaca tcatggtgac cttccggaat    2760
caggccagca gaccctactc cttctacagc agcctgatca gctacgaaga ggaccagcgg    2820
cagggcgctg aaccccggaa gaacttcgtg aagcccaatg agaccaagac ctacttctgg    2880
aaagtgcagc accacatggc ccccaccaag gacgagttcg actgcaaggc ctgggcctac    2940
ttcagcgacg tggatctgga aaaggacgtg cactctggac tgattggccc tctgctggtg    3000
tgccacacca cacccctgaa ccccgcccac ggccggcagg tgaccgtgca ggaattcgcc    3060
ctgttcttca ccatcttcga cgagaccaag tcctggtact tcaccgagaa tatggaacgg    3120
aactgcagag ccccctgcaa catccagatg gaagatccta ccttcaaaga gaactaccgg    3180
ttccacgcca tcaacggcta catcatggac accctgcctg gcctggtgat ggcccaggac    3240
cagaggatcc ggtggtatct gctgtccatg ggcagcaacg agaatatcca cagcatccac    3300
ttcagcggcc acgtgttcac cgtgaggaag aaagaagagt acaagatggc cctgtacaac    3360
ctgtaccccg gcgtgttcga gaccgtggag atgctgccca gcaaggccgg catctggcgg    3420
gtggagtgtc tgatcggcga gcacctgcat gccgggatga gcaccctgtt tctggtgtac    3480
agcaacaagt gccagacccc cctgggcatg gccagcggcc acatccggga cttccagatc    3540
accgcctccg ccagtacgg ccagtgggcc cccaagctgg cccggctgca ctacagcggc    3600
agcatcaacg cctggtccac caaagagccc ttcagctgga tcaaggtgga cctgctggcc    3660
cctatgatca tccacggcat taagacccag ggcgccaggc agaagttcag cagcctgtac    3720
atcagccagt tcatcatcat gtacagcctg gacggcaaga gtggcagac ctaccggggc    3780
aacagcaccg gcaccctgat ggtgttcttc ggcaacgtgg acagcagcgg catcaagcac    3840
aacatcttca ccccccccat catcgcccgg tacatccggc tgcaccccac ccactacagc    3900
atcagatcca ccctgcggat ggaactgatg ggctgcgacc tgaactcctg cagcatgcct    3960
ctgggcatgg aaagcaaggc catcagcgac gcccagatca cagccagcag ctacttcacc    4020
aacatgttcg ccacctggtc cccctccaag gccaggctgc acctgcaggg ccggtccaac    4080
gcctggcggc ctcaggtgaa caaccccaaa gaatggctgc aggtggactt tcagaaaacc    4140
atgaaggtga ccggcgtgac cacccagggc gtgaaaagcc tgctgaccag catgtacgtg    4200
aaagagtttc tgatcagcag cagccaggac ggccaccagt ggaccctgtt ctttcagaac    4260
ggcaaggtga agtgttcca gggcaaccag gactccttca ccccccgtggt gaactccctg    4320
gaccccccc tgctgacccg ctacctgcgg atccacccc agtcttgggt gcaccagatc    4380
gccctgagga tggaagtgct gggatgtgag gcccaggatc tgtactga                 4428
```

<210> SEQ ID NO 13
<211> LENGTH: 240
<212> TYPE: DNA
<213> ORGANISM: Artificial Sequence
<220> FEATURE:
<223> OTHER INFORMATION: Synthetic construct

<400> SEQUENCE: 13

```
ctcgaggggt ggccactgca gcacctgcca ctgccgtcac ctctccctcc tcagctccag    60
ggcagtgtcc ctccctggct tgccttctac ctttgtgcta aatcctagca gacactgcct   120
tgaagcctcc tgaattaact atcatcagtc ctgcatttct ttggtggggg gccaggaggg   180
tgcatccaat ttaacttaac tcttacctat tttctgcagg ggatctcagt cgacgagctc   240
```

<210> SEQ ID NO 14
<211> LENGTH: 4656
<212> TYPE: DNA
<213> ORGANISM: Artificial Sequence
<220> FEATURE:
<223> OTHER INFORMATION: Synthetic construct

<400> SEQUENCE: 14

```
atgcagatcg agctgagtac ctgcttttc ctctgcctgc tgcggttctg cttcagcgcc    60
acccggcggt actacctggg cgccgtggag ctgagttggg actacatgca gagcgacctg   120
ggcgagctgc ccgtggacgc ccggttcccc cctcgggtgc ccaagagctt ccccttcaac   180
accagcgtgg tgtacaagaa aaccctgttc gtggagttca ccgtgcacct gttcaacatc   240
gccaagccca ggccccctg atgggcctg ctgggcccca ccatccaggc cgaggtgtac   300
gacaccgtgg tgatcaccct gaagaacatg gccagccacc ccgtgagcct gcacgccgtg   360
ggcgtgagct actggaaggc cagtgagggc gccgagtacg acgaccagac cagccagcgg   420
gagaaagagg acgacaaggt tttccctggc ggcagccaca cctacgtgtg gcaggtcctg   480
aaagaaaacg gccccatggc ctccgacccc ctgtgcctga cctacagcta cctgagccac   540
gtggacctgg tcaaggacct gaacagcggc ctgatcggcg cgctgctggt ctgccgggag   600
ggcagcctgg ccaaagagaa aacccagacc ctgcacaagt tcatcctgct gttcgctgtg   660
ttcgacgagg gcaagagctg gcacagcgag accaagaaca gcctgatgca ggaccgggac   720
gccgccagcg ctcgcgcctg gcccaagatg cacaccgtga acggatacgt gaaccggtcc   780
ctgcccgggc tgatcggctg ccaccggaag agcgtgtact ggcacgtgat cggcatgggc   840
accacgcccg aggtgcacag catcttcctc gagggccaca ccttcctcgt gcggaaccac   900
cggcaggcca gctcgagat cagccccatc accttcctca ccgcccagac gctgctgatg   960
gacctgggcc agttcctgct cttctgccac atcagctcgc accagcacga cggcatggaa  1020
gcctacgtga aggtggacag ttgccccgag gaacccagc tgcggatgaa gaacaacgag  1080
gaagccgagg attacgacga cgacctgacc gacagcgaga tggacgtggt gcggttcgac  1140
gacgacaaca gccccagctt catccagatc cggtccgtgg ccaagaagca ccccaagacc  1200
tgggtgcact acatcgccgc cgaggaagag gactgggact acgcccccct ggtgctggcc  1260
cccgacgacc ggtcctacaa gagccagtac ctgaacaacg gcccccagcg gatcggccgg  1320
aagtacaaga agtgcggtt catggcctac accgacgaga ccttcaagac ccgggaggcc  1380
atccagcacg agagcggcat cctgggcccc ctgctgtacg cgaggtcgg cgacaccctg  1440 ctgatcatct tcaagaacca ggccagccgg ccctacaaca tctaccccca cggcatcacc  1500
```

```
gacgtgcggc ccctgtacag caggcggctg cccaagggcg tgaagcacct gaaggacttc    1560
cccatcctgc ccggcgagat cttcaagtac aagtggaccg tgaccgtgga ggacggcccc    1620
accaagagcg accccgctg cctcacccgg tactacagca gcttcgtgaa catggagcgg     1680
gacctggcct ccggcctcat cgggcccctg ctcatctgct acaaagaaag cgtgaccag     1740 cggggcaacc agatcatgag cgacaagcgg aacgtgatcc tgttctcggt gttcgacgag    1800
aaccggagtt ggtatctgac ggagaacatc cagcggttcc tccccaaccc tgccggcgtg    1860
cagctcgagg accccgagtt ccaggccagc aacatcatgc actccatcaa tggctacgtg    1920
ttcgacagcc tgcagctgtc cgtgtgcctc cacgaggtgg cctactggta catcctgagc    1980
atcggcgccc agaccgactt cctgagcgtg ttcttcagcg gctacacctt caagcacaag    2040
atggtgtacg aggacaccct gaccctgttc ccgttcagcg gcgagaccgt gttcatgagc    2100
atggaaaacc ccggcctgtg gatcctgggc tgccacaaca gcgacttccg gaaccggggc    2160
atgaccgccc tgctgaaggt gtccagctgc gacaagaaca ccggcgacta ctacgaggac    2220
agctacgagg acatcagcgc ctacctgctg tccaagaaca cgccatcga gccccggtcc     2280 ttcagccaga cagccggca ccccagcacc cggcagaagc agttcaacgc caccccccct     2340
gtgctgaagc ggcaccagcg cgagatcacc cggaccaccc tgcagtccga ccaggaagag    2400
atcgactacg acgacaccat cagcgtggag atgaagaaag aggacttcga catctacgac    2460
gaggacgaga accagagccc ccgcagcttc cagaagaaaa cccggcacta cttcatcgcc    2520
gcggtggagc ggctgtggga ctacggcatg agcagcagcc ccacgtgct gcggaaccgg     2580 gcccagagcg gcagcgtgcc ccagttcaag aaagtggtgt ccaggaatt caccgacggc     2640 agcttcaccc agcccctgta ccggggcgag ctgaacgagc acctggggct gctggggccc    2700
tacatccgcg cggaggtgga ggacaacatc atggtgacct tccggaacca ggcctcccgc    2760
ccctactcct tctacagcag cctgatcagc tacgaagagg accagcggca gggcgcggag    2820 cccccggaaga acttcgtgaa gcccaacgag accaagacct acttctggaa ggtgcagcac    2880
cacatggccc ccaccaagga cgagttcgac tgcaaggcct gggcctactt cagcgacgtg    2940
gacctcgaga aggacgtgca ctccgggctc atcggcccgc tcctcgtgtg ccacaccaac    3000
accctgaacc ccgcccacgg ccggcaggtg accgtgcagg aattcgccct gttcttcacc    3060
atcttcgacg agaccaagtc gtggtacttc accgagaaca tggaacgcaa ctgcagggcc    3120
ccctgcaaca tccagatgga agatcccacc ttcaaagaga actaccggtt ccacgccatc    3180
aacggctaca tcatggacac cctgcccggc ctggtgatgg cccaggacca gcgcatccgg    3240
tggtatctgc tgtccatggg cagcaacgag aacatccaca gcatccactt cagcggccac    3300
gtgttcaccg tccggaagaa agaagagtac aagatggccc tgtacaacct gtaccccggc    3360
gtgttcgaga ccgtggagat gctgcccagc aaggccggca tctggcgggt ggagtgcctg    3420 atcgggagc acctccacgc cggcatgtcc acctgttcc tcgtgtacag caacaagtgc    3480 cagaccccc tgggcatggc cagcggccac atccgggact tccagatcac cgcctccggc    3540
cagtacggcc agtgggcccc caagctggcc cggctgcact acagcggcag catcaacgcc    3600
tggtccacca aagagccctt cagctggatc aaggtggacc tgctcgcccc catgatcatc    3660
cacgggatca agacccaggg cgccaggcag aagttcagca gcctgtacat cagccagttc    3720
atcatcatgt acagcctgga cggcaagaag tggcagacct accggggcaa cagcaccggc    3780
accctgatgg tgttcttcgg caacgtggac agcagcggca tcaagcacaa catcttcaac    3840
ccccccatca tcgcccggta catccggctg cacccccacc actacagcat ccggtccacc    3900
```

| | |
|---|---|
| ctgcggatgg aactgatggg ctgcgacctg aactcctgca gcatgcccct ggggatggaa | 3960 |
| agcaaggcca tcagcgacgc ccagatcacg gccagcagct acttcaccaa catgttcgcc | 4020 |
| acctggtccc cctccaaggc ccgcctgcac ctgcagggcc ggtccaacgc ctggcggcct | 4080 |
| caggtcaaca accccaaaga gtggctgcag gttgacttcc agaaaaccat gaaggtgacc | 4140 |
| ggcgtgacca cccaggggt gaagagcctg ctgaccagca tgtacgtgaa agagttcctc | 4200 |
| atcagcagca gccaggacgg ccaccagtgg acgctgttct tccagaacgg caaggtcaag | 4260 |
| gtgttccagg gcaaccagga cagtttcacg cccgtggtga actccctgga ccccccctg | 4320 |
| ctgacccgct acctgcggat ccaccccag agctgggtcc accagatcgc cctgcgcatg | 4380 |
| gaagtcctcg gctgcgaggc gcaggacctg tactgactcg aggggtggcc actgcagcac | 4440 |
| ctgccactgc cgtcacctct ccctcctcag ctccagggca gtgtccctcc ctggcttgcc | 4500 |
| ttctaccttt gtgctaaatc ctagcagaca ctgccttgaa gcctcctgaa ttaactatca | 4560 |
| tcagtcctgc atttctttgg tggggggcca ggagggtgca tccaatttaa cttaactctt | 4620 |
| acctattttc tgcaggggat ctcagtcgac gagctc | 4656 |

<210> SEQ ID NO 15
<211> LENGTH: 4416
<212> TYPE: DNA
<213> ORGANISM: Artificial Sequence
<220> FEATURE:
<223> OTHER INFORMATION: Synthetic construct

<400> SEQUENCE: 15

| | |
|---|---|
| atgcagatcg agctgagtac ctgcttttc ctctgcctgc tgcggttctg cttcagcgcc | 60 |
| acccggcggt actacctggg cgccgtggag ctgagttggg actacatgca gagcgacctg | 120 |
| ggcgagctgc ccgtggacgc ccggttcccc cctcgggtgc ccaagagctt ccccttcaac | 180 |
| accagcgtgg tgtacaagaa aaccctgttc gtggagttca ccgtgcacct gttcaacatc | 240 |
| gccaagccca ggcccccctg gatgggcctg ctgggcccca ccatccaggc cgaggtgtac | 300 |
| gacaccgtgg tgatcaccct gaagaacatg gccagccacc ccgtgagcct gcacgccgtg | 360 |
| ggcgtgagct actggaaggc cagtgagggc gccgagtacg acgaccagac cagccagcgg | 420 |
| gagaagagg acgacaaggt tttccctggc ggcagccaca cctacgtgtg gcaggtcctg | 480 |
| aaagaaaacg gccccatggc ctccgacccc ctgtgcctga cctacagcta cctgagccac | 540 |
| gtggacctgg tcaaggacct gaacagcggc ctgatcggcg cgctgctggt ctgccgggag | 600 |
| ggcagcctgc ccaaagagaa aacccagacc ctgcacaagt tcatcctgct gttcgctgtg | 660 |
| ttcgacgagg gcaagagctg gcacagcgag accaagaaca gcctgatgca ggaccgggac | 720 |
| gccgccagcg ctcgcgcctg gcccaagatg cacaccgtga acggatacgt gaaccggtcc | 780 |
| ctgcccggc tgatcggctg ccaccggaag agcgtgtact ggcacgtgat cggcatgggc | 840 |
| accacgcccg aggtgcacag catcttcctc gagggccaca ccttcctcgt gcggaaccac | 900 |
| cggcaggcca gcctcgagat cagcccatc accttcctca ccgcccagac gctgctgatg | 960 |
| gacctgggcc agttcctgct cttctgccac atcagctcgc accagcacga cggcatggaa | 1020 |
| gcctacgtga aggtggacag ttgccccgag gaacccagc tgcggatgaa gaacaacgag | 1080 |
| gaagccgagg attacgacga cgacctgacc gacagcgaga tggacgtggt gcggttcgac | 1140 |
| gacgacaaca gccccagctt catccagatc cggtccgtgg ccaagaagca ccccaagacc | 1200 |
| tgggtgcact acatcgccgc cgaggaagag gactgggact acgccccct ggtgctggcc | 1260 |

-continued

```
cccgacgacc ggtcctacaa gagccagtac ctgaacaacg ggccccagcg gatcggccgg    1320
aagtacaaga aagtgcggtt catggcctac accgacgaga ccttcaagac ccgggaggcc    1380
atccagcacg agagcggcat cctgggcccc ctgctgtacg gcgaggtcgg cgacaccctg    1440
ctgatcatct tcaagaacca ggccagccgg ccctacaaca tctaccccca cggcatcacc    1500
gacgtgcggc ccctgtacag caggcggctg cccaagggcg tgaagcacct gaaggacttc    1560
cccatcctgc ccggcgagat cttcaagtac aagtggaccg tgaccgtgga ggacggcccc    1620
accaagagcg accccgctg cctcacccgg tactacagca gcttcgtgaa catggagcgg    1680
gacctggcct ccggcctcat cgggcccctg ctcatctgct acaaagaaag cgtgaccag    1740 cggggcaacc agatcatgag cgacaagcgg aacgtgatcc tgttctcggt gttcgacgag    1800
aaccggagtt ggtatctgac ggagaacatc cagcggttcc tccccaaccc tgccggcgtg    1860
cagctcgagg accccgagtt ccaggccagc aacatcatgc actccatcaa tggctacgtg    1920
ttcgacagcc tgcagctgtc cgtgtgcctc cacgaggtgg cctactggta catcctgagc    1980
atcggcgccc agaccgactt cctgagcgtg ttcttcagcg gctacacctt caagcacaag    2040
atggtgtacg aggacaccct gaccctgttc ccgttcagcg gcgagaccgt gttcatgagc    2100
atggaaaacc ccggcctgtg gatcctgggc tgccacaaca gcgacttccg gaaccggggc    2160
atgaccgccc tgctgaaggt gtccagctgc gacaagaaca ccggcgacta ctacgaggac    2220
agctacgagg acatcagcgc ctacctgctg tccaagaaca cgccatcga gccccggtcc    2280 ttcagccaga cagccggca ccccagcacc cggcagaagc agttcaacgc cacccccct    2340 gtgctgaagc ggcaccagcg cgagatcacc cggaccaccc tgcagtccga ccaggaagag    2400
atcgactacg acgacaccat cagcgtggag atgaagaaag aggacttcga catctacgac    2460
gaggacgaga accagagccc ccgcagcttc cagaagaaaa cccggcacta cttcatcgcc    2520
gcggtggagc ggctgtggga ctacggcatg agcagcagcc ccacgtgct gcggaaccgg    2580 gcccagagcg gcagcgtgcc ccagttcaag aaagtggtgt ccaggaatt caccgacggc    2640 agcttcaccc agccctgta ccggggcgag ctgaacgagc acctggggct gctggggccc    2700
tacatccgcg cggaggtgga ggacaacatc atggtgacct tccggaacca ggcctccgc    2760 ccctactcct tctacagcag cctgatcagc tacgaagagg accagcggca gggcgcggag    2820
ccccggaaga acttcgtgaa gcccaacgag accaagacct acttctggaa ggtgcagcac    2880
cacatggccc ccaccaagga cgagttcgac tgcaaggcct gggcctactt cagcgacgtg    2940
gacctcgaga aggacgtgca ctccgggctc atcggcccgc tcctcgtgtg ccacaccaac    3000
accctgaacc ccgcccacgg ccggcaggtg accgtgcagg aattcgccct gttcttcacc    3060
atcttcgacg agaccaagtc gtggtacttc accgagaaca tggaacgcaa ctgcagggcc    3120
ccctgcaaca tccagatgga agatcccacc ttcaaagaga actaccggtt ccacgccatc    3180
aacggctaca tcatggacac cctgcccggc ctggtgatgg cccaggacca gcgcatccgg    3240
tggtatctgc tgtccatggg cagcaacgag aacatccaca gcatccactt cagcggccac    3300
gtgttcaccg tccggaagaa agaagagtac aagatggccc tgtacaacct gtaccccggc    3360
gtgttcgaga ccgtggagat gctgcccagc aaggccggca tctggcgggt ggagtgcctg    3420
atcggggagc acctccacgc cggcatgtcc accctgttcc tcgtgtacag caacaagtgc    3480
cagacccccc tgggcatggc cagcggccac atcagggact tccagatcac cgcctccggc    3540
cagtacggcc agtgggcccc caagctggcc cggctgcact acagcggcag catcaacgcc    3600
tggtccacca agagcccctt cagctggatc aaggtggacc tgctcgcccc catgatcatc    3660
```

```
cacgggatca agacccaggg cgccaggcag aagttcagca gcctgtacat cagccagttc    3720
atcatcatgt acagcctgga cggcaagaag tggcagacct accggggcaa cagcaccggc    3780
accctgatgg tgttcttcgg caacgtggac agcagcggca tcaagcacaa catcttcaac    3840 cccccccatca tcgcccggta catccggctg caccccaccc actacagcat ccggtccacc    3900
ctgcggatgg aactgatggg ctgcgacctg aactcctgca gcatgcccct ggggatggaa    3960
agcaaggcca tcagcgacgc ccagatcacg gccagcagct acttcaccaa catgttcgcc    4020
acctggtccc cctccaaggc ccgcctgcac ctgcagggcc ggtccaacgc ctggcggcct    4080
caggtcaaca accccaaaga gtggctgcag gttgacttcc agaaaaccat gaaggtgacc    4140
ggcgtgacca cccaggggt gaagagcctg ctgaccagca tgtacgtgaa agagttcctc    4200
atcagcagca gccaggacgg ccaccagtgg acgctgttct ccagaacgg caaggtcaag    4260 gtgttccagg gcaaccagga cagtttcacg cccgtggtga actccctgga ccccccctg    4320 ctgacccgct acctgcggat ccaccccag agctgggtcc accagatcgc cctgcgcatg    4380
gaagtcctcg gctgcgaggc gcaggacctg tactga                              4416

<210> SEQ ID NO 16
<211> LENGTH: 240
<212> TYPE: DNA
<213> ORGANISM: Artificial Sequence
<220> FEATURE:
<223> OTHER INFORMATION: Synthetic construct

<400> SEQUENCE: 16
ctcgaggggt ggccactgca gcacctgcca ctgccgtcac ctctccctcc tcagctccag     60
ggcagtgtcc ctccctggct tgccttctac ctttgtgcta atcctagca gacactgcct    120 tgaagcctcc tgaattaact atcatcagtc ctgcattct ttggtggggg gccaggaggg    180
tgcatccaat ttaacttaac tcttacctat tttctgcagg ggatctcagt cgacgagctc    240

<210> SEQ ID NO 17
<211> LENGTH: 2211
<212> TYPE: DNA
<213> ORGANISM: Artificial Sequence
<220> FEATURE:
<223> OTHER INFORMATION: Synthetic sequence

<400> SEQUENCE: 17
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt ggggggcaacc tcggacgagc agtcttccag    360
gcgaaaaaga gggttcttga acctctgggc ctggttgagg aacctgttaa acggctccg    420 ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag ccccctctgg tctgggaact    600
aatacgatgg ctacaggcag tggcgcacca atggcagaca ataacgaggg cgccgacgga    660
gtgggtaatt cctcgggaaa ttggcattgc gattccacat ggatgggcga cagagtcatc    720
```

| | |
|---|---|
| accaccagca cccgaacctg ggccctgccc acctacaaca accacctcta caaacaaatt | 780 |
| tccagcgctt caacgggagc ctcgaacgac aatcactact ttggctacag cacccctttgg | 840 |
| gggtattttg acttcaacag attccactgc cacttttcac cacgtgactg gcaaagactc | 900 |
| atcaacaaca actggggatt ccgacccaag agactcaact tcaagctctt taacattcaa | 960 |
| gtcaaagagg tcacgcagaa tgacggtacg acgacgattg ccaataacct taccagcacg | 1020 |
| gttcaggtgt ttactgactc ggagtaccag ctcccgtacg tcctcggctc ggcgcatcaa | 1080 |
| ggatgcctcc cgccgttccc agcagacgtc ttcatggtgc cacagtatgg atacctcacc | 1140 |
| ctgaacaacg ggagtcaggc agtaggacgc tcttcatttt actgcctgga gtactttcct | 1200 |
| tctcagatgc tgcgtaccgg aaacaacttt accttcagct acacttttga ggacgttcct | 1260 |
| ttccacagca gctacgctca cagccagagt ctggaccgtc tcatgaatcc tctcatcgac | 1320 |
| cagtacctgt attacttgag cagaacaaac actccaagtg gaaccaccac gcagtcaagg | 1380 |
| cttcagttttt ctcaggccgg agcgagtgac attcgggacc agtctaggaa ctggcttcct | 1440 |
| ggaccctgtt accgccagca gcgagtatca agacatctg cggataacaa caacagtgaa | 1500 |
| tactcgtgga ctggagctac caagtaccac ctcaatggca gagactctct ggtgaatccg | 1560 |
| ggcccggcca tggcaagcca aaggacgat gaagaaaagt tttttcctca gagcggggtt | 1620 |
| ctcatctttg ggaagcaagg ctcagagaaa acaaatgtgg acattgaaaa ggtcatgatt | 1680 |
| acagacgaag aggaaatcag gacaaccaat cccgtggcta cggagcagta tggttctgta | 1740 |
| tctaccaacc tccagagagg caacagacaa gcagctaccg cagatgtcaa cacacaaggc | 1800 |
| gttcttccag gcatggtctg gcaggacaga gatgtgtacc ttcaggggcc catctgggca | 1860 |
| aagattccac acacggacgg acattttcac ccctctcccc tcatgggtgg attcggactt | 1920 |
| aaacacccctc ctccacagat tctcatcaag aacaccccgg tacctgcgaa tccttcgacc | 1980 |
| accttcagtg cggcaaagtt tgcttccttc atcacacagt actccacggg acaggtcagc | 2040 |
| gtggagatcg agtgggagct gcagaaggaa aacagcaaac gctggaatcc cgaaattcag | 2100 |
| tacacttcca actacgccaa gtctgtcaat gtggacttta ctgtggacaa taatggcgtg | 2160 |
| tattcagagc ctcgccccat ggcaccagaa tacctgactc gtaatctgta a | 2211 |

<210> SEQ ID NO 18
<211> LENGTH: 1395
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| atgcagcgcg tgaacatgat catggcagaa tcaccaggcc tcatcaccat ctgcctttta | 60 |
| ggatatctac tcagtgctga atgtacagtt tttcttgatc atgaaaacgc caacaaaatt | 120 |
| ctgaatcggc caaagaggta taattcaggt aaattggaag agtttgttca agggaacctt | 180 |
| gagagagaat gtatggaaga aaagtgtagt tttgaagaag cacgagaagt ttttgaaaac | 240 |
| acggaaagaa caactgaatt ttggaagcag tatgttgatg gtgaccagtg tgagtccaat | 300 |
| ccatgtttaa atggcggcag ttgcaaggat gacattaatt cctatgaatg ttggtgtccc | 360 |
| tttggatttg aaggaaagaa ctgtgagctc gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgcggccgc | 540 |
| gtttctgttt cacaaacttc taagctcacc cgtgctgaga ctgttttttcc tgatgtggac | 600 |

```
tatgtaaatt ctactgaagc tgaaaccatt ttggataaca tcactcaaag cacccaatca    660
tttaatgact tcactcgggt tgttggtgga aagatgccaa aaccaggtca attcccttgg    720
caggttgttt tgaatggtaa agttgatgca ttctgtggag gctctatcgt taatgaaaaa    780
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga gatcagcttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac ccatgttact gaagtggaa    1260 gggaccagtt tcttaactgg aattattagc tggggtgaag agtgtgcaat gaaaggcaaa   1320
tatggaatat ataccaaggt atcccggtat gtcaactgga ttaaggaaaa aacaaagctc   1380
acttaatgag catgc                                                   1395

<210> SEQ ID NO 19
<211> LENGTH: 4650
<212> TYPE: DNA
<213> ORGANISM: Artificial Sequence
<220> FEATURE:
<223> OTHER INFORMATION: Synthetic Construct

<400> SEQUENCE: 19
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc caaaatcttt tccattcaac    180
acctcagtcg tgtacaaaaa gactctgttt gtagaattca cggttcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
```

```
tgggtacatt acattgctgc tgaagaggag gactgggact atgctccctt agtcctcgcc    1260
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag agaaactgt cttcatgtcg     2100 atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc cacccacca    2340 gtcttgaaac gccatcaacg ggaaataact cgtactactc ttcagtcaga tcaagaggaa    2400
attgactatg atgataccat atcagttgaa atgaagaagg aagattttga catttatgat    2460
gaggatgaaa atcagagccc ccgcagcttt caaaagaaaa cacgacacta ttttattgct    2520 gcagtgggaga ggctctggga ttatgggatg agtagctccc cacatgttct aagaaacagg    2580
gctcagagtg gcagtgtccc tcagttcaag aaagttgttt ccaggaatt tactgatggc    2640 tcctttactc agcccttata ccgtggagaa ctaaatgaac attttgggact cctggggcca    2700 tatataagag cagaagttga agataatatc atggtaactt tcagaaatca ggcctctcgt    2760
ccctattcct tctattctag ccttatttct tatgaggaag atcagaggca aggagcagaa    2820
cctagaaaaa actttgtcaa gcctaatgaa accaaaactt acttttggaa agtgcaacat    2880
catatggcac ccactaaaga tgagtttgac tgcaaagcct gggcttattt ctctgatgtt    2940
gacctggaaa aagatgtgca ctcaggcctg attggacccc ttctggtctg ccacactaac    3000
acactgaacc ctgctcatgg gagacaagtg acagtacagg aatttgctct gttttcacc    3060 atctttgatg agaccaaaag ctggtacttc actgaaaata tggaaagaaa ctgcagggct    3120
ccctgcaata tccagatgga agatcccact tttaaagaga attatcgctt ccatgcaatc    3180
aatggctaca taatggatac actacctggc ttagtaatgg ctcaggatca aaggattcga    3240
tggtatctgc tcagcatggg cagcaatgaa acatccatt ctattcattt cagtggacat    3300
gtgttcactg tacgaaaaaa agaggagtat aaaatggcac tgtacaatct ctatccaggt    3360 gttttgaga cagtggaaat gttaccatcc aaagctggaa tttggcgggt ggaatgcctt    3420
attggcgagc atctacatgc tgggatgagc acacttttc tggtgtacag caataagtgt    3480
cagactcccc tgggaatggc ttctggacac attagagatt tcagattac agcttcagga    3540 caatatggac agtgggcccc aaagctggcc agacttcatt attccggatc aatcaatgcc    3600
```

```
tggagcacca aggagccctt ttcttggatc aaggtggatc tgttggcacc aatgattatt    3660
cacggcatca agacccaggg tgcccgtcag aagttctcca gcctctacat ctctcagttt    3720
atcatcatgt atagtcttga tgggaagaag tggcagactt atcgaggaaa ttccactgga    3780
accttaatgg tcttctttgg caatgtggat tcatctggga taaaacacaa tatttttaac    3840
cctccaatta ttgctcgata catccgtttg cacccaactc attatagcat tcgcagcact    3900
cttcgcatgg agttgatggg ctgtgattta aatagttgca gcatgccatt gggaatggag    3960
agtaaagcaa tatcagatgc acagattact gcttcatcct actttaccaa tatgtttgcc    4020
acctggtctc cttcaaaagc tcgacttcac ctccaaggga ggagtaatgc ctggagacct    4080
caggtgaata atccaaaaga gtggctgcaa gtggacttcc agaagacaat gaaagtcaca    4140
ggagtaacta ctcagggagt aaaatctctg cttaccagca tgtatgtgaa ggagttcctc    4200
atctccagca gtcaagatgg ccatcagtgg actctctttt ttcagaatgg caaagtaaag    4260
gtttttcagg gaaatcaaga ctccttcaca cctgtggtga actctctaga cccaccgtta    4320
ctgactcgct accttcgaat tcacccccag agttgggtgc accagattgc cctgaggatg    4380
gaggttctgg gctgcgaggc acaggacctc tactgactcg aggggtggcc actgcagcac    4440
ctgccactgc cgtcacctct ccctcctcag ctccagggca gtgtccctcc ctggcttgcc    4500 ttctacccttt gtgctaaatc ctagcagaca ctgccttgaa gcctcctgaa ttaactatca    4560
tcagtcctgc atttctttgg tggggggcca ggagggtgca tccaatttaa cttaactctt    4620
acctattttc tgcaggggat ctcagtcgac                                     4650
```